(12) United States Patent
Howard et al.

(10) Patent No.: US 11,980,757 B2
(45) Date of Patent: May 14, 2024

(54) TRANSDURAL ELECTRODE DEVICE FOR STIMULATION OF THE SPINAL CORD

(71) Applicants: University of Iowa Research Foundation, Iowa City, IA (US); University Of Virginia Patent Foundation, Charlottesville, VA (US); Direct Spinal Therapeutics Inc., Charlottesville, VA (US)

(72) Inventors: Matthew A. Howard, Iowa City, IA (US); George T. Gillies, Charlottesville, VA (US); Logan Helland, Iowa City, IA (US); Royce Woodroffe, Iowa City, IA (US); Charles Romans, Iowa City, IA (US); Saul Wilson, Iowa City, IA (US); Daryl R. Kipke, Ann Arbor, MI (US); David J. Anderson, Ann Arbor, MI (US); Daniel J. O'Connell, Charlottesville, VA (US)

(73) Assignees: University of Iowa Research Foundation, Iowa City, IA (US); University Of Virginia Patent Foundation, Charlottesville, VA (US); Direct Spinal Therapeutics Inc., Charlottesville, VA (US)

(*) Notice: Subject to any disclaimer, the term of this patent is extended or adjusted under 35 U.S.C. 154(b) by 189 days.

(21) Appl. No.: 17/108,862

(22) Filed: Dec. 1, 2020

(65) Prior Publication Data
US 2021/0101010 A1 Apr. 8, 2021

Related U.S. Application Data

(63) Continuation-in-part of application No. PCT/US2019/035256, filed on Jun. 3, 2019.
(Continued)

(51) Int. Cl.
*A61N 1/36* (2006.01)
*A61B 5/24* (2021.01)
*A61N 1/05* (2006.01)

(52) U.S. Cl.
CPC .......... *A61N 1/36071* (2013.01); *A61B 5/24* (2021.01); *A61N 1/0558* (2013.01); *A61N 1/36062* (2017.08)

(58) Field of Classification Search
CPC .......... A61N 1/36071; A61N 1/36062; A61N 1/0558; A61B 5/24
(Continued)

(56) References Cited

U.S. PATENT DOCUMENTS 3,724,467 A  4/1973  Avery et al.
4,633,889 A * 1/1987  Talalla ................. A61N 1/0551
                                                       607/117
(Continued)

FOREIGN PATENT DOCUMENTS

WO  2003063949 A2  8/2003
WO  2006029257 A2  3/2006
(Continued)

OTHER PUBLICATIONS

Capogrosso et al., Advantages of Soft Subdural Implants for the Delivery of Electrochemical Neuromodulation Therapies to the Spinal Cord, Journal of Neural Engineering, Institute of Physics Publishing, Bristol, GB, vol. 15, No. 2, Feb. 16, 2018, pp. 1-15.
(Continued)

*Primary Examiner* — Carl H Layno
*Assistant Examiner* — Michael J Lau
(74) *Attorney, Agent, or Firm* — Kilpatrick Townsend & Stockton LLP

(57) ABSTRACT

The spinal cord stimulation device of this invention is configured for implantation into a patient so as to traverse
(Continued)

the dura mater that surrounds the spinal cord. Placing the device in this location provides direct contact between the electrode and the cerebrospinal fluid (CSF), in close proximity to the spinal cord. The device has an intradural portion and an extradural portion that compresses and seals the dural membrane between them, securing the device in position and preventing leakage of CSF. The position of the device may be stabilized in relation to the spinal cord by way of a laminoplasty plate, bridging between the device and a vertebra. The device is electronically powered by an implanted pulse generator that produces a spectrum of signals to interrupt or otherwise attenuate transmission of pain mediating neural signals through the spinal cord. Once the device is implanted into a patient, it provides improved stimulation efficiency, reduced power requirements, and potentially an improved clinical outcome, compared with previously available technology.

20 Claims, 36 Drawing Sheets

Related U.S. Application Data

(60) Provisional application No. 62/697,641, filed on Jul. 13, 2018, provisional application No. 62/679,515, filed on Jun. 1, 2018.

(58) Field of Classification Search
USPC .......................................................... 607/46
See application file for complete search history.

(56) References Cited

U.S. PATENT DOCUMENTS

| | | | |
|---|---|---|---|
| 5,002,053 A | 3/1991 | Garcia-Rill et al. | |
| 6,319,241 B1* | 11/2001 | King | A61N 1/05 607/116 |
| 6,999,820 B2 | 2/2006 | Jordan | |
| 7,107,104 B2 | 9/2006 | Keravel et al. | |
| 7,333,857 B2 | 2/2008 | Campbell | |
| 7,697,995 B2* | 4/2010 | Cross, Jr. | A61N 1/0553 607/117 |
| 7,962,218 B2 | 6/2011 | Balzer et al. | |
| 8,170,675 B2 | 5/2012 | Alataris et al. | |
| 8,224,453 B2 | 7/2012 | De Ridder | |
| 8,295,945 B1* | 10/2012 | Thacker | A61N 1/0558 607/117 |
| 8,346,366 B2 | 1/2013 | Arle et al. | |
| 8,359,102 B2 | 1/2013 | Alataris et al. | |
| 8,712,533 B2 | 4/2014 | Alataris et al. | |
| 8,838,248 B2 | 9/2014 | Walker et al. | |
| 8,892,209 B2 | 11/2014 | Alataris et al. | |
| 9,179,875 B2 | 11/2015 | Hua | |
| 9,205,261 B2* | 12/2015 | Kim | A61N 1/36017 |
| 9,254,379 B2* | 2/2016 | Howard | A61N 1/0558 |
| 9,364,660 B2 | 6/2016 | Howard et al. | |
| 9,386,934 B2 | 7/2016 | Parker et al. | |
| 9,403,008 B2 | 8/2016 | Howard | |
| 9,486,621 B2* | 11/2016 | Howard | A61N 1/375 |
| 9,572,976 B2 | 2/2017 | Howard et al. | |
| 9,586,039 B2* | 3/2017 | Bornzin | A61N 1/0531 |
| 9,630,012 B2 | 4/2017 | Carroll | |
| 9,937,348 B1* | 4/2018 | Bradley | A61N 1/36171 |
| 9,937,349 B2 | 4/2018 | Grandhe | |
| 9,950,165 B2 | 4/2018 | Howard | |
| 10,071,240 B2 | 9/2018 | Howard et al. | |
| 10,278,600 B2 | 5/2019 | Parker et al. | |
| 11,413,449 B2 | 8/2022 | Howard et al. | |
| 2004/0167584 A1 | 8/2004 | Carroll et al. | |
| 2005/0055065 A1 | 3/2005 | Campbell | |
| 2006/0052826 A1 | 3/2006 | Kim et al. | |
| 2006/0052835 A1 | 3/2006 | Kim et al. | |
| 2006/0074456 A1 | 4/2006 | Pyles et al. | |
| 2006/0173522 A1* | 8/2006 | Osorio | A61N 1/0553 607/116 |
| 2007/0010862 A1 | 1/2007 | Osypka et al. | |
| 2008/0234791 A1* | 9/2008 | Arle | A61B 5/389 607/117 |
| 2010/0057115 A1* | 3/2010 | Rao | A61B 17/11 606/151 |
| 2010/0057178 A1 | 3/2010 | Simon | |
| 2010/0105987 A1 | 4/2010 | Miles et al. | |
| 2010/0274312 A1 | 10/2010 | Alataris et al. | |
| 2011/0184488 A1 | 7/2011 | De Ridder | |
| 2011/0224755 A1* | 9/2011 | Arle | A61N 1/37288 607/48 |
| 2012/0283835 A1 | 11/2012 | Bentley et al. | |
| 2013/0274846 A1 | 10/2013 | Lad et al. | |
| 2014/0236259 A1 | 8/2014 | Colantonio | |
| 2015/0005680 A1 | 1/2015 | Lipani | |
| 2015/0343205 A1* | 12/2015 | Howard | A61N 1/37518 607/46 |
| 2016/0213917 A1* | 7/2016 | Dalm | A61N 1/0558 |
| 2017/0157390 A1* | 6/2017 | Howard | A61N 1/0558 |
| 2018/0369577 A1 | 12/2018 | Howard | |
| 2021/0101010 A1 | 4/2021 | Howard et al. | |

FOREIGN PATENT DOCUMENTS

| | | |
|---|---|---|
| WO | 2010124139 A1 | 10/2010 |
| WO | 2013154758 A1 | 10/2013 |

OTHER PUBLICATIONS

International Application No. PCT/US2019/035256, International Preliminary Report on Patentability dated Dec. 1, 2020, 10 pages.

* cited by examiner

Electrode implant with deployment unit

Deployed using a screw design to secure intradural and extradural plates onto the dura layer. The deployment unit is a hook and turn release mechanism.

Linear dural incision

FIG. 19A

Long arm inserter into subdural space

Short arm

FIG. 19B

Gap positioned over 'long' arm of ALA

No gap between electrode housing and dura at 'short' end of ALA

Short arm now in subdural space

FIG. 19C

Compression gasket in final position

FIG. 19D

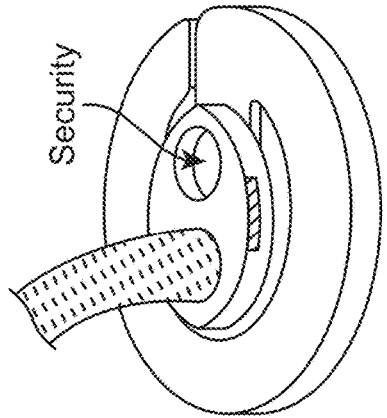
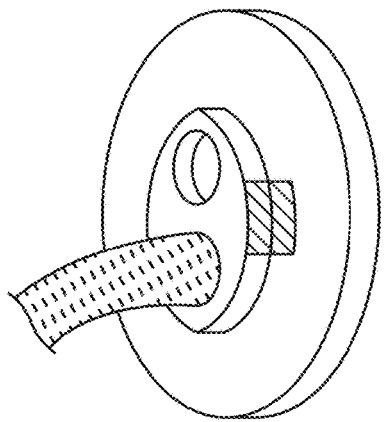
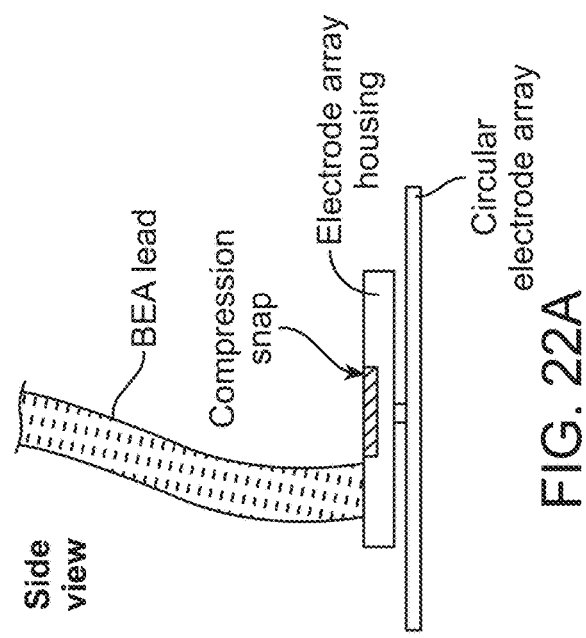
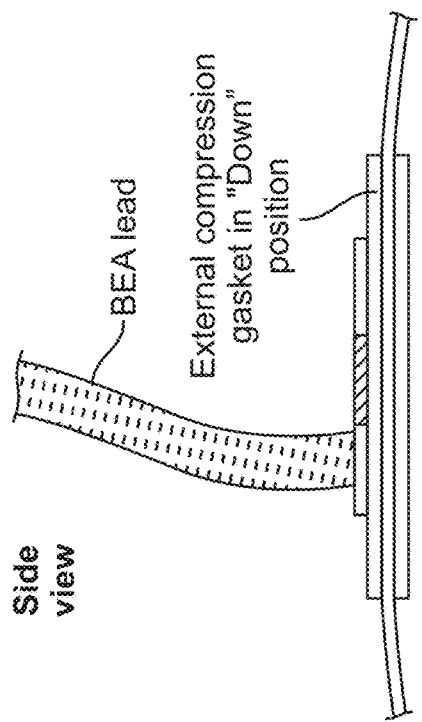

1P1 → 1P2

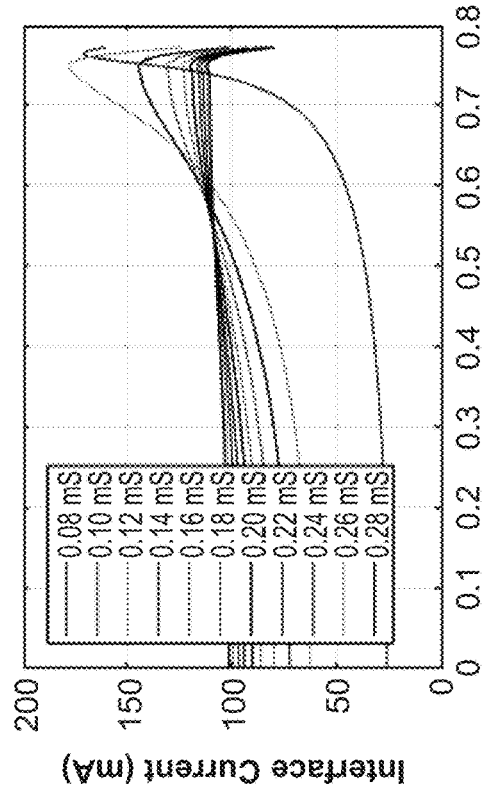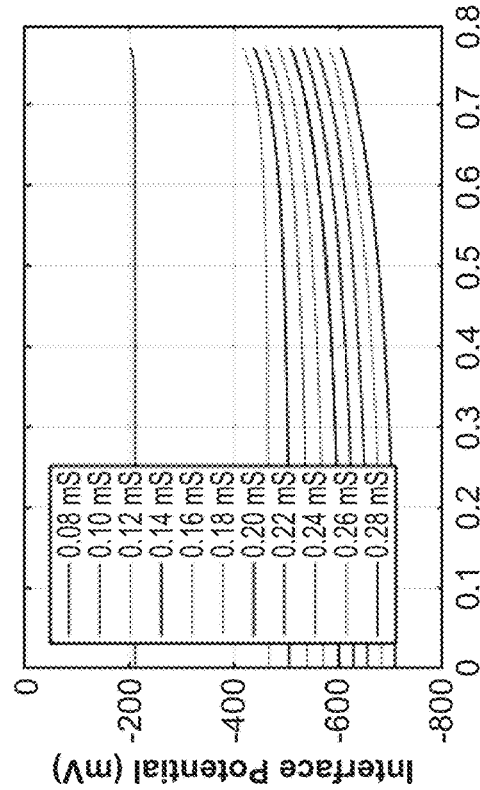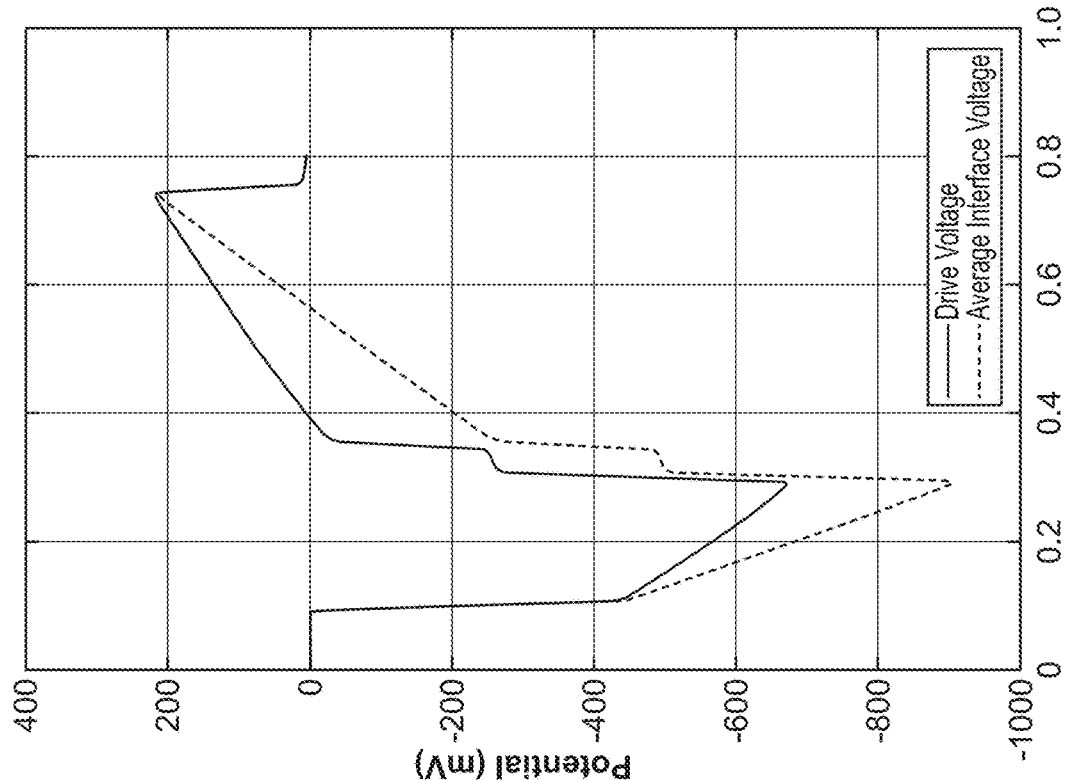

Extradural assembly with silicon overmolding

Threaded transdural assembly

Intradural assembly

Laminoplasty Plate

TRANSDURAL ELECTRODE DEVICE FOR STIMULATION OF THE SPINAL CORD

REFERENCE TO PRIOR APPLICATIONS

This application is a continuation-in-part of international application PCT/US2019/035256, which was filed on Jun. 3, 2019 and published as WO 2019/232544 on Dec. 5, 2019. The PCT application claims the priority benefit of provisional U.S. patent applications 62/697,641, filed Jul. 13, 2018; and 62/679,515, filed Jun. 1, 2018. The aforelisted priority applications are hereby incorporated herein by reference in their entirety for all purposes.

FIELD OF THE INVENTION

The invention relates generally to the field of medical devices for management of conditions that are caused at least in part by deleterious transmission of neurological impulses via the spinal cord. In particular, it provides improved devices and their use for applying electrical stimulation to the spinal cord.

BACKGROUND

Intractable pain and spinal cord injuries are both major public health problems. Pain can be the consequence of failed back surgery, complex regional pain syndromes, neurodegenerative processes, and trauma. In the U.S. alone, it is inadequately treated in over one million patients, and midline spinal pain is the nation's leading cause of lost work and disability. Almost 300,000 patients suffer from the effects of spinal cord injury (SCI), including partial or complete loss of motor, sensory and autonomic functions. These clinical conditions create an enormous economic, clinical and emotional burden on the patients and their families, and on society as a whole.

There are devices that have been designed for spinal cord stimulation (SCS) from inside the dura. U.S. Pat. Nos. 9,364,660 and 9,486,621 provide an electrode array that can be implanted directly against the spinal cord. U.S. Pat. Nos. 9,254,379 and 9,572,976 describe how such an SCS device can be secured in position by way of an assembly that is affixed to a vertebra. U.S. Pat. Nos. 9,403,008 and 9,950,165 and pre-grant publication US 2018/0369577 A1 describe how these devices can be used to deliver high frequency stimulation, thereby causing propagation of action potential patterns within the spinal cord that mediate pain perception. U.S. Pat. No. 10,071,240 describes floating electrodes that engage and accommodate movement of the spinal cord, and other aspects and configurations of intradural SCS devices.

Nevro Corp. (Redwood City, CA) has developed SCS devices that provide high frequency stimulation from the extradural space. Aspects of the Nevro devices are described in U.S. Pat. Nos. 8,170,675, 8,359,102, 8,712,533, 8,838,248 and 8,892,209. They are commercially distributed under the marks HF10® and Senza®.

Pre-grant publication US 2013/0274846 A1 (Lad) refers to methods and devices for stimulating the spinal cord. U.S. Pat. No. 6,319,241 (King) refers to techniques for positioning therapy delivery elements within a spinal cord or a brain. Pre-grant publication US 2006/0173522 A1 (Osorio) reflects on anchoring of a medical device component adjacent a dural membrane of the brain or spinal cord. U.S. Pat. No. 3,724,467 (Avery) proposes an electrode implant for neurostimulation of the spinal cord. In unrelated work, US 2010/0057115 A1 (Rao) proposes a surgical method and clamping apparatus for repair of a defect in a dural membrane or a vascular wall.

Pre-grant publication US 2006/0052835 A1 (Kim) proposes methods for stimulating the spinal cord and nervous system. U.S. Pat. No. 9,630,012 (Carroll) proposes technology for spinal cord stimulation with inferential current. U.S. Pat. No. 9,937,349 (Grandhe) outlines systems for programming a neuromodulation system. U.S. Pat. No. 9,937,348 (Bradley) proposes a system for selecting low-power effective signal delivery parameters for an implanted pulse generator. U.S. Pat. No. 6,999,820 (Jordan) proposes a winged electrode body for spinal cord stimulation. U.S. Pat. No. 8,2224,453 (De Ridder) and pre-grant publication US 2005/0055065 A1 discuss spinal cord stimulation to treat pain.

Other previous publications include U.S. Pat. No. 4,633,889 (Talalla), U.S. Pat. No. 7,107,104 (Keravel), U.S. Pat. No. 7,333,857 (Campbell), U.S. Pat. No. 7,697,995 (Cross), U.S. Pat. No. 7,962,218 (Balzer), U.S. Pat. No. 8,346,366 (Arle), U.S. Pat. No. 9,179,875 (Hua), U.S. Pat. No. 9,386,934 (Parker), U.S. Pat. No. 10,278,600 (Parker), US 2007/0010862 A1 (Osypka), and U.S. Pat. No. 9,586,039 A1 (Bornzin).

The medical and surgical therapies that are currently in clinical use for treating back pain, movement disorders, spinal cord injury and spasticity are suboptimal. Many patients do not respond to spinal cord stimulation (SCS) using currently available medical devices, have incomplete relief, or respond only temporarily and revert to painful, debilitating or immobile conditions. There are important medical, ethical and economic imperatives for introducing new safe and efficacious means and methods of treatment.

SUMMARY OF THE INVENTION

The electrode device of this invention is configured for implantation into the dura mater (the dural membrane) that surrounds the spinal cord. Placing the device in this location provides direct contact between the electrode and the cerebrospinal fluid (CSF), in close proximity to the spinal cord. The device has an intradural portion and an extradural portion that compresses and seals the dural membrane between them, securing the device in position and preventing leakage of CSF. The device can be powered by an implanted pulse generator that produces a spectrum of signals to interrupt or otherwise attenuate transmission of pain mediating neural signals through the spinal cord. Optionally, the device is configured to sense endogenous nerve activity and/or evoked potentials that occur in response to stimulation. The device can be programmed to respond to such nerve activity by delivering a dose of stimulation, aliquots of stimulation, continuous stimulation, or stimulus pulses in any suitable combination of parameters that include frequency, width, amplitude, duty cycle, polarity, charge balance, chirp and/or burst, with or without DC offset. The stimulation may be delivered automatically without the need for clinical intervention, providing a customized stimulation pattern that depends upon an individual patient's response. The device can be implanted with minimally invasive surgery (MIS), optionally assisted robotically or with reality-based imaging.

This disclosure further provides a laminoplasty plate for stabilizing the electrode device in a patient after implantation by anchoring it to a vertebra.

Certain features of the invention are referred to in the appended claims. Other features are referred to in the description that follows. The features described in this disclosure can be selected for use of a device or system according to this invention in any operable combination.

DRAWINGS

FIGS. 1 and 2 show an exemplary SCS device according to this invention with an intradural assembly 6, a transdural portion 11 and 12, an extradural assembly 7, 8, and 10, and a lock nut 14 that clamps the intradural assembly and the extradural assembly across the dura 18 of the spinal cord.

FIG. 3 shows a positioning tool for surgically implanting the SCS device across the dura of the spinal cord, physically coupled to the device (below).

FIG. 4 shows a detail of the lower portion 5, 9 of the positioning tool coupled to the extradural assembly 7, 8, and 10 of the SCS device.

FIG. 5A (side view) and 5B (rostral-caudal view) show close-ups of a mechanical stabilization means for securing the extradural elements of the implant within the patient.

FIG. 6 shows the T-shaped geometry of an exemplary intradural electrode array, 20, which is mounted on the distal side of the intradural compression plate 6.

FIG. 7 shows a combined stimulation system for achieving extended coverage of the spinal cord, with improved targeting of critical structures and avoidance of non-targeted structures. The intradural array 20 is shown in place inside of the dura mater 18 suspended by the means of the invention over the spinal cord 20. The device is configured to provide intradural stimulation by way of electrodes on the intradural assembly 5. Concurrently or in alternation, the device can also provide extradural stimulation by way of electrodes located on the base plate 10 of the extradural assembly and facing outwards.

FIGS. 8A, 8B, 9, and 10 show suitable dimensions for the positioning tool, the extradural assembly, and the intradural assembly, respectively.

FIGS. 11A, 11B, and 11C show another SCS device according to this invention with an intradural assembly 11, a transdural portion 31, and an extradural assembly 21. The intradural assembly has flanges 15 that are deployable under the dura. The flanges clamp against the clamping surface 23 of the extradural gasket 22, thereby securing the device to the dura and stabilizing it for long-term use.

Figure 16A:
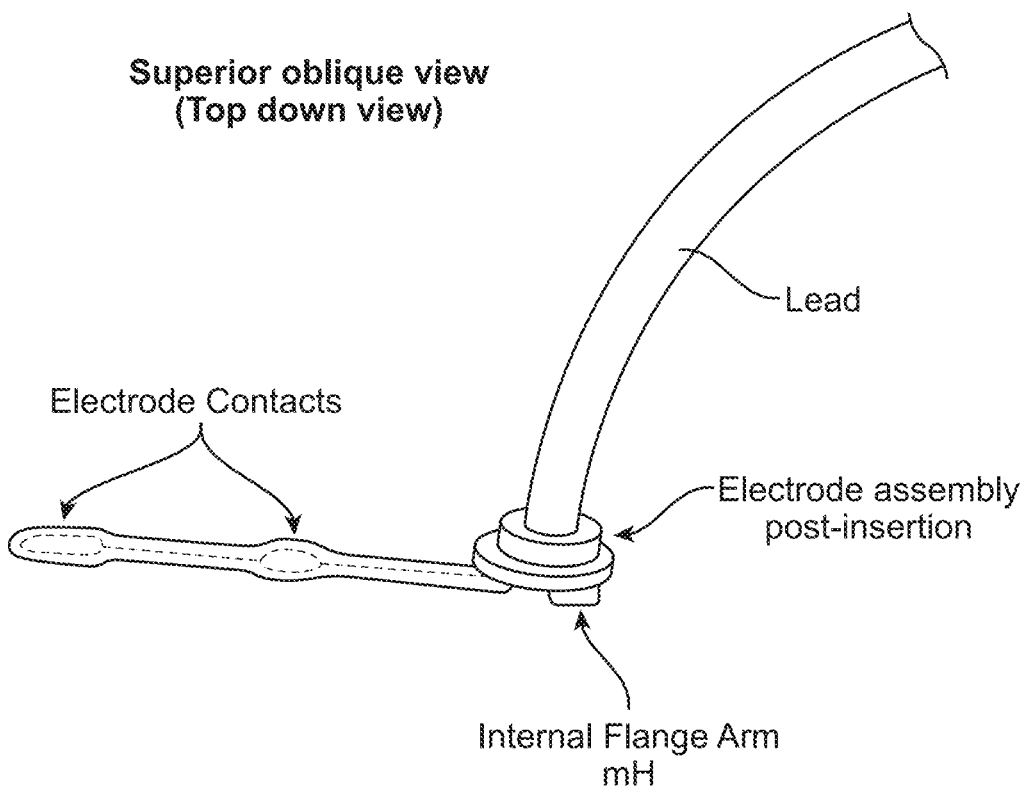
Figure 16B:
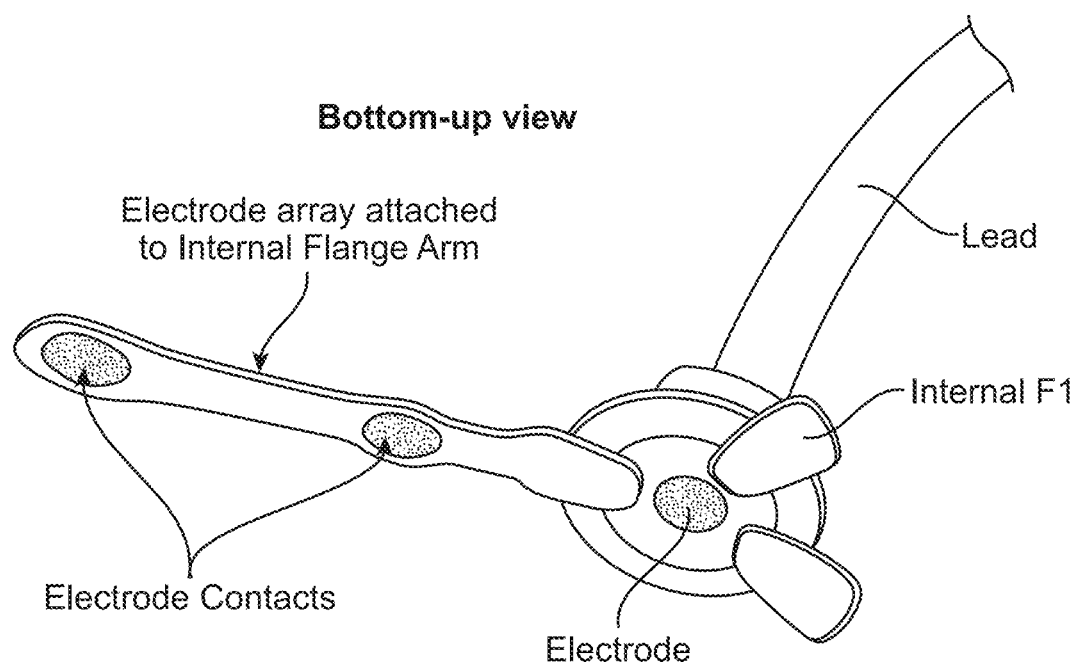

FIGS. 16A and 16B show an SCS device according to this invention with a long flange arm 15b having a linear array of electrodes 14a, 14b and 14c.

Figure 17A:
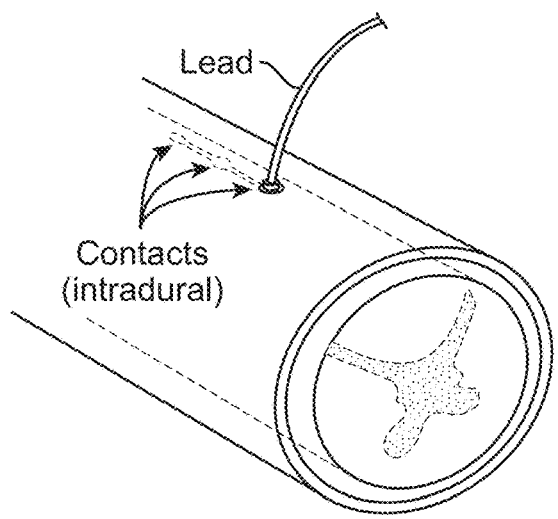
Figure 17B:
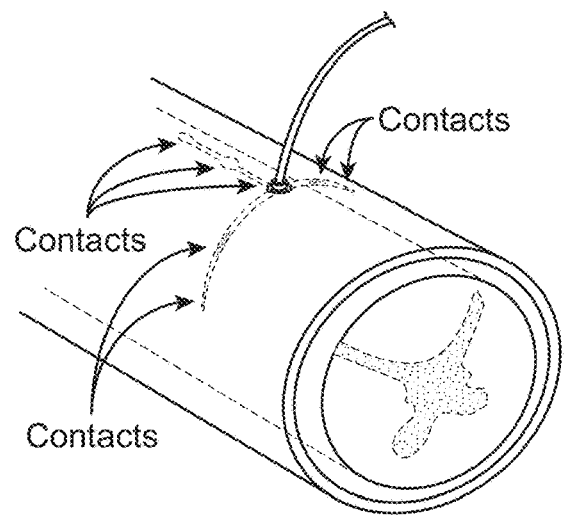
Figure 17C:
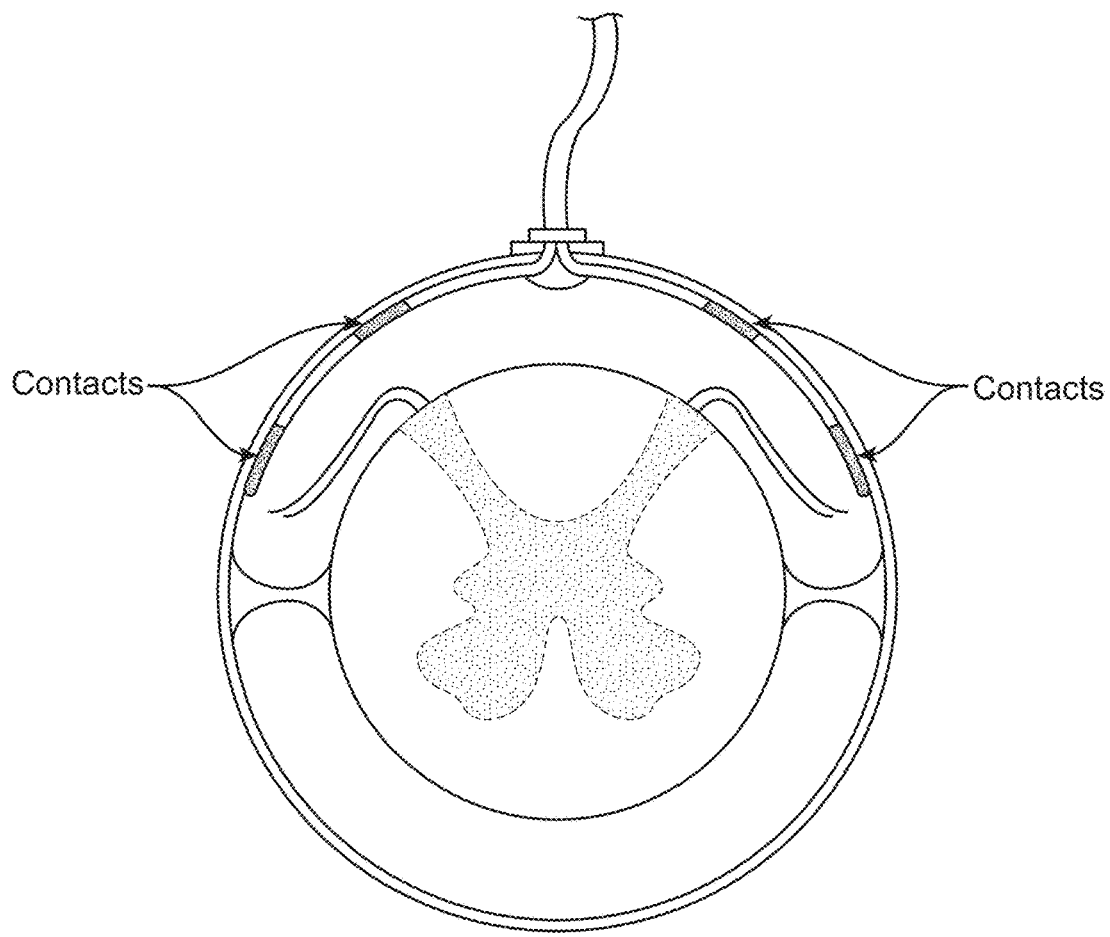

FIGS. 17A to 17C show a device with three long flange arms providing a two-dimensional array of seven electrodes.

Figure 18C:
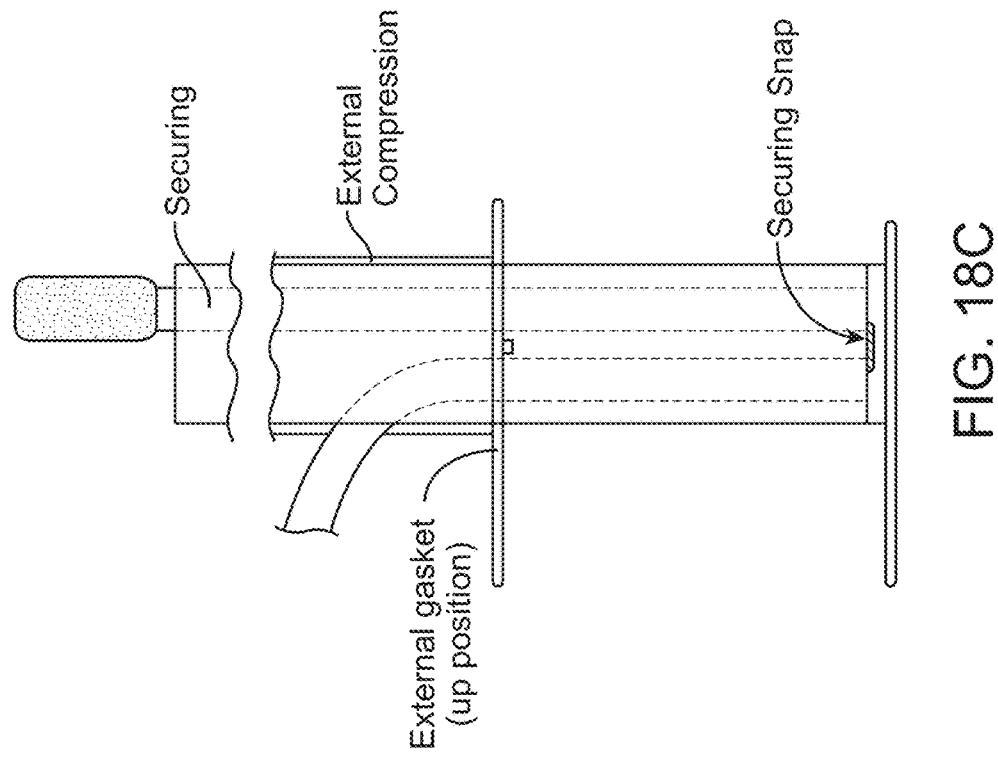
Figure 18A:
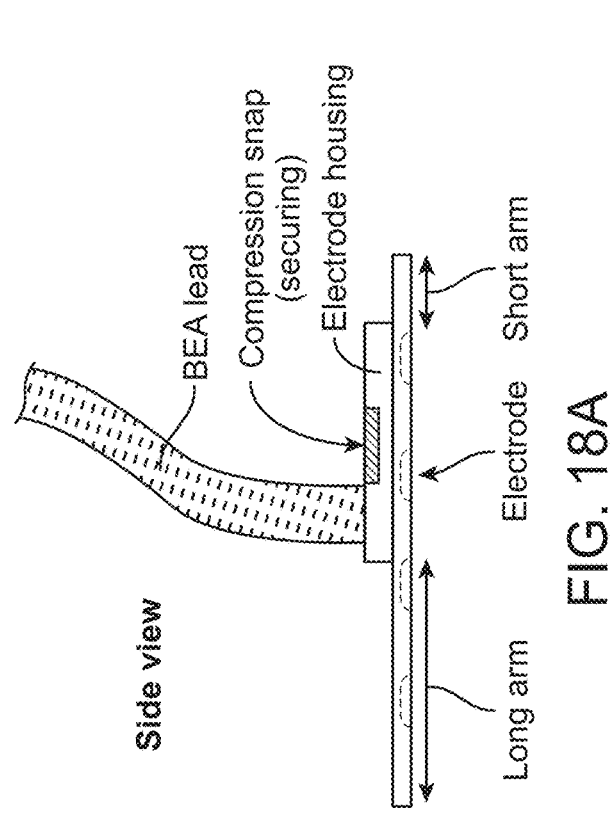
Figure 18B:
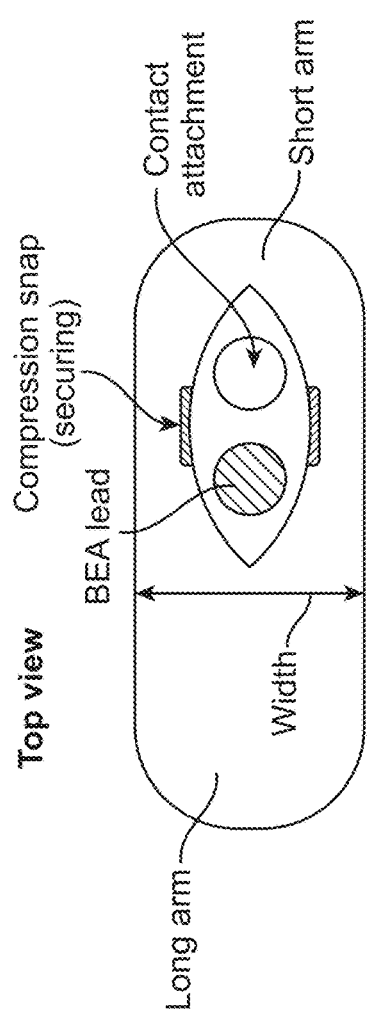

FIGS. 18A, 18B, and 18C show an SCS device according to this invention with an oblong shaped intradural and extradural assembly, designed to clamp together so as to seal the incision used to insert the intradural assembly through the dura.

FIGS. 19A to 19D and FIGS. 20A to 20D provide a procedure for inserting and securing the oblong shaped device to the dura.

FIGS. 21A, 21B, 22A, 22B, 23A and 23B show another SCS device according to this invention with an intradural assembly 11 shaped as an open circle to facilitate insertion through a narrow incision in the dura. The extradural assembly 22 is round, presenting a complementary clamping surface.

Figure 24:
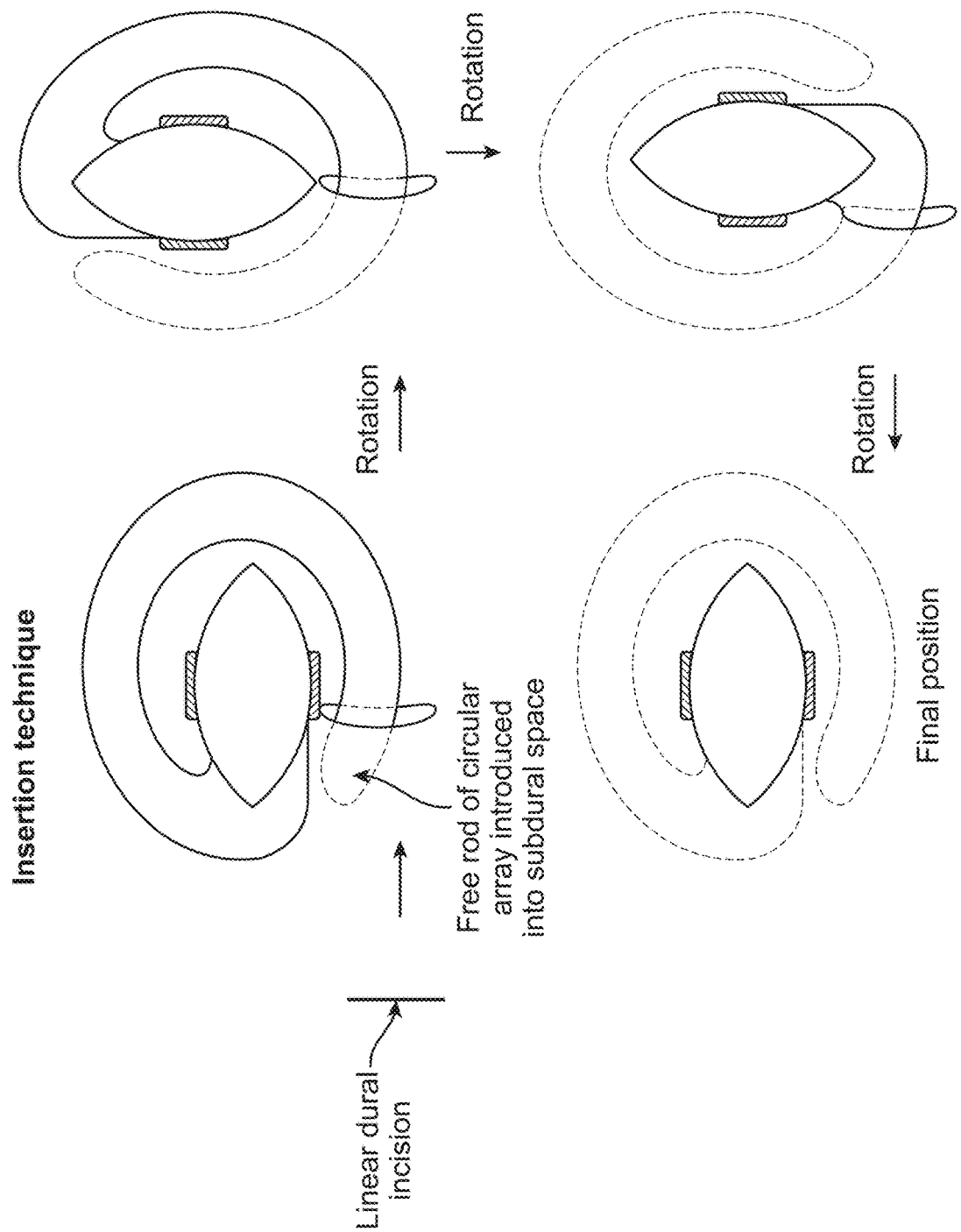

FIG. 24 shows insertion of this device through a very narrow incision.

FIG. 25 and FIGS. 26A to 26F depict the surgical procedure whereby the spinal cord of a subject is exposed and an SCS device according to this invention is inserted through an incision in the dura and secured in position for SCS treatment.

FIGS. 27A to 27F illustrate an electrical simulation device of this disclosure that is designed to function as a port. The device includes one or more openings that are fluidically connected to the CSF and the extradural space, thus allowing for the transfer of liquid from the extradural space to the CSF.

Figure 28:
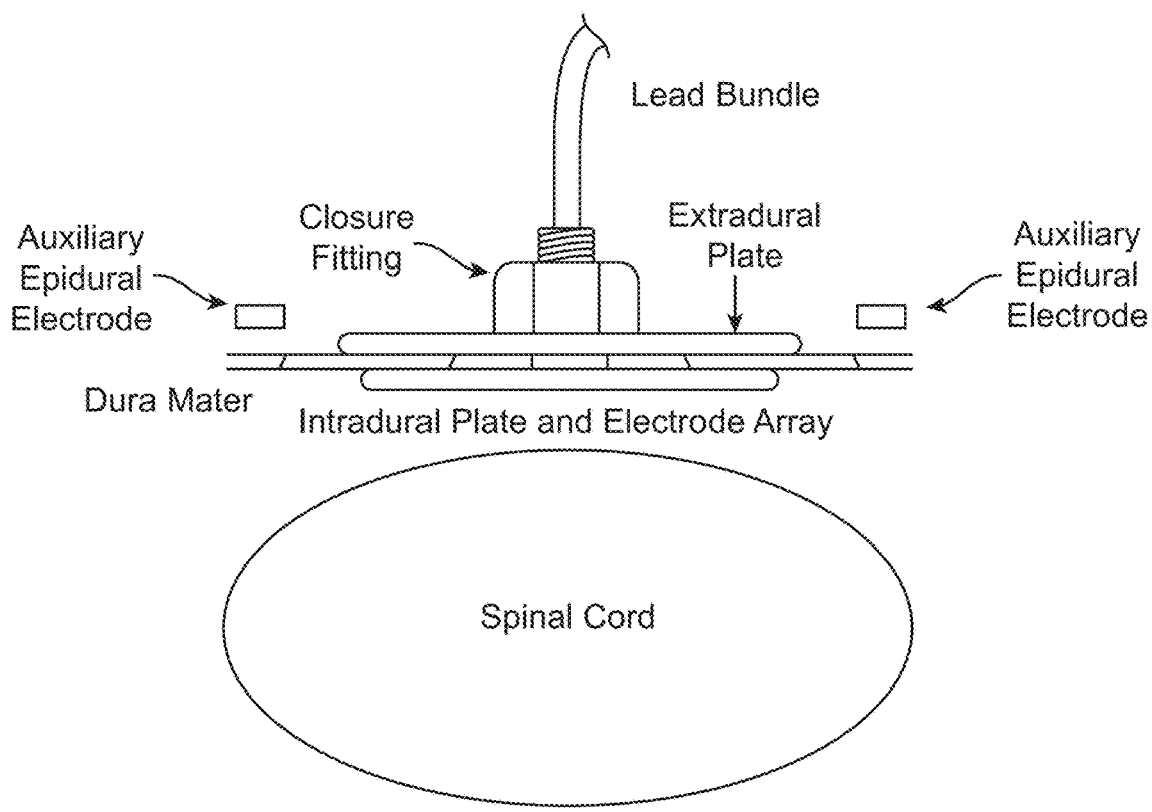

FIG. 28 shows a schematic diagram of the intradural stimulation system with auxiliary epidural lead(s).

Figures 29A, 29B:
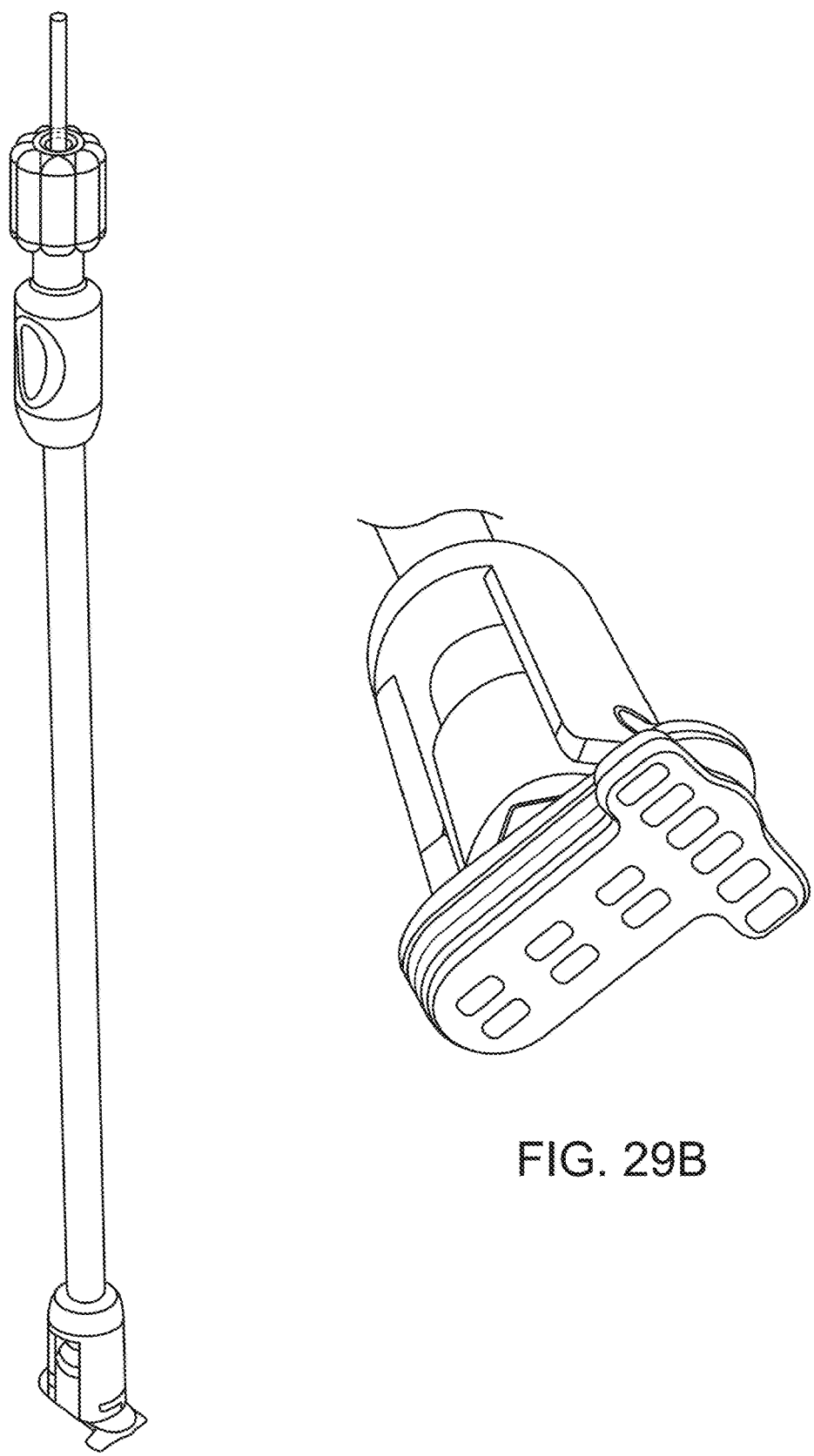

FIGS. 29A and 29B are three-dimensional renderings respectively of prototypes of the intradural stimulator implantation tool, and the T-shaped intradural electrode array on the distal end of the implantation tool prior to insertion.

Figure 30:
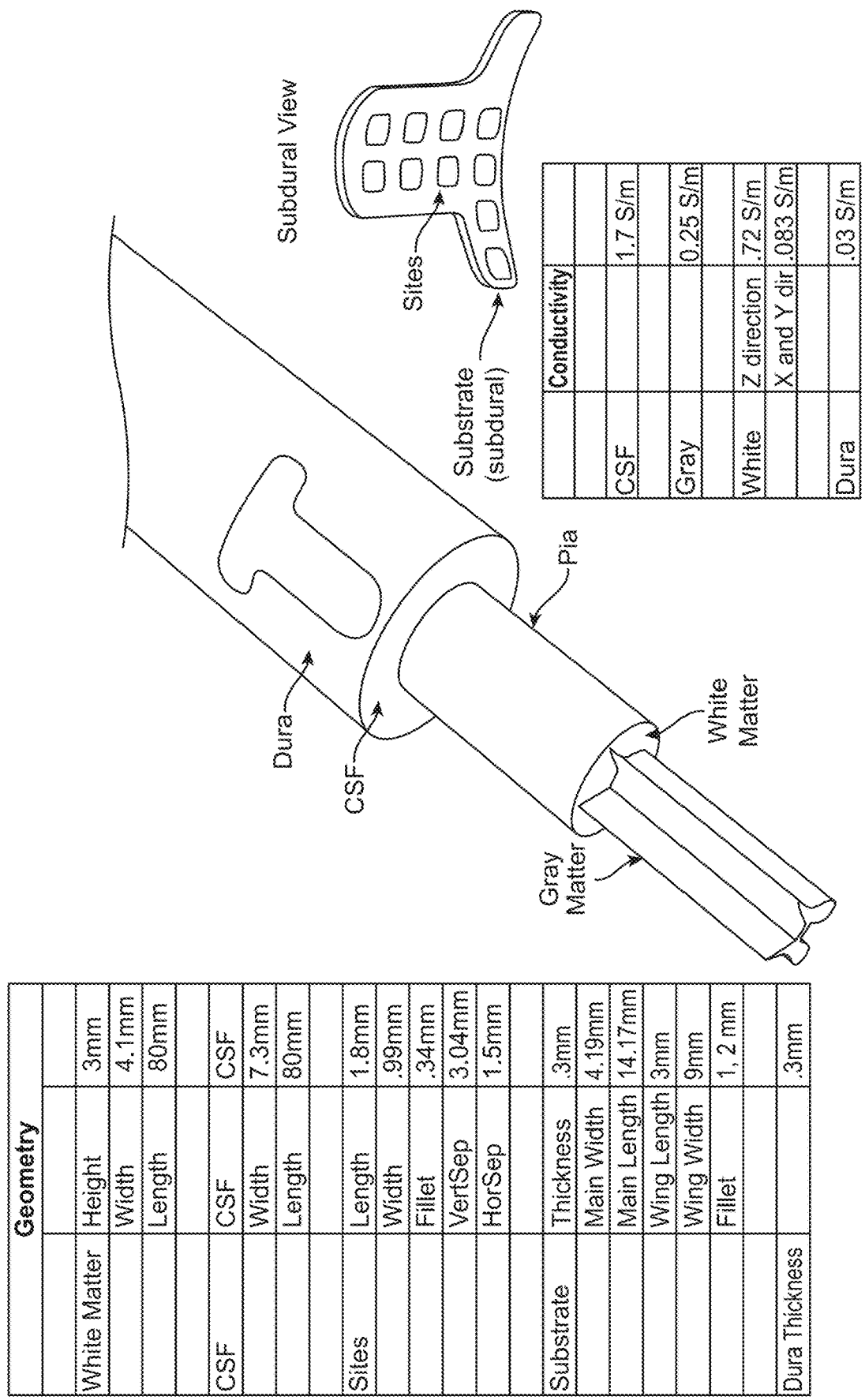

FIG. 30 shows the geometric configuration and electrical parameters of the spinal cord and T-shaped electrode array used in the modeling study described in Example 2, below.

Figure 31A:
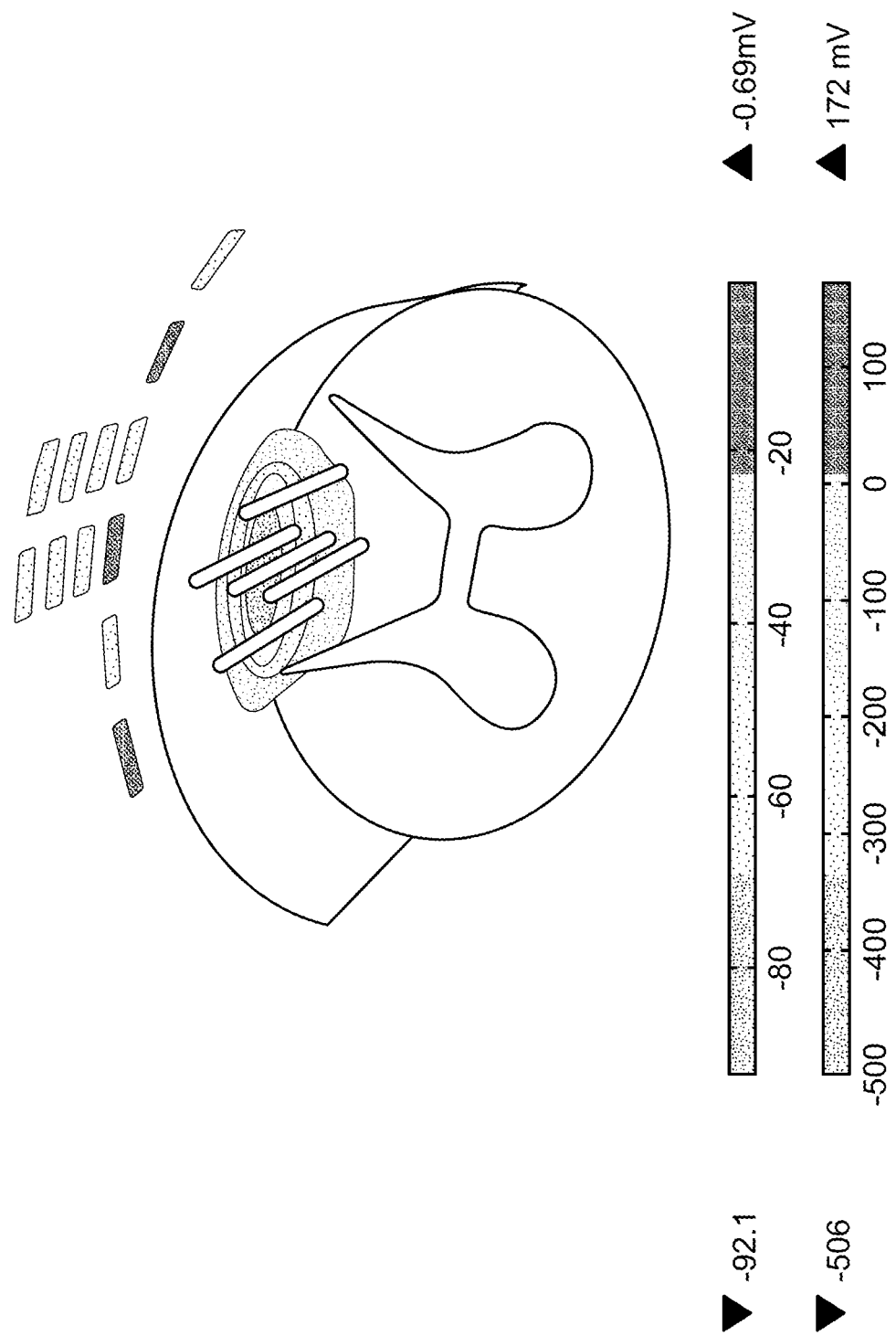

FIG. 31A is a representation of the pia covering of the white matter when viewed from below as a cross section across the white matter and the gray matter of the spinal cord. The electrical potentials resulting from a current drive on the six electrodes on the cross of the T-Array located within the intradural space are shown for the electrode sites themselves (lower scale) and as projected on the pial surface and the white matter cross section (upper scale). The maximum and minimum voltages of those potentials in this example are shown on the right and left sides of the scales in each case, respectively. The five lines drawn through the white matter indicate locations where the intraparenchymal voltage is sampled.

Figure 31B:
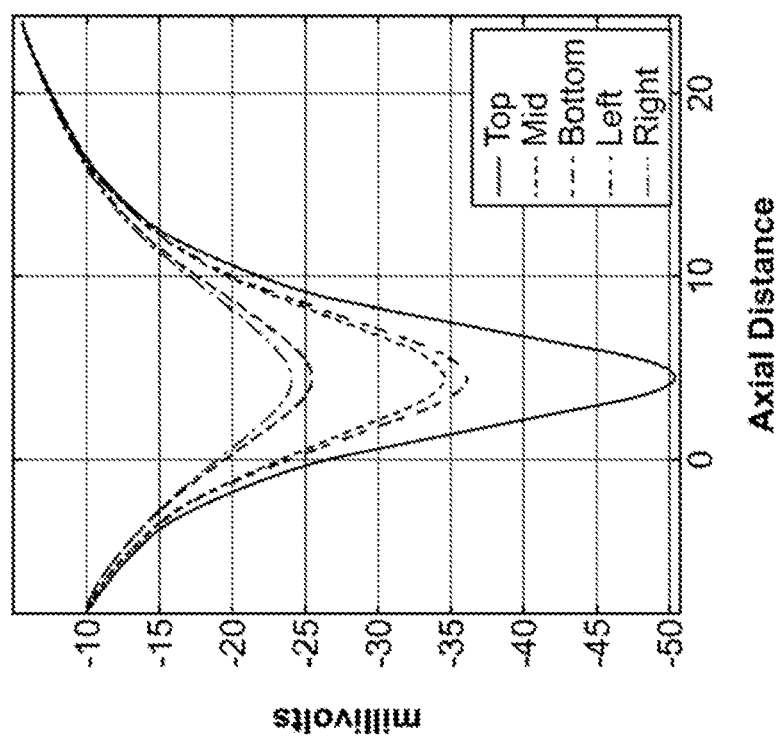

FIG. 31B is a graph of the stimulation potentials in millivolts vs axial distance along the spinal cord, along the locations of the five positional sampling lines shown in FIG. 31A. These electrical potentials are produced by the currents driven from the 6 electrodes on the cross of the intradural T-array shown in FIG. 31A, which is positioned such that the electrode surfaces project approximately 0.3 mm below the underside of the dura. The negative peaking of these spatial waveforms indicates a positive second spatial derivative or difference surrounded by a lesser negative spatial second derivative. These are examples of computational results produced by the finite-element modeling of intradural spinal cord stimulation.

Figure 32:
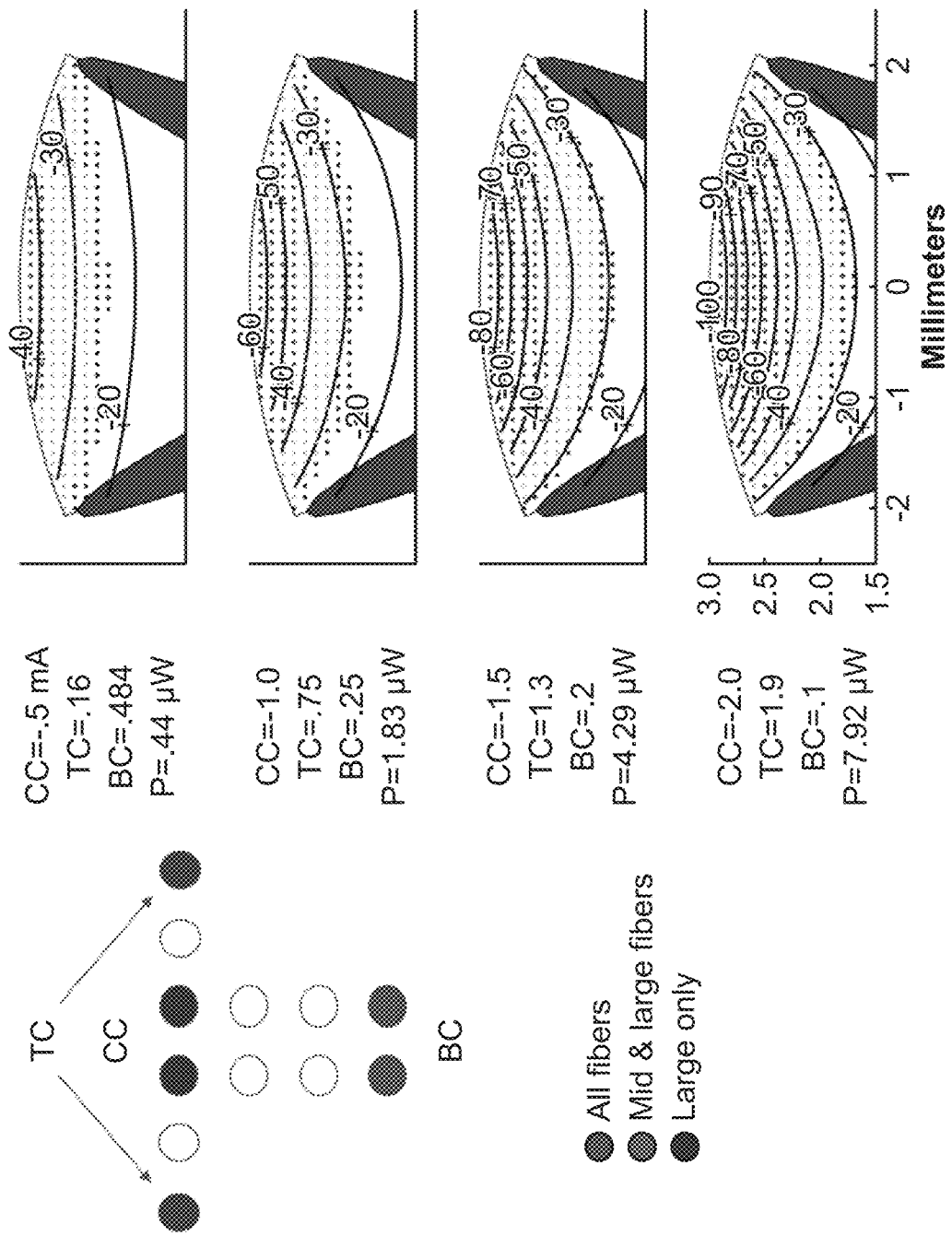

FIG. 32 provides computational results produced by the finite-element modeling of intradural spinal cord stimulation. The top of the left side shows the T-shaped arrangement of the 12 electrodes of the intradural array. TC indicates the "tip" electrodes on the cross of the T. Likewise, CC indicates the "center" electrodes on the cross of the T, while BC indicates the "bottom" electrodes on the vertical component of the T. The left side shows the gray-scale ranges of size of the neural fibers excited within the white matter. The right side shows the four examples of the curved isopotentials lines, with the strength of each one labeled in mV, produced by the stimulation parameters the sizes of which for each case are shown just to the left of each plot. These stimulation parameters are the currents driven from the TC, CC and BC sites, and the resulting power dissipations. The plots show the depth vs. lateral location (both in mm) of the isopotentials lines, and reveal that their shapes are confined to the regions of white matter located within the boundaries of the dorsal horn gray matter. The gray-scale dots between the isopotentials show the locations in the white matter where fibers of different sizes are excited, per the gray-scale range of sizes shown at the bottom of the left side. These examples show exquisite control of the depth of stimulation within the white matter, with minimal to no stimulation of the non-targeted gray matter.

Figure 33:
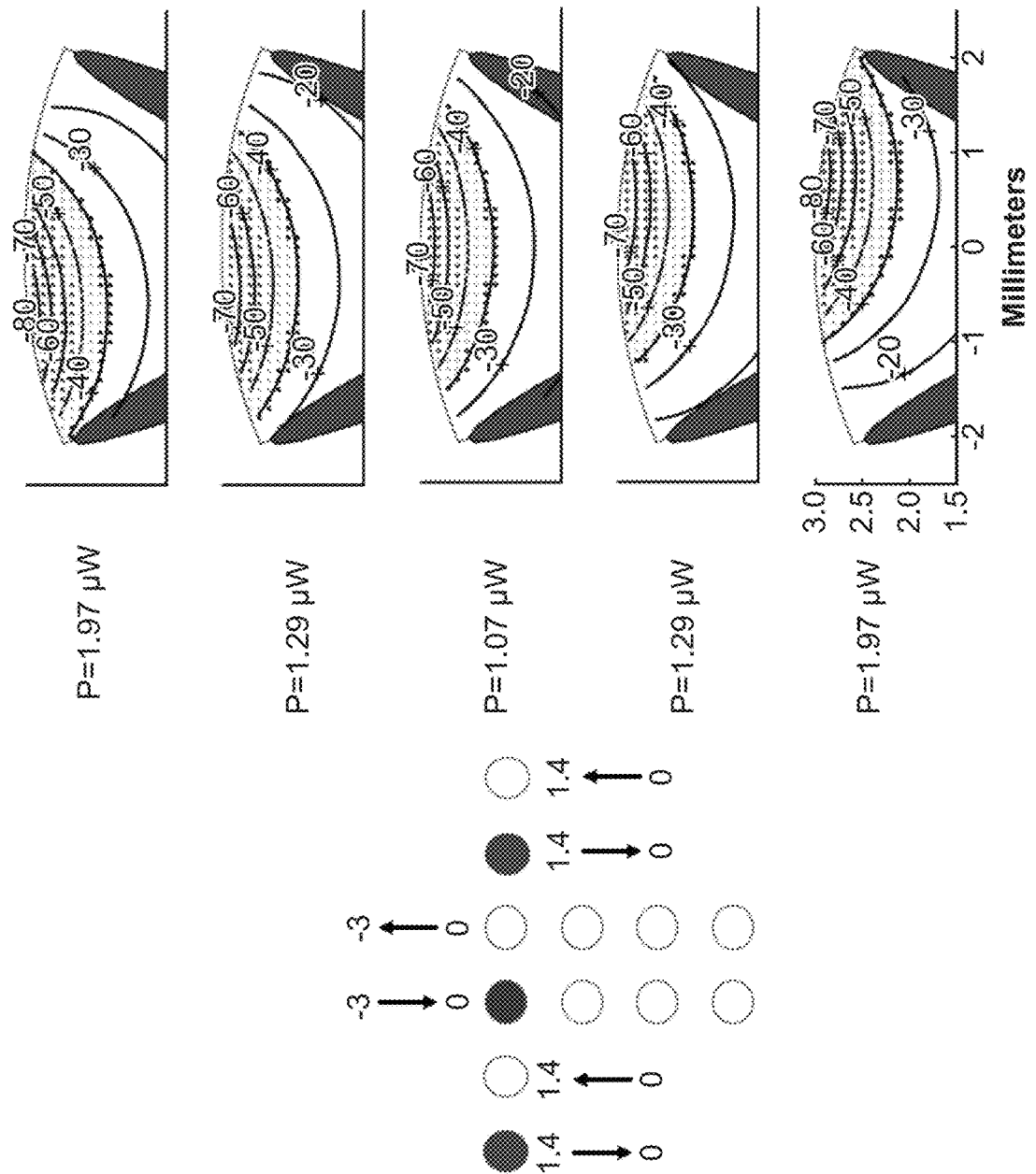

FIG. 33 provides computational results produced by the finite-element modeling of intradural spinal cord stimulation. The top of the left side shows the electrodes of the T-array and presents an example of variations in the currents driven by those electrodes on the cross of the T. The currents of the center two electrodes are varied between 0 and −3 mA, while those of the other four electrodes are simultaneously varied between 0 and 1.4 mA. The arrows indicate the directions of current change, from positive to negative or vise-versa, for the purposes of this example. The right shows plots of the isopotentials lines, with the strength of each one labeled in mV, and their locations within the white matter as the example currents of the electrodes are varied through their ranges from one extreme to the other, in five equal steps. The gray-scale ranges of size of the neural fibers excited within the white matter are the same as those defined in FIG. 32. The resulting power dissipations in each of the five cases, in μW, are shown adjacent to each plot. The plots show the depth vs. lateral location (both in mm) of the isopotentials lines, and reveal that their circumferential stimulation pattern can be controlled in an essentially linear manner within the white matter inside the boundaries of the dorsal horn gray matter. These examples show exquisite control of the circumferential progression of stimulation within the white matter, with minimal to no stimulation of the non-targeted gray matter.

Figure 34B:
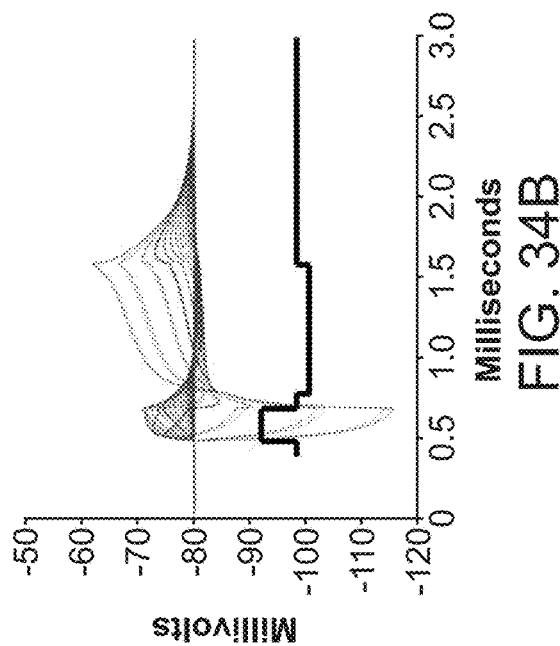
Figure 34C:
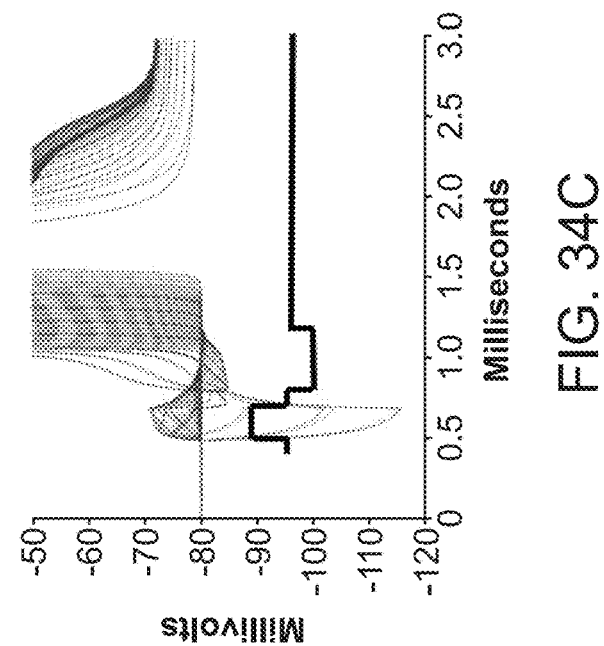
Figure 34A:
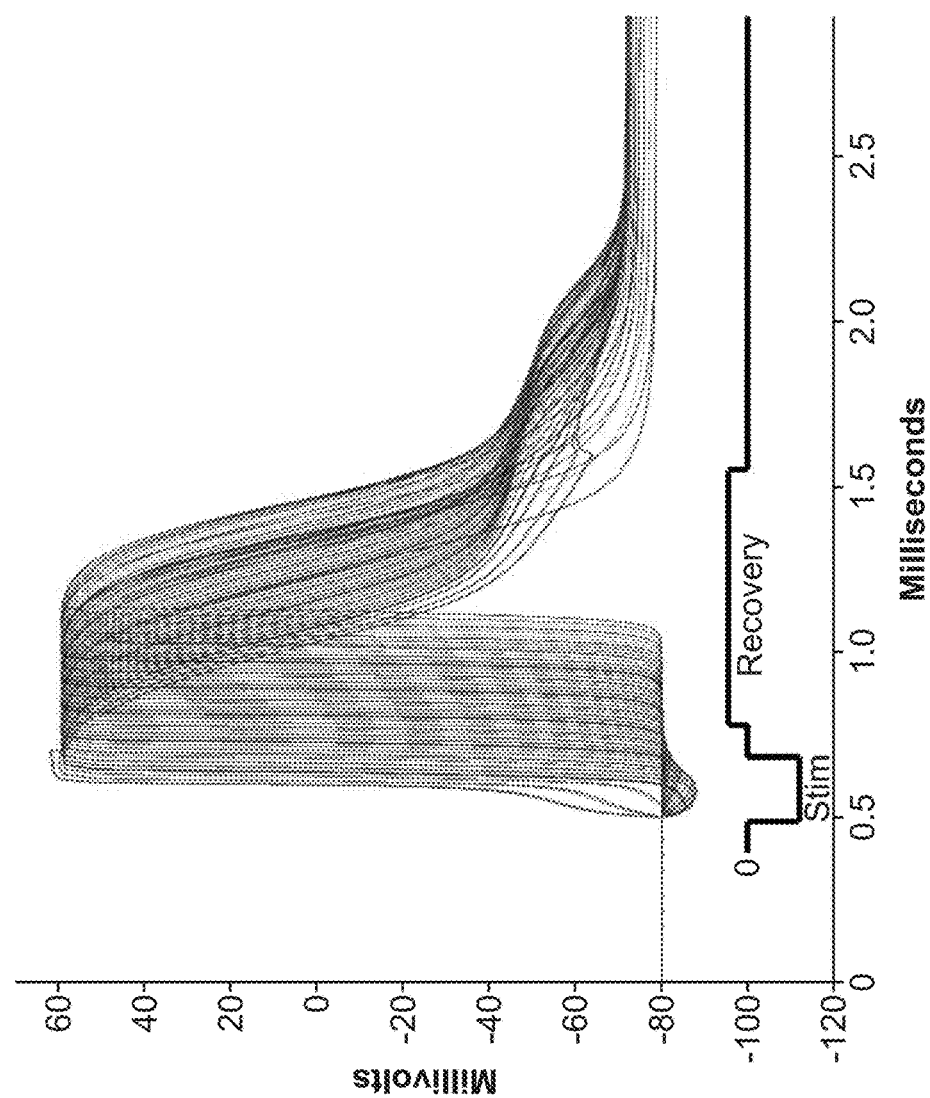

FIG. 34A is a plot in millivolts versus milliseconds of an example of the ensemble of action potentials produced at nodes of the neurons targeted by stimulation pulses from the intradural electrode array. In the trace under the plot, the "stim" segment in this example case constitutes an ≈200 μs cathodic depolarizing component of the phase, while the "recovery" segment constitutes an ≈750 μs anodic component of the phase. The individual action potentials occur over the range of times indicated, as governed by the electrophysiology of the neurons.

FIG. 34B is a plot in millivolts versus milliseconds of a variant stimulation in which the central electrodes of the T-Array deliver an anodic first component of ≈200 μs, to demonstrate the ability to achieve the focusing effect needed to avoid stimulation of off-target tissue. It constitutes an example of a well-designed pulse that does not induce an off-target action potential, as indicated by the low amplitudes of the peaks in the recovery portion of the phase, and hence no stimulation of off-target neurons. FIG. 34C is a plot in millivolts versus milliseconds, which demonstrates that if the recovery (cathodic) segment that follows the anodic first segment has the same pulse area but is larger in amplitude, then unintended discharge and propagation is possible in non-targeted tissues, as indicated by the high-amplitude action potentials that occur after the recovery component of the phase. These are further examples of computational results produced by the finite-element modeling of intradural spinal cord stimulation.

FIG. 35A is a plot of millivolts versus time in milliseconds of the stimulation driving voltage and the average interface voltage at the site of a circular electrode having an area of ≈1.8 mm$^2$ and driven with a 200 μs cathodic pulse of 2 mA followed by a 50 μs pause and a 400 μs charge balance phase of 1 mA. The drive and the interface voltages show a step at the beginning of the pulse followed by ramping down until the end of the cathodic pulse. The average interface voltage increases because the current distribution later in the pulse is less efficient. The difference between the drive voltage and the interface voltage is accounted for by the charge accumulated on the surface of the electrode site and the difference in current distribution as the phase progresses.

FIG. 35B is a plot of the distribution of the interface current in mA versus radial distance across the electrode site in mm, from just before the start of the cathodic pulse to just before its end. At the beginning of the pulse, the current at the edge of the site (i.e., at radial distances of 0.7 to 0.8 mm) spikes to a level well above that of the electrode's center. As time passes, this current distribution will become more uniform. FIG. 35C is a plot of the distribution of the interface voltage in mV versus the radial distance across the electrode site in mm for the same times as in FIG. 35B. This negative potential is seen to increase in magnitude but also is lower at the edges due to the accumulated charge.

Figure 36:
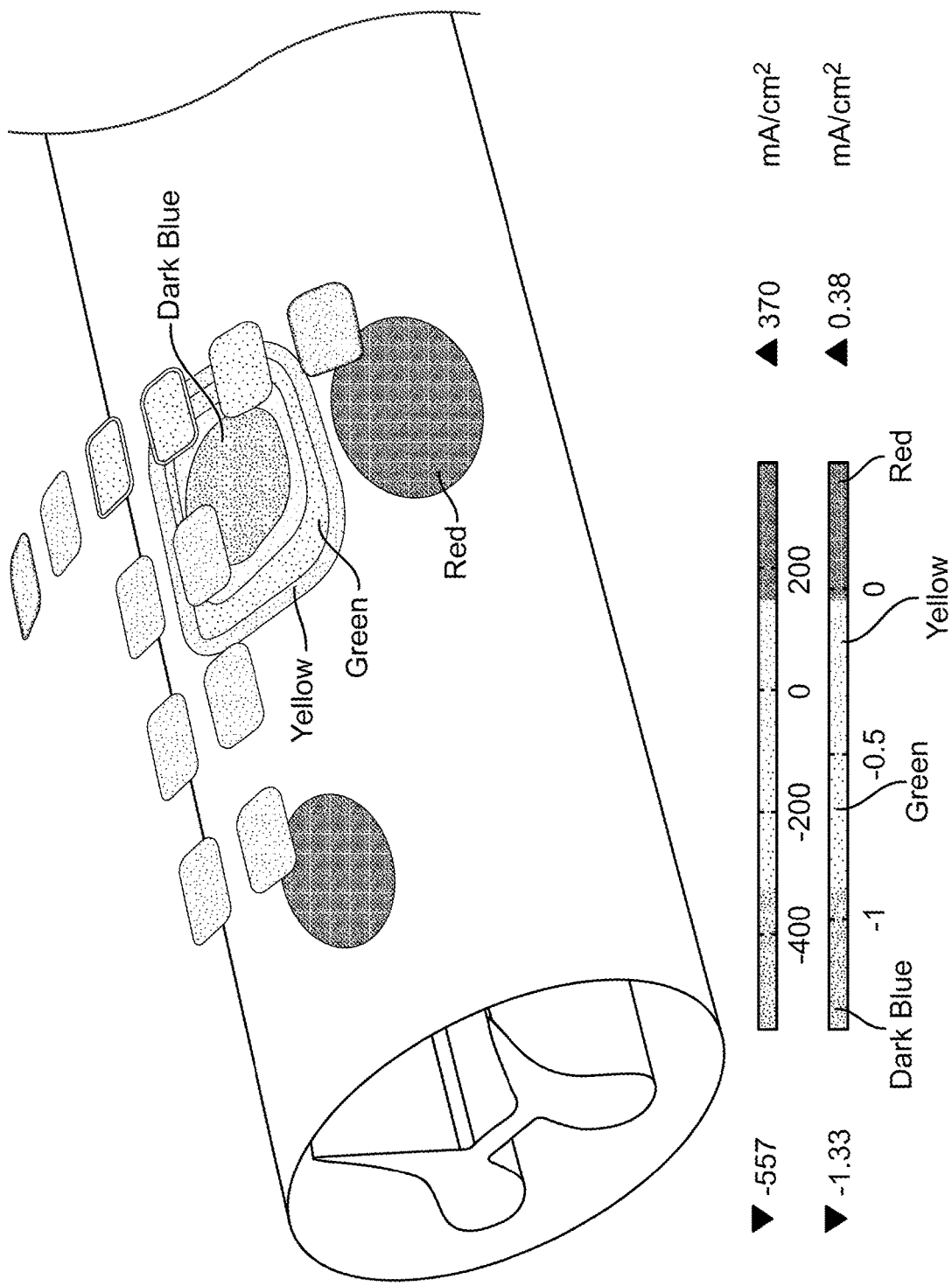

FIG. 36 is a drawing of a spatial model of the spinal cord showing the current distributions on the electrode sites and the pial surface of the white matter at the instant that a cathodic stimulation phase of ≈200 μs is started. The current densities on the electrode site edges (upper scale bar) are very large with respect to the average current but this quickly disappears as the charging of the site progresses. The current passing in and out of the white matter (lower scale bar) is much less than the current at the electrode sites because of the shunting effect of the cerebrospinal fluid. In this example, the total current at the cathodic sites sums to 4 mA, while the total current passing into the white matter is only 0.13 mA or 3.25%. The maximum and minimum values of the current densities are indicated on the right and left sides of the scales bars, respectively.

Figure 37A:
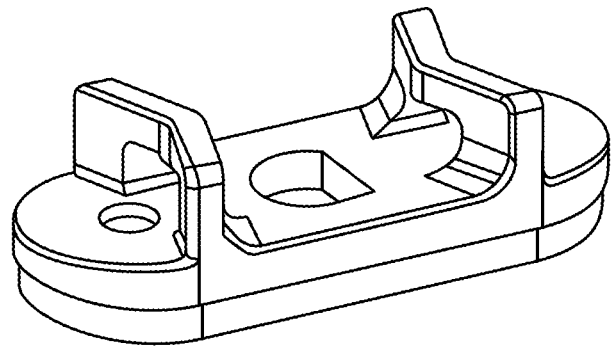
Figure 37B:
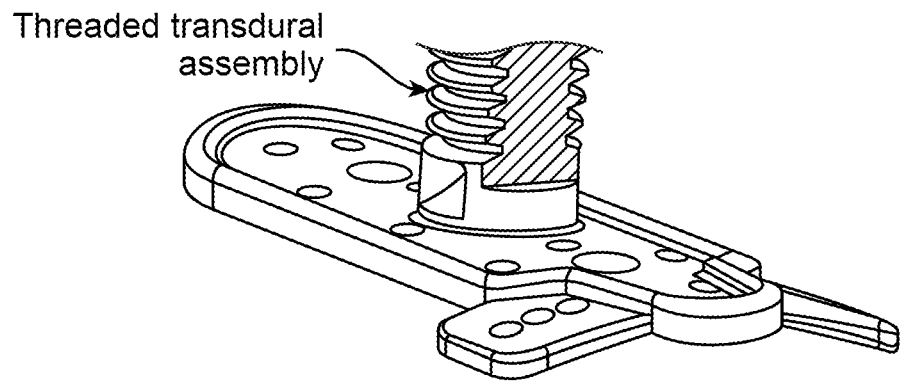
Figure 37C:
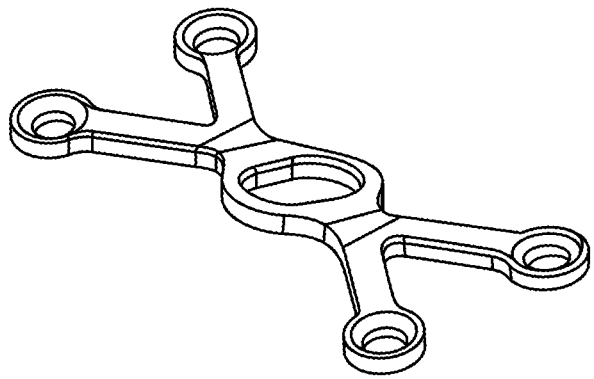

FIGS. 37A, 37B, and 37C together constitute an exploded view of certain components of an electrode device currently in use. The intradural assembly with affixed transdural component is inserted into an incision in the dura, and capped from the outside with the extradural assembly to re-seal the dura, and the laminoplasty or stabilizing plate is secured in position above the extradural assembly.

Figure 38:
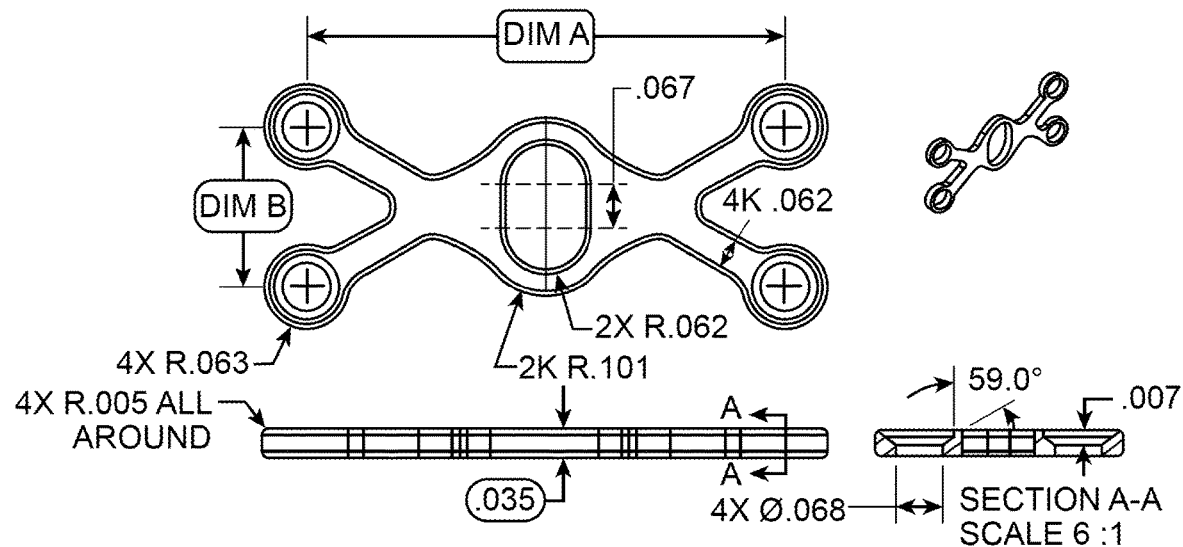

FIG. 38 shows manufacturing criteria for the stabilizing plate.

Figure 39:
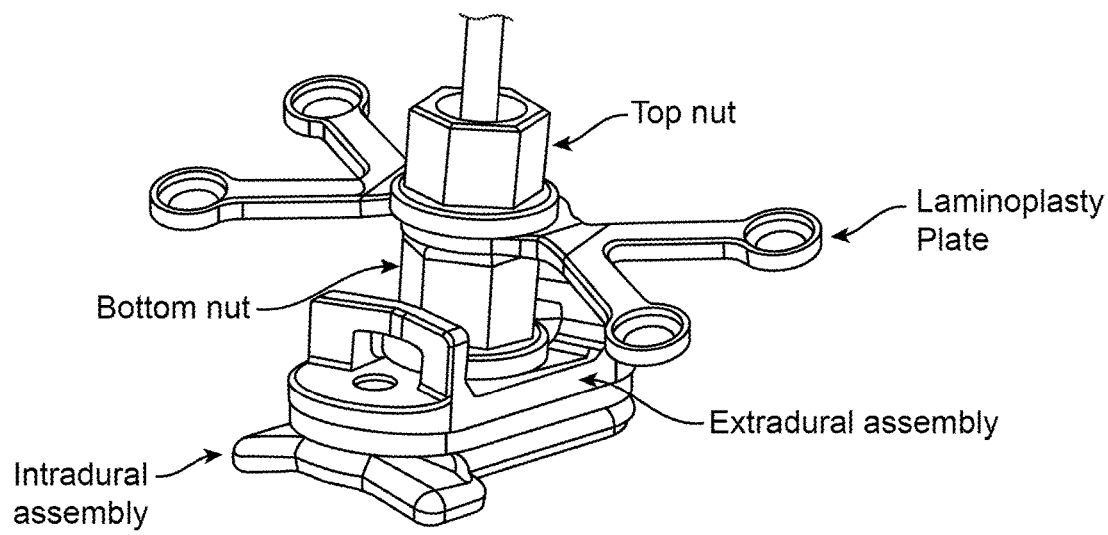

FIG. 39 depicts an exemplary entire electrode device assembled with the laminoplasty plate in place.

Figure 40:
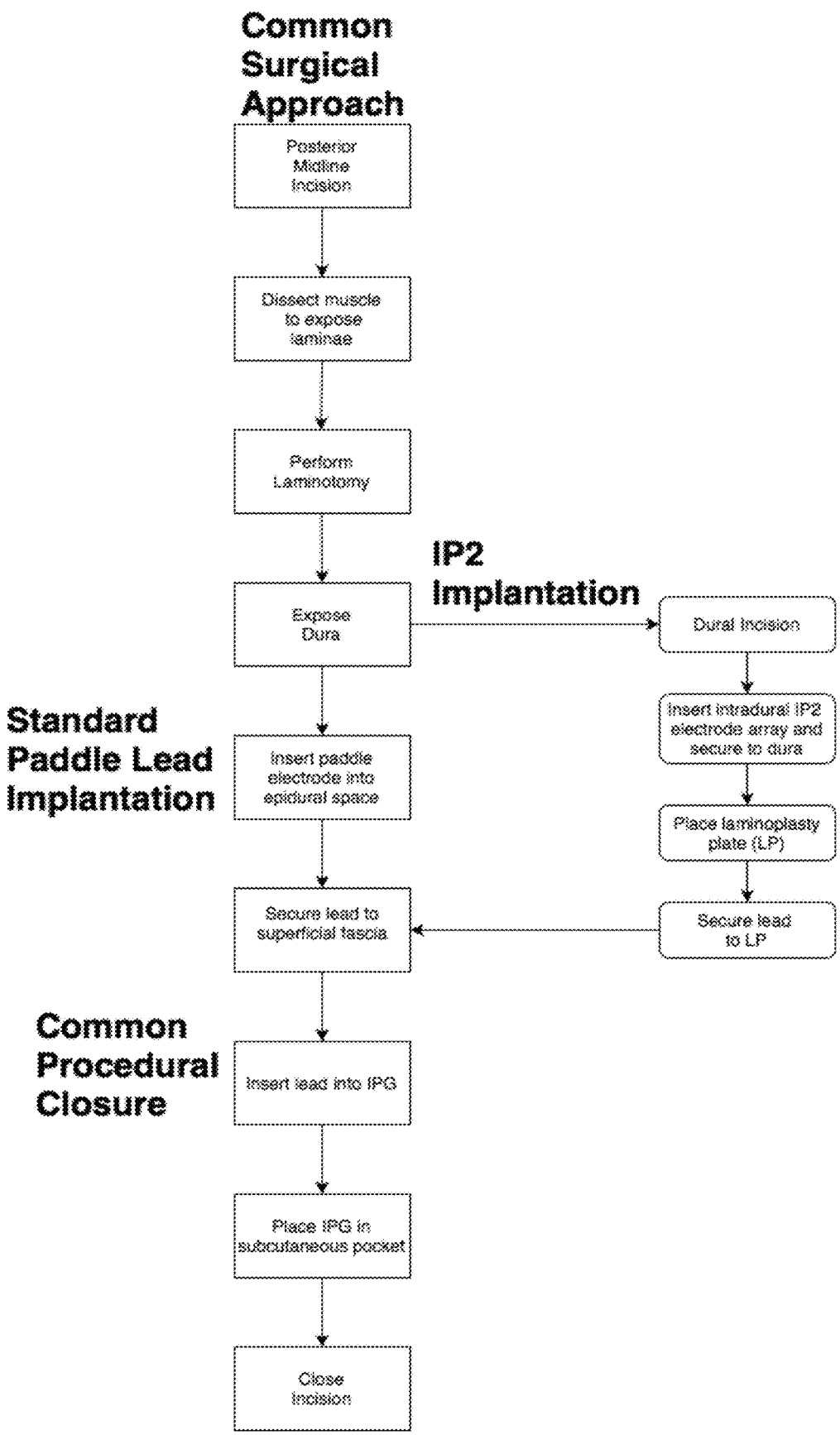

FIG. 40 is a flow chart comparing the implantation procedure of an electrode array (IP2), compared with paddle lead implantation as commonly practiced in spinal cord surgery.

Figure 41:
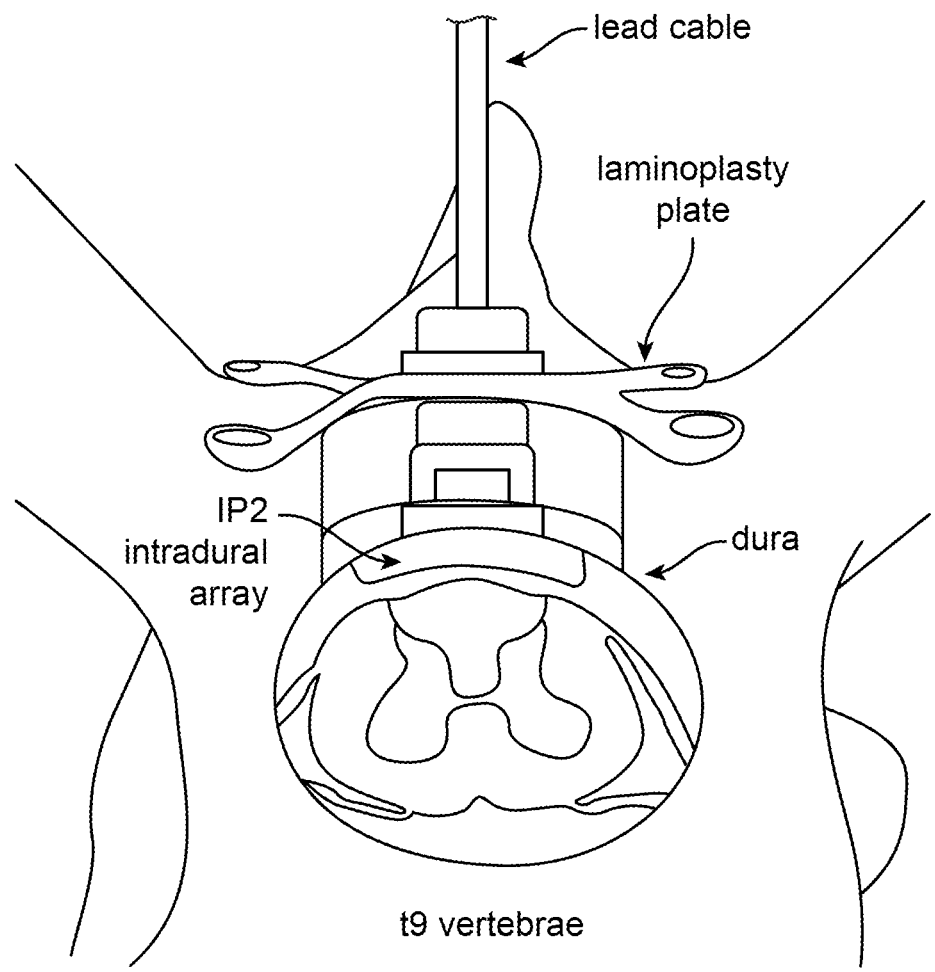

FIG. 41 depicts the exemplary electrode device in the context of the tissues into which it is implanted. The laminoplasty or stabilizing plate maintains the electrode array in a fixed position relative to the adjacent spinal lamina, thereby stabilizing the implant against displacing forces that are generated during normal movement.

DETAILED DESCRIPTION

This invention provides a new technology for management of pain and other conditions by stimulating the spinal cord in a manner that disrupts, interferes with and/or inhibits transmission of deleterious or undesirable sensory input. The stimulus alleviates symptoms and signs of pain, while inhibiting or minimizing the risk of side effects such as paresthesia, and potentially minimizing any side effects on essential neurological processes such as motor neuron transmission and proprioception.

The technology provided in this disclosure can be used for spinal cord stimulation (SCS) of any kind that is of benefit to the patient. The devices are suited for the purpose of administering SCS at low frequencies, as well as at high frequencies. As described herein the devices can be configured to sense action potentials and deliver customized doses of stimulation in a closed loop fashion. The size and ease of implantation of the disclosed devices allow the devices to be used in a variety of therapeutic applications. These features allow for multiple implants to be made in an individual patient, each potentially comprising electrode arrays with a variety of configurations. Any of the devices described or claimed below may be configured for placement inside dura such that the electrodes are in direct contact with the CSF but not in direct contact with the spinal cord itself One of the advantages associated with high frequency stimulation is that patients typically do not experience paresthesia. When using high frequency SCS, the specific location of the stimulating electrode within the extradural space of the dorsal spinal canal may be less important in its impact on clinical efficacy. This differs significantly from standard SCS methods and devices where the location of electrodes within the extradural space is critically important because of the need to focus or aim the current. A significant limitation of the standard SCS methods is that the unintended movement of the implanted epidural lead, due for instance to a failure of the anchoring mechanism, typically results in decreased or no subsequent clinical efficacy of the stimulation.

Advantages of the devices and methods described herein include the ability to provide stimulation through direct contact with the CSF which avoids problems caused by providing stimulation in the extradural space. For example, in order to provide and effective amount of stimulation to the spinal cord from the extradural space a sufficiently strong current must be used and in some instances such a current can cause undesirable off target stimulation. As described herein the devices and methods can deliver either high frequency for example from about 2-10 kHz, or lower frequency stimulation, for example less than 2 kHz, less than 1 kHz, or less than 500 Hz, to the CSF.

The invention described and claimed here overcomes many of the limitations of epidurally placed electrodes by making it possible to stimulate neural structures deep within the spinal cord at particular target locations, and without stimulating non-targeted structures such as the dorsal rootlets.

Other Benefits of the Invention

A drawback of SCS systems that are now available commercially is the need for frequent battery recharges because of the high power demands. This limits both their use and their effectiveness. We believe that a major factor contributing to this large power demand is that stimuli delivered from the extradural space must pass through the resistive barrier of the dura mater in order to drive therapeutic levels of current density through the CSF and into targeted regions of the spinal cord. We estimate that the presence of the dural membrane between the stimulating electrode and the CSF layer increases the power requirements by five- to ten-fold.

The new intradural SCS device described in this disclosure is designed to overcome this limitation by placing one or more SCS electrodes inside of the dura, without substantially increasing the complexity, duration or risks associated with extradural SCS. The devices of this invention can be used by the clinician to place electrodes in stable locations inside the intradural space of the spinal canal, making direct electrical contact with the CSF. Placement of the electrode can be used to control the relative distance from the electrode to the spinal cord itself and that in some applications it is useful to position the electrode from about 0.05-3 mm, or from about 3-8 mm from the surface of the spinal cord.

Depending on the manner of implementation, a major benefit of this approach is a potential reduction in power demand of 5 to 10 fold, or more. This in turn reduces battery recharge requirements, resulting in a much more generous time interval before a battery change is needed. Furthermore, because of the superior electrical coupling between the electrodes to the CSF, and proximity to the spinal cord, improved clinical efficacy is also expected. Additional benefits include a reduced occurrence of off target stimulation, such as undesired simulation of surrounding tissue, such as for example, the dorsal rootlets.

Another benefit of this invention is the ease by which the neurosurgeon may implant the device in the subject at an effective location, minimizing the risk of damage caused by the surgery or operation of the device, thereby enhancing patient safety. The dorsal surface of the spinal canal dura is exposed in a manner similar to what is currently being used to implant SCS devices in the epidural space. After the dura is exposed, the device is placed through an incision in the dura by a minimally invasive surgical (MIS) procedure that takes a matter of just a few minutes. The electrode lead is then connected to a pulse generator which is implanted elsewhere in the patient using the standard surgical approach.

The SCS device of this invention reduces the risk of lead migration, which can be a substantial problem with leads from devices placed outside the dura. Since the electrodes distal to the lead bundle are fixed to the inner wall of the spinal dura mater, they do not drift or move from the vicinity of the anatomical location where they are implanted. The SCS device of this invention also avoids the extradural mass effect caused by large extradural devices, which can constrict the thickness of the CSF filled space, limit the natural flow of CSF, and potentially tether the pial surface of the spinal cord.

Other benefits of the technology of this invention are elaborated elsewhere in the disclosure, and will be apparent to the reader when it is used in the clinic. All of these benefits combine to provide the treated subject with a superior and more focused and durable therapeutic effect.

Technology Platform

In general terms, this invention provides a device for spinal cord stimulation, configured for securing to the dura of the spinal canal of a subject. It includes one or more electrodes and a means for securing the device to the dura such that the electrodes are in direct contact with cerebrospinal fluid within the canal of the spinal cord, but not in direct contact with the spinal cord itself.

The securing means may pass through the dura, clamping the device to the dura. Alternatively or in addition, the device may be secured to another anatomical structure beyond the dura, secured to the inner surface of the dura, or otherwise securely suspending the electrode above the spinal cord in direct electrical contact with the cerebrospinal fluid. Usually the securing means secures the electrode assembly in a desired location with sufficient permanence so that it reliably stays in place, typically on a chronic long-term basis (at least several weeks, months or years).

When the device is configured for traversing and securing to the dura surrounding the spinal cord of a subject, the device may include a transdural portion, an intradural assembly, an extradural assembly, and one or more electrodes on the transdural portion and/or the intradural assembly. To assist in securing the device to the dural membrane, it is generally transformable from an OPEN position to a CLAMPED position. In the open position, the device is inserted through an incision in the dura, placing the intradural portion inside the dura. By clamping the dura between the intradural assembly and the extradural assembly, the device is secured to the dura in a leak-free manner, with the electrodes in direct contact with the cerebrospinal fluid.

In more detail, the transdural portion may include an outside surface and a vertical or longitudinal axis, which is positioned perpendicularly to the surface of the dura after implantation. The intradural assembly typically aligns with and conforms to an internal surface of the dura. It is either affixed or is slidably or rotatably connected to the transdural portion. It has a clamping portion that extends or is extendible to a position that is radially beyond the outside surface of the transdural portion. This means that upon implantation, the clamping portion extends in one or more directions that are perpendicular to the longitudinal axis, either linearly along the anterior posterior axis or curving along the rostral caudal axis so as to conform to the inner surface of the dura, or both, so that the clamping surfaces of the intradural portion are in contact with the inner surface of the dura.

Similarly, the extradural assembly conforms to an external surface of the dura, wherein the extradural assembly is either affixed or is slidably or rotatably connected to the transdural portion. The clamping portion of the extradural assembly extends or is extendible to a position that is radially beyond the outside surface of the transdural portion. This means that upon implantation, the clamping portion extends in one or more directions that are perpendicular to the longitudinal axis, either linearly along the anterior posterior axis or curving along the rostral caudal axis so as to conform to the outer surface of the dura, or both, so that the clamping surface(s) of the extradural portion are in contact with the outer surface of the dura. In addition, there are one or more electrodes included in the transdural portion, in the intradural assembly, or in a combination thereof.

So that the intradural assembly and the extradural assembly can be caused to close together, one or both can include an aperture that is complementary to and encompasses the outside surface of the transdural portion. This configures the respective assembly to slide over or around the outside surface of the transdural portion such that the spacing between the intradural and extradural assemblies can be narrowed from an open position to a clamped position. In general, the intradural assembly is configured to pass through a short incision in the dura surrounding the spinal cord when the device is in the open position, leaving the extradural assembly outside the dura, whereafter sliding or rotating the extradural assembly and/or the intradural assembly over or around the outside surface of the transdural portion to narrow the distance in between and securing the intradural and extradural assemblies in the clamped position has the beneficial effect of clamping the dura between the clamping portions of the intradural and extradural assemblies.

Figure 1:
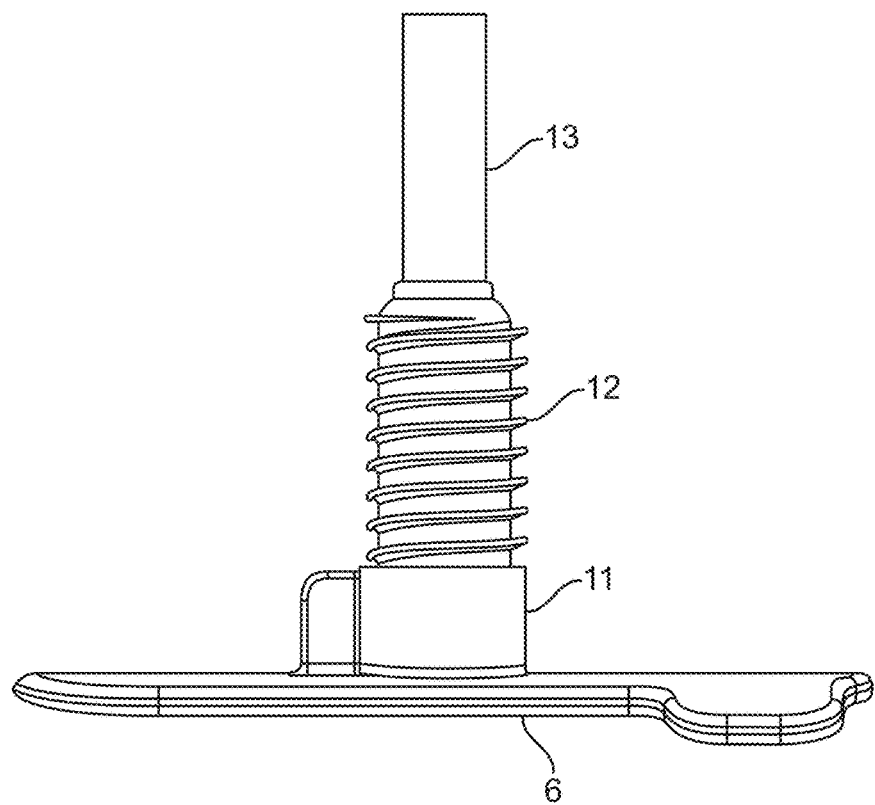
Figure 2:
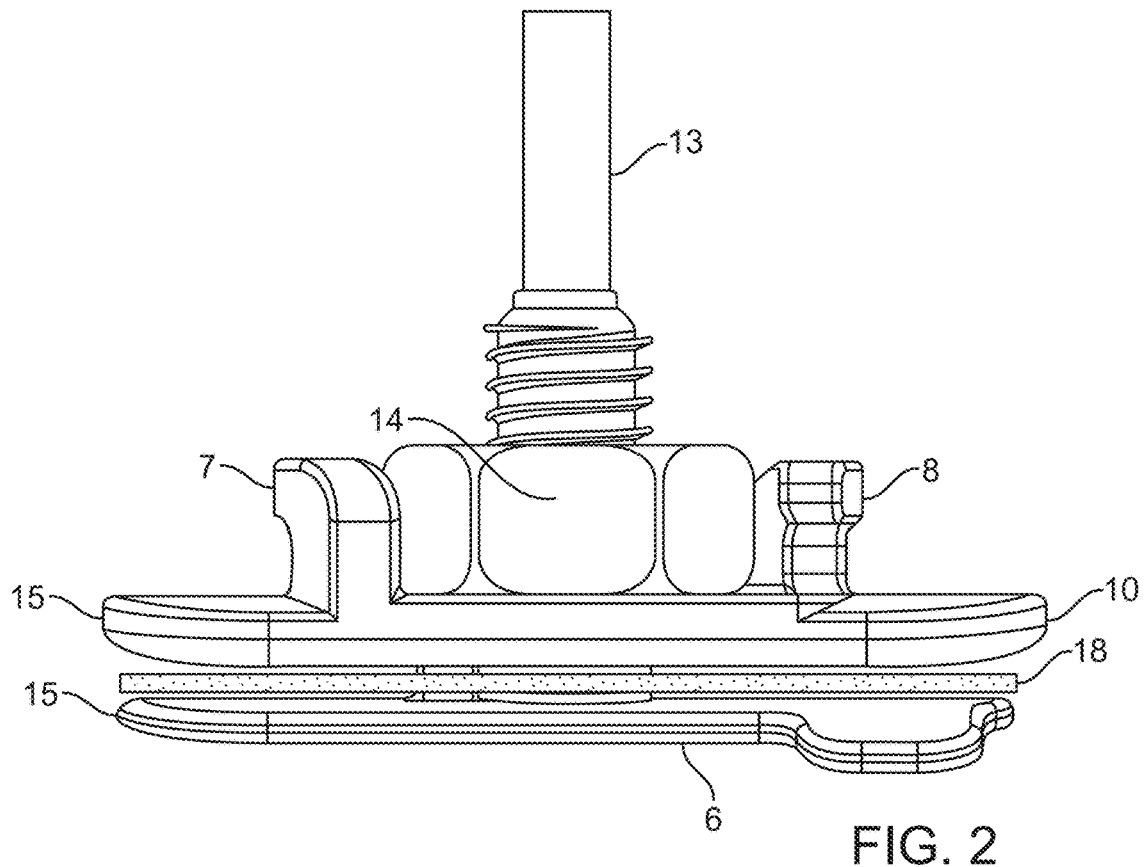

By way of illustration, the device shown in FIGS. 1 and 2 has an intradural assembly 6 that is affixed to the transdural portion 11 and 12. The extradural assembly 7, 8, and 10 is configured to slide over the outside surface of the transdural portion 11 and 12 towards the intradural assembly 6. The outside surface of the transdural portion around the longitudinal axis can be cylindrical, or any other shape that allows the extradural assembly to be brought towards the intradural assembly and secured in the clamping position to the transdural portion. In this illustration, a part of the transdural portion 12 has threading to receive and retain the lock nut 14.

In some implementations of the invention (exemplified in FIGS. 1, 2, 8A and 8B), the base plate of the intradural assembly 6 and the base plate of the extradural assembly 10 are oval, ellipsoidal, rectangular, or oblong in shape so that the surgical incision made during implantation of the device is occluded between the intradural and extradural assemblies when the device is in the clamped position. A plurality of electrodes may be arranged along the long axis of the oblong shape of the intradural assembly. In other implementations of the invention (exemplified in FIGS. 11A and 11B), the intradural assembly is a spiral or an open circle in shape so as to be rotatably insertable through a narrow incision. The extradural assembly is round and has a perimeter that aligns with the perimeter of the intradural assembly, so that they may clamp the dura between them. In various implementations of the invention, the number of electrodes present may be at least one, two, four, seven, or ten or more, arranged in a one, two or three dimensional array along the intradural assembly, the transdural portion, the flange arms, or combinations thereof.

To secure the extradural assembly in place in the clamped position, any suitable securing means may be used that holds the intradural clamping surface and the extradural clamping surface in sufficient proximity to secure the device to the dura.

An exemplary means for clamping the extradural assembly to the intradural assembly is shown in FIG. 2. In this configuration, the transdural portion 11 and 12 is attached to the intradural portion 6. The extradural portion 10 has an opening that circumscribes and slides over the transdural portion, clamping the dura 18 against the intradural portion 6. The lock nut 14 screws down the outer thread on the transdural portion 12, tightening the extradural portion to the intradural portion in the clamped portion, and reversibly securing it in place.

Other options for clamping the extradural assembly to the intradural assembly include one or more prongs or securing snaps extending radially outward from the circumferential perimeter of the transdural portion, optionally spring loaded. Prongs or snaps of this kind are shown as component 34 in FIG. 14. The extradural gasket slides downwards along or over the transdural portion to a position beyond the prongs or snaps, which thereafter prevent the gasket from sliding back up the transdural portion.

Another option is a snap in the manner of a snap button, with a male component on the extradural gasket and a corresponding female component on the transdural portion (or vice versa). Another option is a tongue and groove system, such as a bayonet-style connector, with a tongue located on the extradural assembly and a corresponding groove located on the transdural portion, or vice versa, that engage when the extradural assembly is sufficiently close to the intradural assembly to apply a securing force between the clamping surfaces to the dura. For example, a tongue on the extradural assembly may slide down a groove in the transdural portion whereupon the extradural assembly can be rotated about the transdural portion to a position that locks the extradural assembly in place in the clamped position.

Another option is to have complementary screw threads on the extradural assembly and the transdural portion. In this configuration, the extradural assembly is rotated about the transdural portion so as to screw it downwards, closing the distance between the clamping surfaces. Thus, the securing means on the transdural portion may include one or more elements selected from prongs, the male or female portion of a snap, the male or female portion of a tongue and groove system, ratchet-like couplers, or a thread system that interacts with corresponding members on the extradural device. Suitable lubricants may be used to facilitate the implantation of the device components, and suitable adhesives may be used to facilitate the securing of the device components and the dural seal.

When the device is implemented such that the intradural assembly is slidably or rotatably connected to the transdural portion, it may be moved towards the extradural assembly and secured in position using the same features as with the extradural assembly, mutatis mutandis.

Deployable Intradural Assembly

In some implementations of the invention, the intradural assembly of the device is also transformable: specifically, from an INSERT or RETRACTED position to a DEPLOYED position in which a clamping portion of the intradural assembly extends radially beyond the outside surface of the transdural portion. Where the intradural assembly is deployable in this fashion, the intradural assembly can be constructed to include multiple flanges, wherein at least one of the flanges is moveable from a retracted or insert position. When the intradural assembly is in the insert position, the flanges are underneath or inside the transdural portion or are parallel with each other so they can be stacked on top of each other. When they are in the deployed position, part of each of the flanges is extended radially beyond the outside surface of the transdural portion in a different direction.

Figure 11A:
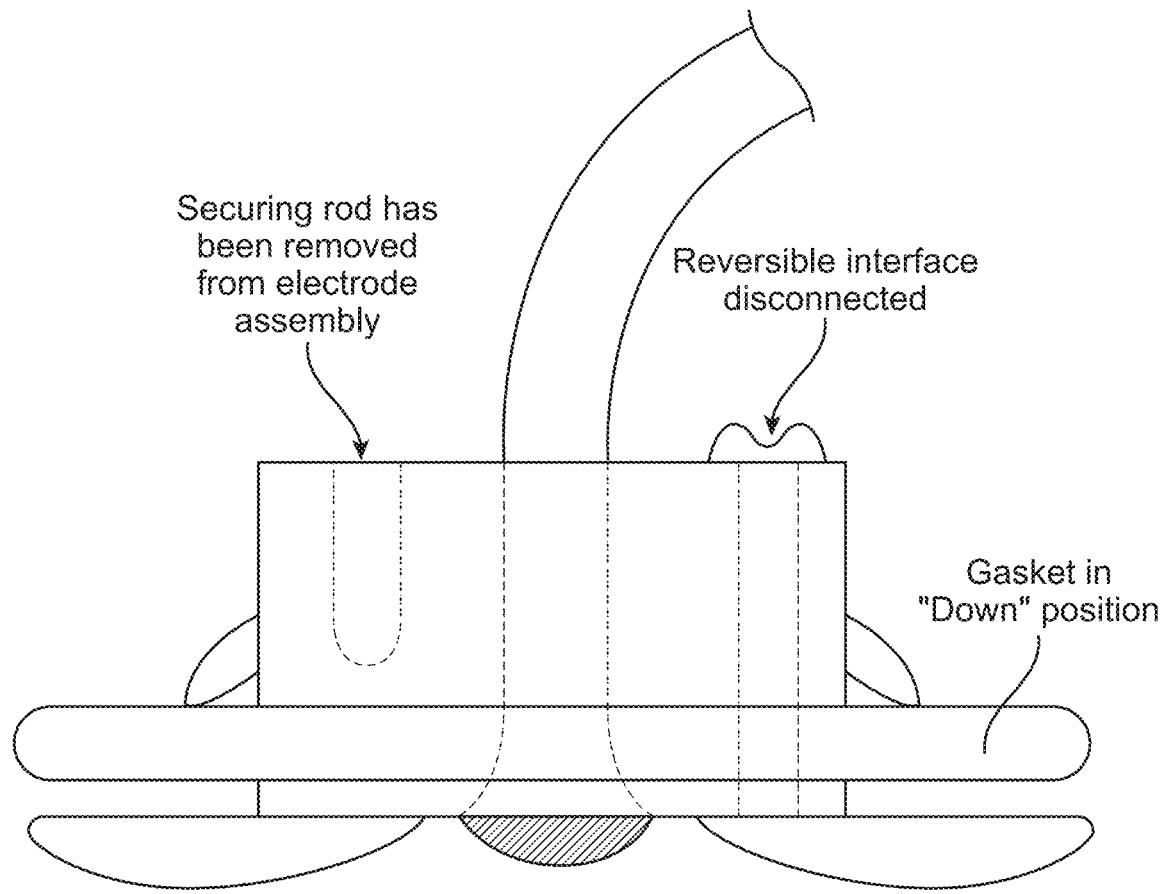
Figure 11B:
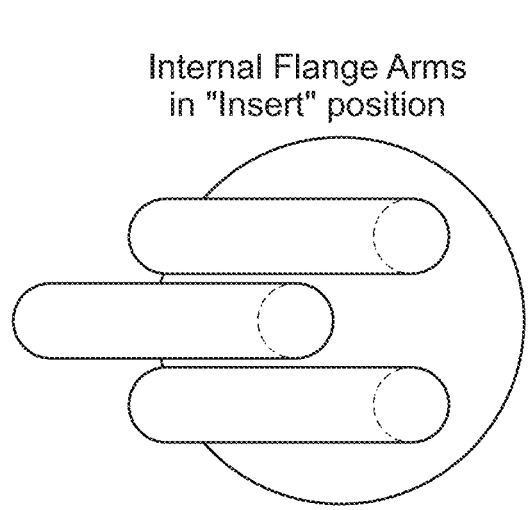
Figure 11C:
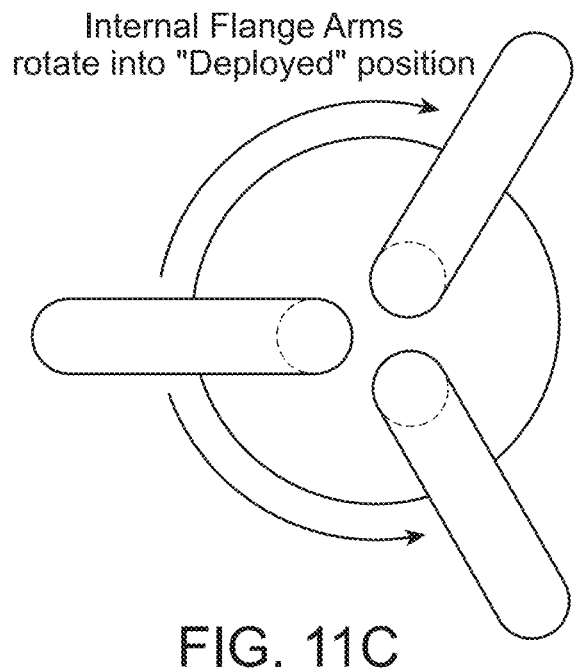

FIGS. 11B and 11C show an example in which the intradural assembly comprises both a circular component affixed or connected to the transdural portion with a clamping portion that extends radially to a position beyond the outside surface of the transdural portion, and at least three compliant flanges, wherein at least two of the flanges are rotatably movable from an insert position in which the flanges are parallel with each other to a deployed position in which each of the flanges extend away from the transdural portion in a different direction. One or more of the flanges may include a flange arm that extends radially beyond the transdural portion by at least 1 cm. One or more of the flange arms may include two or more separate electrodes arrayed along the length of the arm.

To facilitate deployment of the compliant flanges during implantation, each of the rotatably deployable flanges may be connected to an axle that passes through the transdural portion in the direction of the longitudinal axis to an opposing or outward facing surface of the transdural portion such that rotating the axle from the opposing surface moves the flange from the insert position to the deployed position.

Additional Features

The device can have at least one electrode positioned on or near the longitudinal axis so that when the device is secured to the dura, the electrode is inside the dura, oriented towards the spinal cord. Alternatively or in addition, there may be one or more electrodes arrayed on the intradural assembly. The device may also have a socket or coupling (for example, with screw threads or a tongue-and-groove locking system) for reversibly securing the device to a positioning tool such that the device can be manipulated to place the intradural assembly inside the dura, whereupon the positioning tool can be removed from the socket.

This invention includes such devices in combination with a signal source that delivers electrical stimulation to the spinal cord of a subject by way of the device. The signal source may be included in the device itself, but is often implanted elsewhere in the subject. Power can be transmitted from the signal source to the device wirelessly or by way of wire leads connecting the two. When the device is used for high-frequency stimulation, the electrical stimulation provided with the signal source may vary or fluctuate at a frequency that is sufficiently high to induce stochastic depolarization and/or to reduce pain transmission through the spinal cord. This may be a frequency of at least about 200 or 500 Hz, or as explained in more detail below.

A subject can be prepared for treatment of pain, movement disorder, spasticity, or other indications by gaining surgical access to the dura surrounding the spinal cord of the subject, making a short incision in the dura, positioning a device of this invention such that the intradural assembly is inside the dura, the transdural portion passes from inside the dura to outside the dura, and the extradural assembly is outside the dura, narrowing the distance between the intradural assembly and the extradural assembly to a clamped position, and securing the intradural and/or the extradural assembly in place so as to sustain the clamped position, thereby securing the device stably to the dura. When the intradural assembly includes multiple flanges retracted underneath or inside the transdural portion or oriented in parallel, installation of the device includes rotating at least one of the flanges to a deployed position whereby each flange is oriented in a different direction before narrowing the distance between the intradural and extradural assemblies to the clamped position.

Depending on the configuration, the clamping portions of the intradural and extradural assemblies may seal the dura to prevent leakage of cerebrospinal fluid into the epidural compartment or egress of epidural effluents into the intradural compartment. Any open gaps or leakage can be repaired by the operating surgeon using suture, staples, glue, or any other appropriate closure materials. The surgeon then connects the device to an appropriately programmed and equipped signal source.

The invention also provides various configurations of a positioning or inserting tool for clamping a device of this invention to the dura surrounding the spinal cord of a subject. The nature and operation of the tool are described in more detail in the sections that follow.

Implementation of the Invention with a Lock Nut Clamping Means

In the implementations of the invention shown in FIGS. 1 to 10, the common numbering scheme for the components is as follows:

Positioning Tool:

| | |
|---|---|
| Proximal end of central axial shaft | 1 |
| Proximal fixation fitting | 2 |
| Proximal rotation hub | 3 |
| MIS insertion shaft assembly | 4 |
| Distal hub | 5 |
| Rotational coupler for extradural lock nut | 9 |

Electrode Assembly:

| | |
|---|---|
| Intradural electrode substrate and compression plate | 6 |
| Lateral interlock notch | 7 |
| Contralateral interlock notch | 8 |
| Extradural compression plate | 10 |
| Transdural housing for electrode array connector | 11 |
| Extradural threaded stud | 12 |
| Distal end of central axial shaft | 13 |
| Lock nut in fully engaged position | 14 |
| Gasket | 15 |
| Electrical leads | 19 |
| Intradural electrode array | 20 |
| Individual electrodes on the intradural array | 21 |

Other Components:

| | |
|---|---|
| Epidural stimulator implant | 23 |
| Electrical leads of epidural stimulator implant | 24 |
| Implantable pulse generator (IPG) | 25 |
| First independent channel of IPG | 26 |
| Second independent channel of IPG | 27 |

Anatomical and Surgical Features:

| | |
|---|---|
| Stabilization suture | 16 |
| Eyelet | 17 |
| Dura mater | 18 |
| Spinal cord | 22 |

FIG. 1 shows details of the compression plate 6 of the intradural assembly, which serves as a substrate for an electrode array configured for positioning in the intradural space. In this implementation of the invention, the transdural portion 11 and 12 is affixed directly to the intradural assembly 6. The upper portion 12 (an axial extension of the distal base bushing 11) has an outer thread that engages the locknut 14. In this example, the intradural compression plate 6 is T-shaped in profile, with the crossbar of the T located on its contra-lateral side (shown on the right). Distal bushing 11 has lateral and contralateral extension tabs, each of which serves as a positional index that secures the alignment of the compression plate 10 of the extradural assembly.

This arrangement ensures that the long axis of the extradural compression plate 10 is directly above that of the intradural compression plate 6 so that there is exact overlap of the gasket materials 15 between these plates. This helps maximize the gasket coverage of the dura mater membrane sandwiched therebetween. The distal bushing 11, the threaded-stud fitting 12, and the central axial shaft distal end 13 are hollow inside. This serves as the containment for electrical leads connected to the electrode array on the distal surface of the extradural compression plate 6. The leads extend from that connector through the length of the assembly, and ultimately exit the aperture at the proximal end of the central axial shaft. The device components are typically made from biocompatible polymers such as polyether ether ketone (PEEK), except the electrode array, its connectors and leads, and the compression gaskets.

Gaskets 15 can be attached to the compression plates using adhesives, mechanical clamping mechanisms, or combinations thereof. In FIG. 2, the gaskets 15 are shown as the layers of the assembly sandwiched between the dura 18 and the compression plates 10 and 6. In this particular illustration, the gaskets are substantially the same size and shape at the compression plates 6 and 10. Optionally, the gasket extend beyond the edges of one or more of the compression plates or gaskets that have a surface area that is smaller than the surface area of the compression plates. Alternatively, either single-layer or multi-layer gaskets are not adhered to the compression plates, but form a seal preventing leakage of the CSF upon implantation and tightening of the device around the dural membrane. To accomplish this, the gaskets can be made out of a biocompatible material that is capable of creating a seal and preventing CSF leakage. Suitable materials may include polyurethane, polyamide-polyurethane, collagen dura membranes, polylactide-co-glycolide, polyethylene glycol hydrogel, silicone rubbers, silicone caulks, silicone resins, polysiloxanes, and low-durometer elastomers, combinations thereof, and compositions that include as a component one or more of these materials.

FIG. 2 shows the locking nut 14 after it has been rotationally driven into place on the threaded adjustment fitting 12, which results in optimal positioning of the extradural compression plate 10 directly above the intradural compression plate 6. The intradural compression plate 6 is T-shaped in profile, with the crossbar of the T located on its contralateral side (shown on the right). The extradural assembly includes contralateral interlock notch mechanisms 7 and 8 that reversibly engage corresponding notch mechanisms on the positioning tool.

Once locking nut 14 is secured in position on the threaded stud, the dura mater extant between the compression plates is compressed on both the proximal and distal surfaces by gaskets positioned between the distal side of the extradural compression plate 10 and the proximal side of the intradural compression plate 6. The gaskets ensure a watertight seal against leakage of CSF either through the durotomy opening or via any other pathway between the intrathecal space and the epidural space. The gasket material can be bioresorbable so as to fuse over time with the dura mater to form a fully re-approximated anatomical membrane with biomechanical characteristics that are substantially identical to the native dura mater membrane.

The other device components are typically made of biocompatible polymers such as PEEK, except the electrode array and its connectors and leads, and the compression gaskets. The sealing effects achieved by the compression gaskets may be augmented with layers of tissue sealant films applied to the gaskets before implantation, and/or with auxiliary sutures, glues, adhesives, blood patches or other materials.

Figure 3:
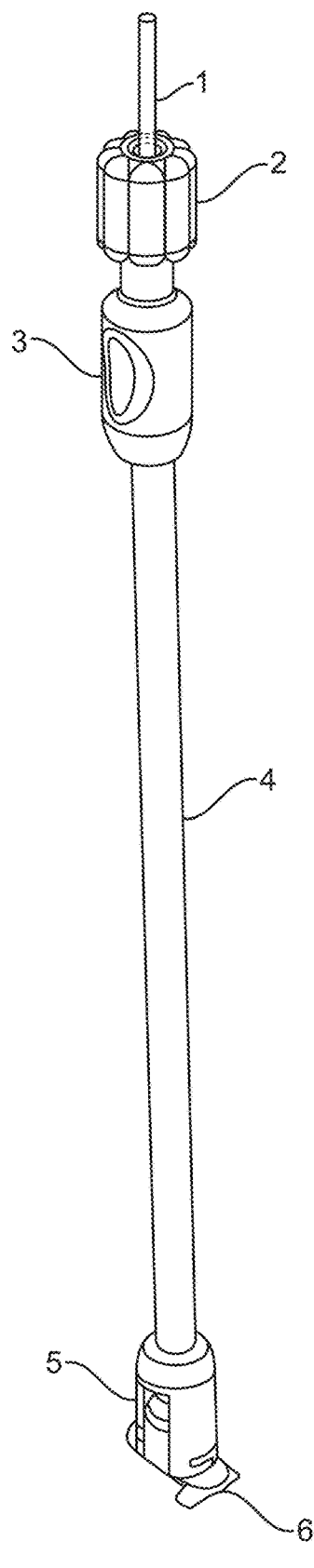

FIG. 3 shows a full side profile view of the pre-deployed configuration, with the combined intradural assembly 6 and extradural assembly attached to a positioning tool 1 to 5. The positioning tool is a surgical implement used to place and secure the combined assembly in position on the dural membrane of the spinal cord at a chosen location. During the implantation procedure, the positioning tool is used to reconfigure. the assembly from the open position to the clamped position, where it is secured in the dural membrane by way of the locking nut. The positioning tool is then removed from the surgical field for reuse or disposal, allowing the surgeon to close the wound with the electrode assembly in place.

The positioning tool has a proximal end (top) and a distal end (bottom). It extends longitudinally downward through the device and terminates inside a fixture within the distal hub assembly 5. Electrical leads from the intradural electrode array 6 at the distal end of the positioning tool traverse the length of the central axial shaft and exit from its proximal end aperture. The upper rotation hub 3 is used to twist the cylindrical housing shaft 4 about the longitudinal axis of the tool in order to tighten a lock nut onto the threaded shaft of a connector housing, both of which are inside of distal hub assembly 5. This draws together the intradural compression plate 6 and the extradural compression plate 10 so that gaskets between them are forced against the spinal dura mater and sandwich it between them to form a watertight seal against leakage of cerebrospinal fluid.

The knurled upper fixation fitting 2 is used to maintain components 3, 4, and 5 in axial order as shown and to ensure continuous rotation of 4 in response to a manually applied twist of 3. When fitting 2 is loosened and removed, components 3, 4, and 5 can be withdrawn from the assembly, leaving just the distal intradural and extradural assemblies in place, along with the transdural portion. All of the device components are typically made of biocompatible polymers, such as polyetheretherketone (PEEK) except the electrode array and its connectors and leads, and the compression gaskets.

Figure 4:
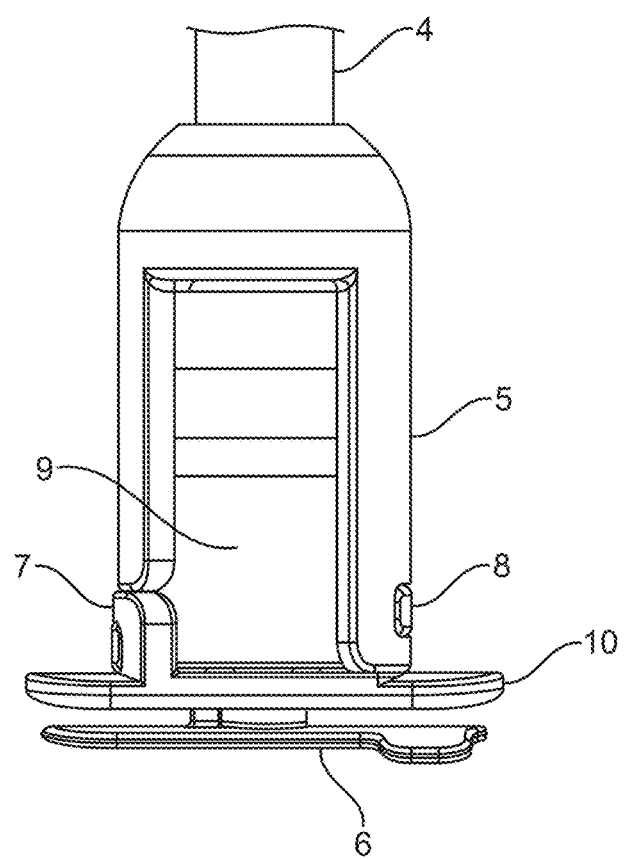

FIG. 4 shows the extradural and intradural assemblies at the distal tip of the positioning device. The cylindrical housing shaft 4 passes into the proximal end of the distal hub assembly 5, which surrounds the rotational coupler 9 for the extradural lock nut 14. The distal hub assembly 5 is mated to the extradural compression plate 10 by the lateral and contra-lateral interlock notches 7 and 8, respectively. Rotation of the coupler 9 draws upwards a threaded-stud housing attached proximally to the intradural compression plate 6 so as to compress gaskets integral to the distal side of 10 and to the proximal side of 9 onto a dura mater which is traversed by the threaded-stud housing, thus forming a leak-free seal against egress of CSF from within the thecal sac into the epidural space.

The intradural compression plate 6 has a T-shaped in profile, with the crossbar of the T located on its contra-lateral side (shown on the right). The device components are typically made of biocompatible polymers such as PEEK, except the electrode array and its connectors and leads, and the compression gaskets. The gaskets can be made from known materials that are used in dural replacement procedures. The gaskets may have thicknesses in the range of 0.1 mm to 0.7 mm as appropriate to the scale of the implant and the thickness of the patient's dura mater. The gaskets may be coated with dural sealant films or membranes to help achieve a leak-free closure of the dura. The seal is typically augmented naturally over time by scar tissue that forms in response to the presence of the intradural components.

Figure 5A:
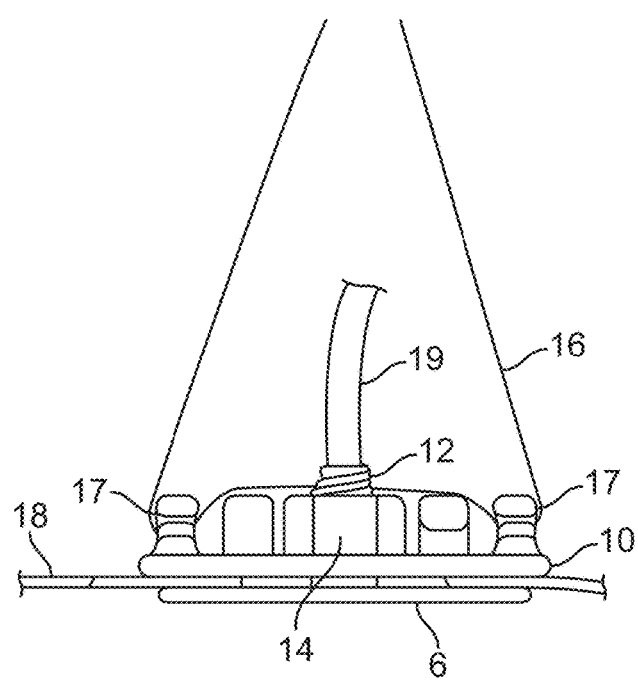
Figure 5B:
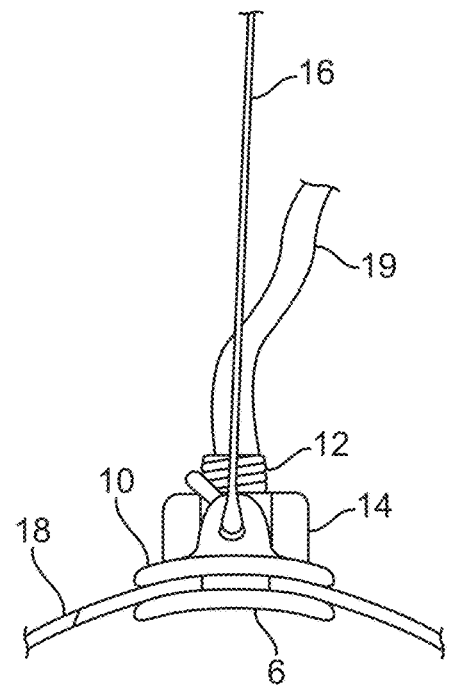

FIG. 5A (side view) and 5B (rostral-caudal view) show close-ups of a mechanical stabilization means for securing the extradural elements of the implant within the patient. The device shown here includes a take-up suture 16, which is threaded through lateral and contralateral eyelets 17, which extend proximally from the extradural compression plate 10. After the lock nut 14 has been used to tighten the extradural compression plate 10 against the intradural compression plate 6, fixing the dura mater 18 between them, the take-up suture 16 is threaded in place as shown. The proximal ends are secured directly to extradural fascial tissues, thus ensuring that the implant is suspended stably above the spinal cord, providing stress relief for the electrical leads 19 that connect the intradural electrode array underneath the distal compression plate to a pulse generator implanted elsewhere within the patient's body.

Figure 6:
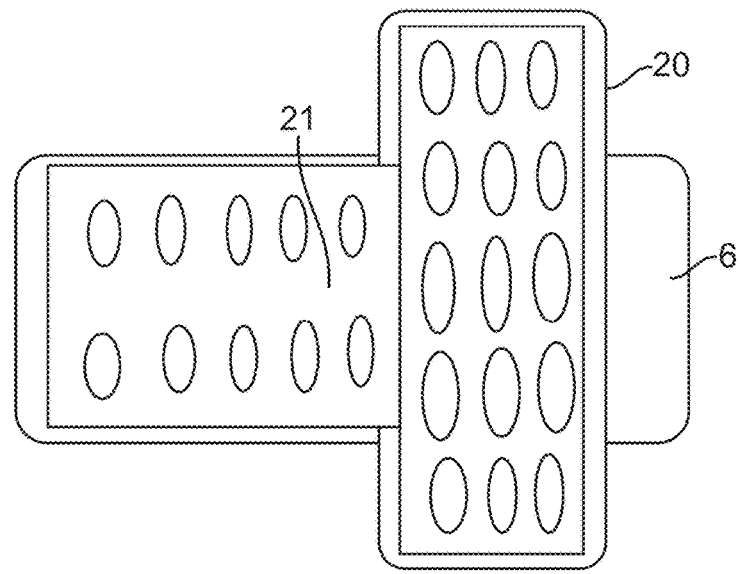

FIG. 6 shows a possible geometry for an intradural electrode array 20, mounted on the distal side of the intradural compression plate 6. In this example, the array 20 is manufactured in the shape of the letter "T". The electrodes along the long (rostral-caudal) axis of the intradural compression plate 6 help stimulate nerve fibers in the dorsal columns of the spinal cord. The electrodes along the short (lateral) axis of the intradural compression plate 6 help steer the stimulation field to achieve selective activation of target structures elsewhere within the spinal cord, without inadvertently activating the dorsal nerve rootlets or other off-axis structures that could produce discomfort, pain or paresthesias in the patient. Individual electrodes may be treated by laser etching or some other suitable method for the purpose of generating nano- and micro-patterned structures to increase their active surface area by, for instance, 2-fold, 5-fold, or more in order to generate current densities at the electrode-CSF interface that maximize the therapeutic response of the treatment while minimizing the risks of neurotoxicity due to electrolytic effects and excessive charge densities.

The electrical leads from the electrode array may be attached to an intermediate body inside the extradural components of the device. This may provide an interface structure for stress relief for the very fine wires or conductors that exit from the thin film electrode array. Alternatively, the leads from the electrode array are connected directly to a lead bundle that extends proximally from that connection point to the outside of the extradural components of the implant, at which point the lead bundle is secured to the body tissues.

Figure 7:
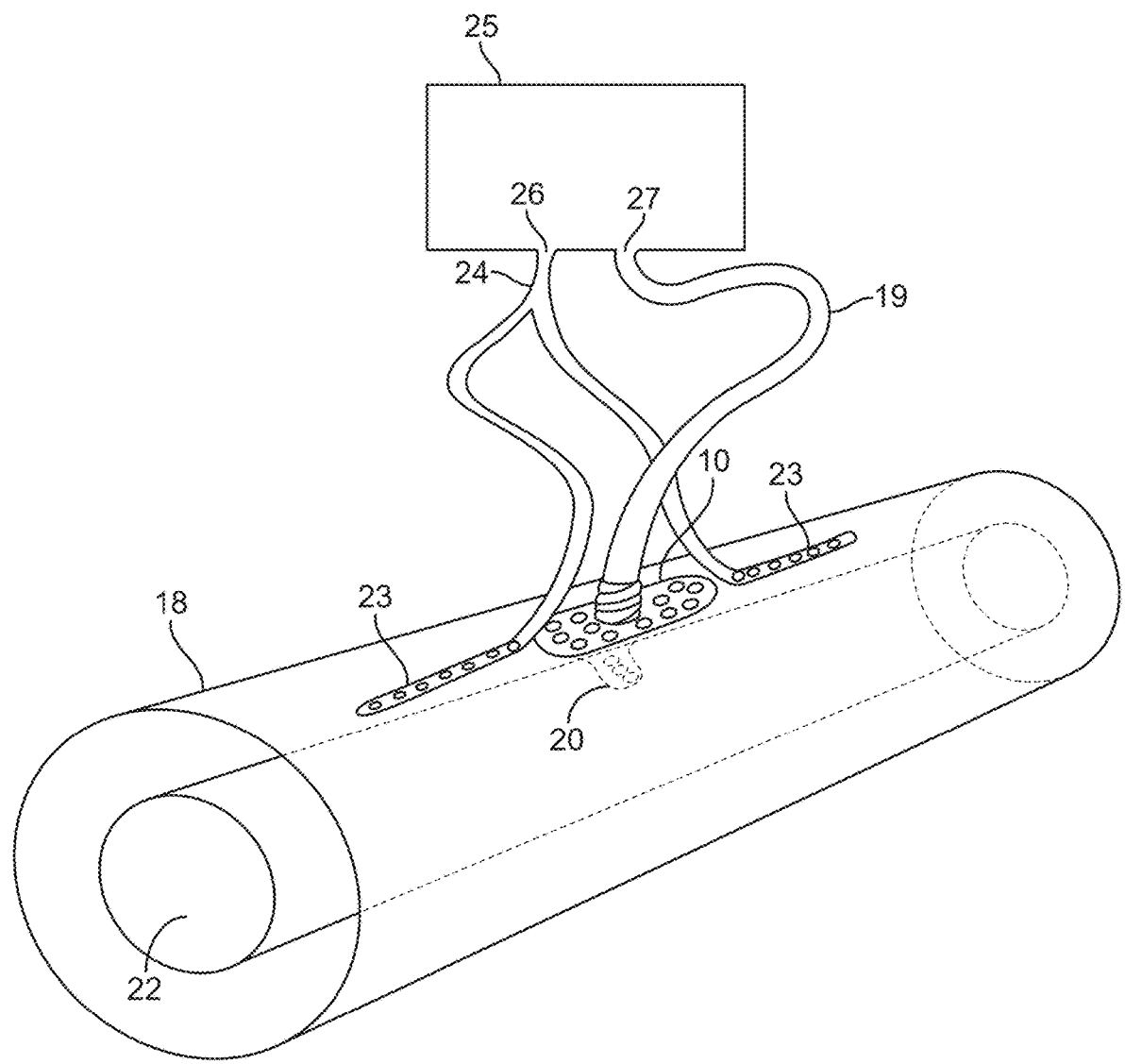
Figures 8A, 8B:
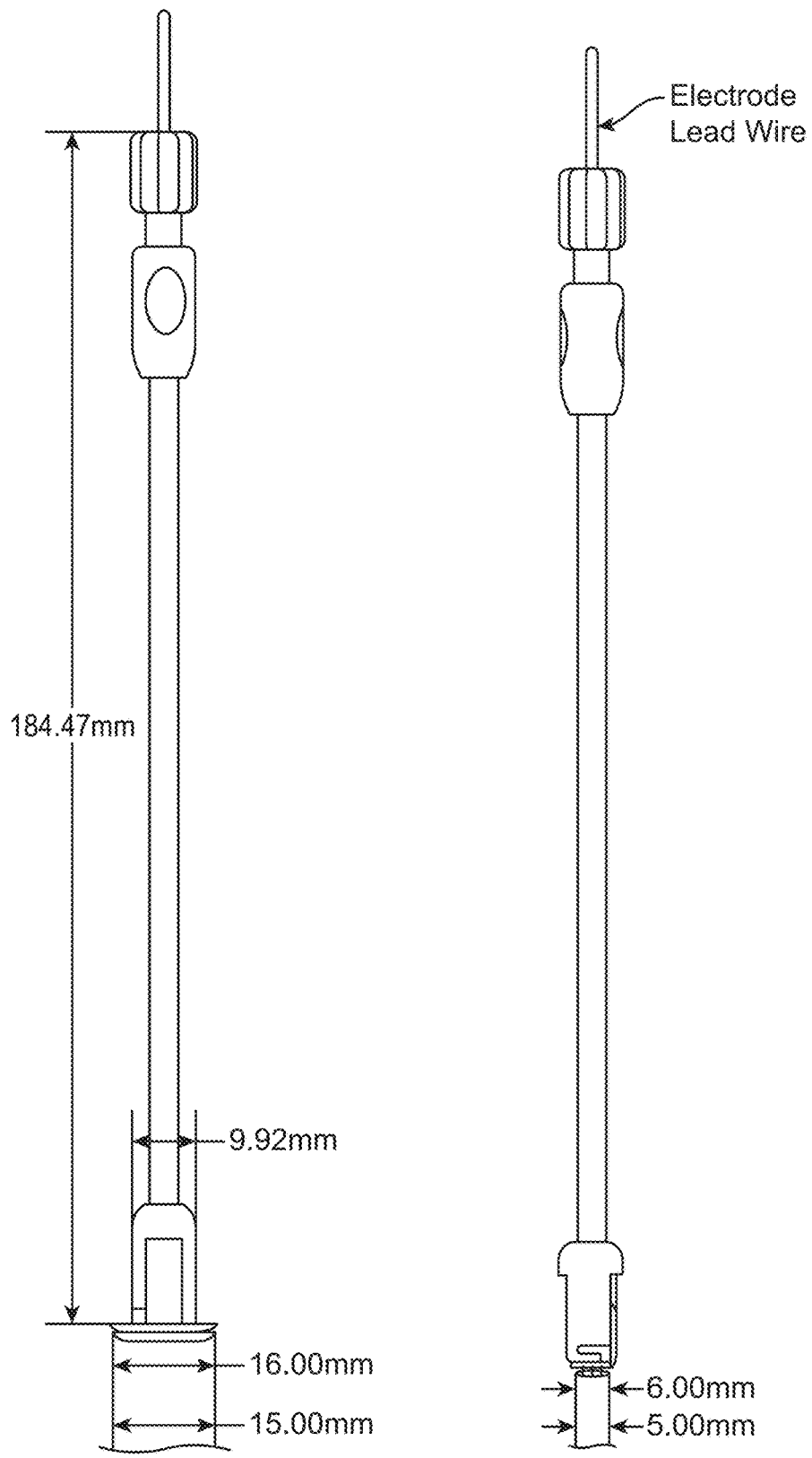
Figure 9:
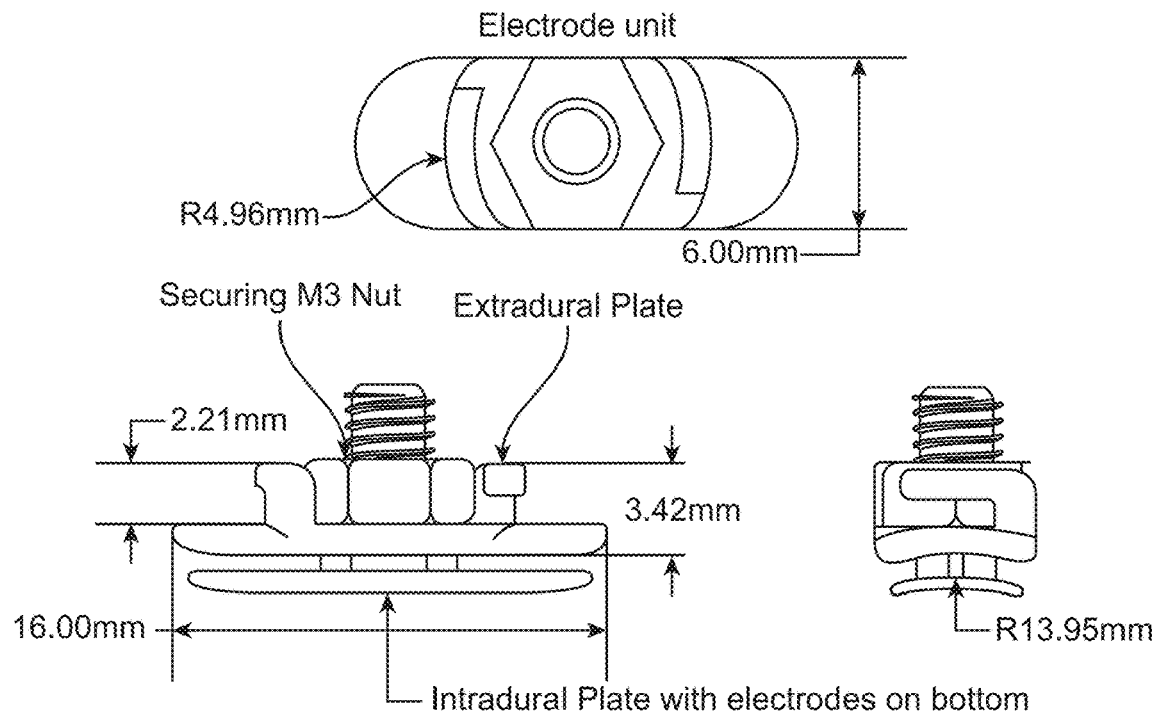

FIG. 7 shows the intradural assembly combined with the extradural assembly, achieving extended coverage of the spinal cord, with improved targeting of critical structures and avoiding non-targeted structures. The intradural array 20 is inside of the dura mater 18 and suspended over the spinal cord 20. The electrical leads 19 from the intradural array 20 are interfaced with one independent channel 27 of an implantable pulse generator 25. Also shown are standard cylindrically-shaped, low profile epidural stimulator implant leads 23, which are positioned in the extradural space rostral and caudal to the intradural implant. The electrical connector 24 from the epidural stimulator implant leads 23 is interfaced with another independent channel 26 of implantable pulse generator 25.

This arrangement allows the clinician to use combinations of extradural and intradural stimulation to achieve the best clinical results for the patient, and also allows combined epidural and intradural sensing of evoked compound action potential for use in closed-loop stimulation algorithms. For example, the intradural stimulator array may be inserted first, and then the epidural leads are slipped into the extradural space rostral and caudal to the intradural array. The electrical leads of both the intradural and extradural implants is then connected to the implantable pulse generator 25. This arrangement allows for exhaustive and rigorous testing of key neurophysiological hypotheses. For example, the user could directly compare extradural vs. intradural stimulation in the same subject and test combinations of intradural and extradural contacts in various montages, with the goal of identifying, implanting and implementing the optimal configuration of devices for the needs of the patient.

FIGS. 8A, 8B, 9, and 10 show possible geometries and measurements for the electrode assembly and positioning tool shown in FIGS. 1 to 4. The intradural plate 10 and the extradural plate 6 are about 1.5 cm by 0.5 cm in shape. They are attached by way of a 1.0 cm socket to the positioning tool, which is 18.5 cm in length.

The intradural compression plate 6 is thin (0.5 to 1.5 mm) so as to minimize the risk of impeding the flow of CSF through the gap between the plate and the underlying spinal cord. The plate is shown here as oval, which when positioned parallel to the spinal cord helps seal the incision in the dura. The peripheral edges of the plate are typically smooth and free of burrs or other production artifacts that could pose a risk of tearing or scarring the dura mater. The planar surfaces are smooth to ensure optimal contact with the gasket used to seal the dura mater against the plate.

Implementations of the Invention with Other Clamping Means

In the implementations of the invention shown in FIGS. 11A to 26F, the common numbering scheme for the components is as follows:

| Intradural assembly: | |
|---|---|
| Intradural gasket | 12 |
| Intradural clamping surface | 13 |
| Electrode | 14 |
| Flange | 15 |
| Flange rotator | 16 |

| Intradural assembly: | 11 |
|---|---|
| Intradural gasket | 12 |
| Intradural clamping surface | 13 |
| Electrode | 14 |
| Flange | 15 |
| Flange rotator | 16 |

| Extradural assembly: | 21 |
|---|---|
| Extradural gasket | 22 |
| Extradural clamping surface | 23 |

| Transdural portion: | 31 |
|---|---|
| Lead | 32 |
| Socket | 33 |
| Securing member | 34 |
| Flange rotator | 35 |
| Connecting surface of rotator | 36 |

| Positioning tool: | |
|---|---|
| Inner housing | 41 |
| Compression sleeve | 42 |
| Handle | 43 |
| Positioning rod | 44 |
| Groove | 45 |
| Flange control rod | 46 |

FIGS. 11A, 11B, and 11C show an implementation of the device using compliant flange arms as part of the intradural assembly. FIG. 11A is a side view, showing the transdural portion 31 with wire leads or lead bundle 32 for connecting to a signal source (not shown). The intradural assembly 11 includes one or more electrodes 14 and turnable flanges 15 that have an intradural clamping surface 13. The extradural assembly 21 includes an extradural gasket 22 with an extradural clamping surface 23. The extradural assembly is configured to slide downwards along the outside surface of the transdural portion 31 until it is held in position by securing members 34. This secures the extradural gasket 22 at a position adjacent to the flanges 15 with just enough space to clamp or secure the device to the dura. Also shown is a socket or receiving member 33 for reversibly securing the device to a positioning tool. This allows the device to be manipulated to place the intradural assembly inside the dura, whereupon the positioning tool can be removed from the socket. A flange rotator 35 passes through the transdural portion from each of at least some of the flanges so that the flanges can be rotated into the deployed position from outside the dura.

Depending on construction and the objectives of care, the diameter of the extradural assembly may be in the range from 5 to 9 mm. In this illustration, the length of the flange arms is in the range from 0.5 to 2 cm, with a thickness of 1 to 2 mm. The flanges and the flange arms can be made of a soft polymer like silicone, possibly with a stiffening element: for example a wire or stiff polymer material, inserted inside of the flange arms to give them axial stiffness while still maintaining torsional compliance that accommodates the curved surface of the dura during flange rotation, without risk of rupture, tear or abrasion. The extradural gasket can also be made of a soft polymer such as silicone, providing it is sufficiently rigid to keep the dura sealed around the original incision. The actual electrodes themselves may be of any suitable shape and construction, such as a small flat disk, a "spherical cap" (partial hemisphere), or a half-moon shape. They can be made of platinum or of a platinum-iridium alloy. Each electrode typically has an electrical lead welded or otherwise in permanent, secure, low-resistance ohmic contact with its proximal side.

FIG. 11B shows the flanges 15 in a substantially parallel orientation from beneath the transdural portion 31. This is the retracted or insert position, whereby the surgeon may insert the flanges together through an incision in the dura. FIG. 11C shows the flanges 15 rotated to the deployed position, anchoring the intradural assembly underneath the dural membrane.

Figure 12A:
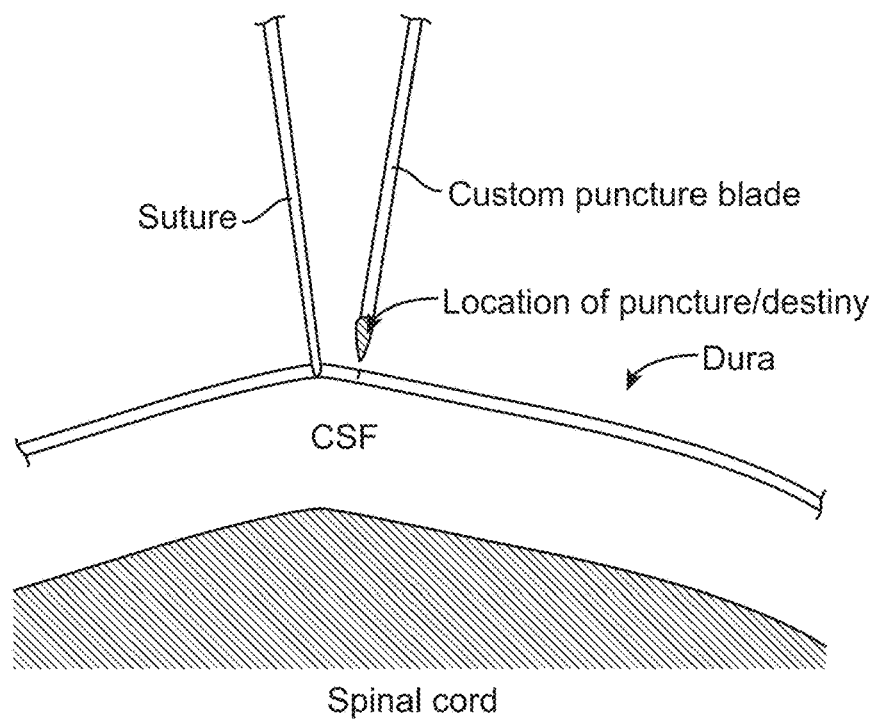
FIGS. 12A to 12E show use of an inserting tool 40 to insert and clamp the device shown in FIG. 11A to the dura of a spinal cord.

FIGS. 12A to 12E show how this device can be secured to the dura of a subject. In FIG. 12A, the dorsal surface of the spinal dura is accessed using the standard surgical approach. The exposure achieved with minimally invasive surgery (MIS) devices and methods are adequate for this purpose. A suture, or micro-hook instrument, is used to "tent up" the dura (raising it further above the surface of the spinal cord) in preparation for making a small puncture incision through the dura. A custom blade can be used to create a durotomy of the precise length required.

Figure 12B:
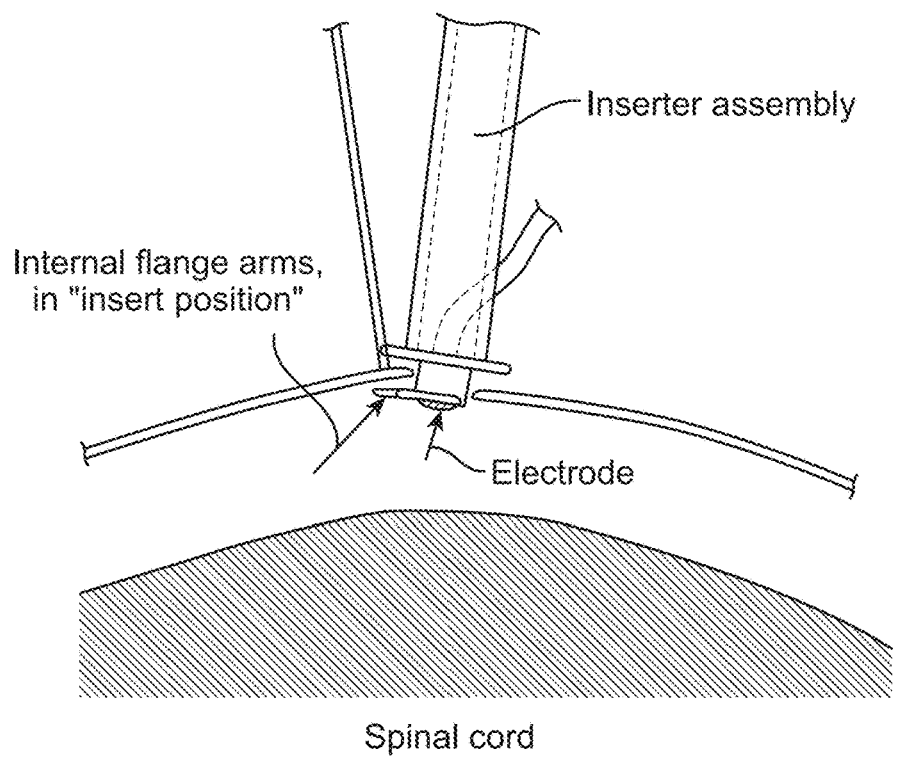

FIG. 12B shows an inserting tool 40 (described further below) being used to secure the device. As shown here, the device has the extradural gasket in the open position, an electrode 14 inside the dura oriented towards the spinal cord, and the flanges 15 in the insert position. During the implantation procedure and to control the angle of the flanges 15 that project from the undersurface of the device. The inserting tool can be configured so that one of the flanges 15 is rigidly fixed to the transdural portion with no positional controller attached to it. The rotational position of the other two internal flanges 15 are each controlled through its own flange rotator 16, which in turn is manipulated using a flange control rod that passes through the body of the inserting tool, as described below.

In the insert or retracted position, the flanges 15 are oriented substantially parallel with each other, the tips of each flange facing substantially in the same direction. This effectively creates a thin right angle dural separator (an instrument used to open the dura during neurosurgical procedures) projecting in a single direction from the undersurface of the combined electrode & inserting tool. This is a further benefit of this invention, because the surgeon can advance the parallel flanges through the durotomy into the subdural space without placing the underlying spinal cord at risk. The neurosurgeon slightly lifts the dura away from the underlying spinal cord, and then incises the dura under direct visualization. The device with the flanges in the insert position serves as the blade of a dural separator, allowing it to be introduced into the subdural space with the flanges flush with the dura, exerting an upward pressure on the dura to elevate the membrane away from the spinal cord.

Figure 12C:
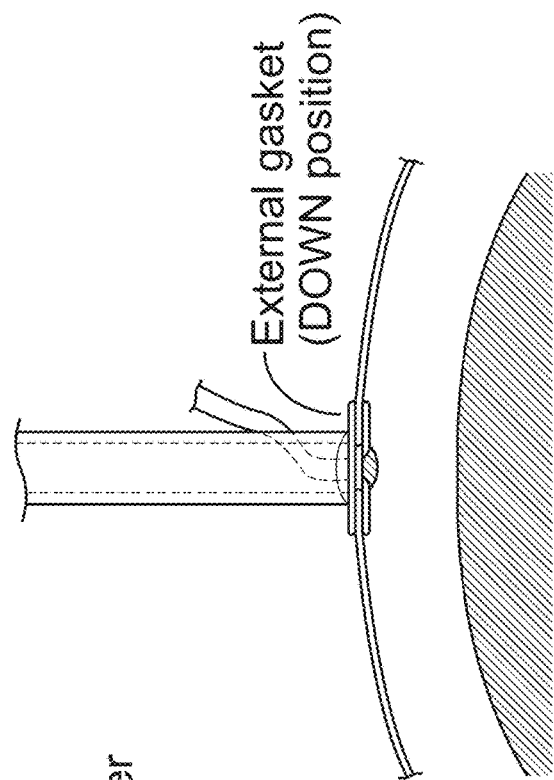

FIG. 12C shows the flanges 15 rotated to the deployed position, anchoring the device underneath the dura. Two of the flanges 15 can each be rotated independently by the surgeon using the flange rotators in the transdural portion. The surgeon controls the rotational position or angle of two of the flanges through flange control rods that extend from the opposite end of the inserting tool 30 (the portion closest to the surgeon's hand). By rotating the two mobile flanges 15 into the deployed configuration, the entire cut incised margin of the dural opening is displaced above (superficial to) the flanges. The dural edges are now located within the space between the flanges 15 and an extradural gasket 22, shown here in the up or open position. The clamping surface of the gasket can be fabricated from an artificial dura material. The outer surface of the gasket and most of the rest of the device can be fabricated of a rigid, biocompatible polymeric compound that may be MRI compatible.

Figure 12D:
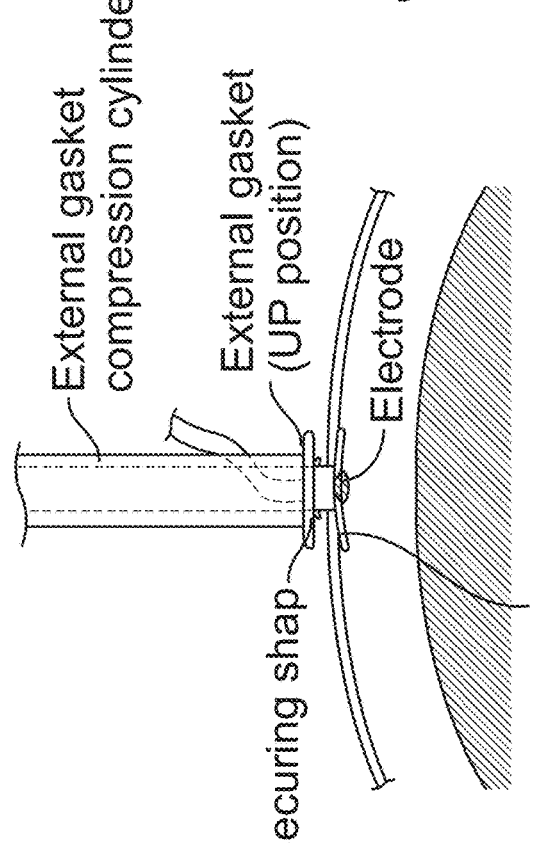

FIG. 12D shows the extradural gasket 22 compressed downwards against the flanges 15 by the inserting tool 40. After the device is properly positioned within the durotomy opening, the surgeon slides the extradural gasket compression cylinder down the assembly 40 towards the dura, thereby pushing the extradural gasket 22 past securing snaps 34 to achieve a snug, watertight closure onto the dura. Fabricating the undersurface of the gasket using an artificial dura-type substrate facilitates rapid tissue fusion of the gasket to the dura: for instance, by resorption of the dural substitute at the interface with the dura. The securing snaps 34 lock the gasket into the secured position.

Figure 12E:
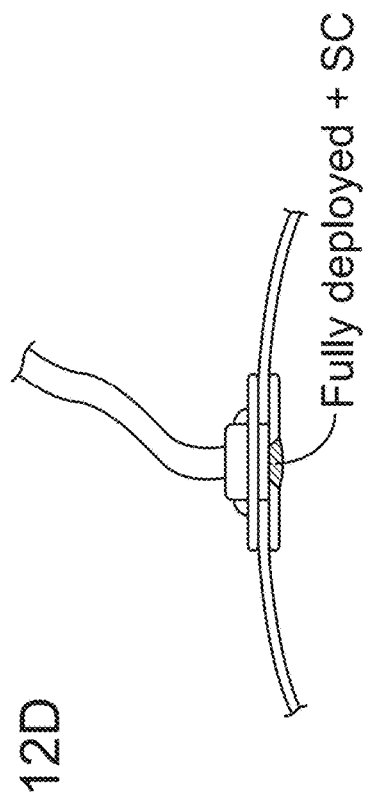

FIG. 12E shows the electrode device secured to the membrane with the inserting tool removed. The extradural gasket assembly 22 clamps the dura against the flanges 15, thereby positioning an electrode 14 so that it projects downwards from the dura towards the spinal cord.

Positioning Tool

Figures 13A, 13B, 13C:
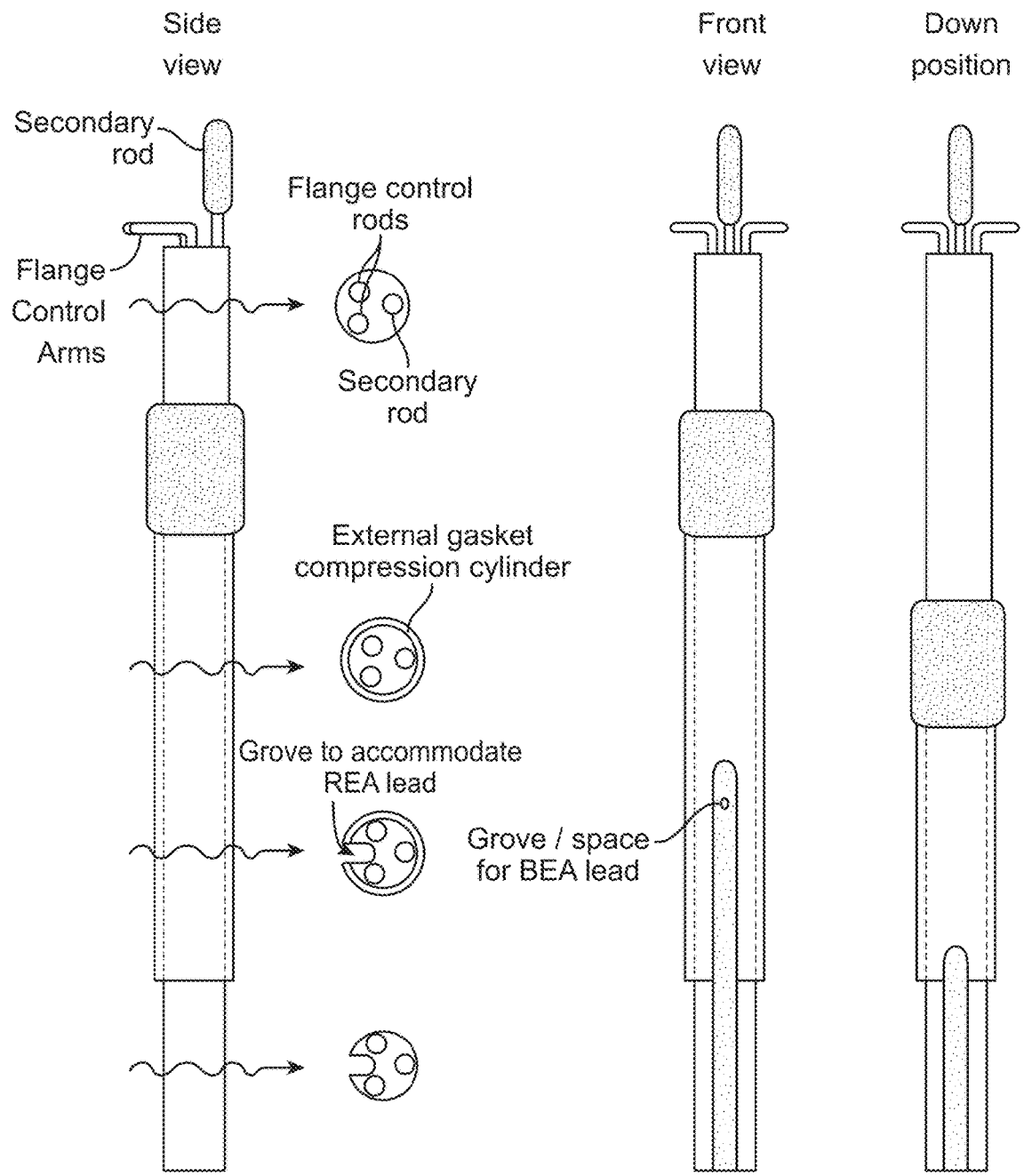
FIGS. 13A to 13C show an electrode device inserting tool by itself.

FIGS. 13A, 13B and 13C depict another inserter assembly or inserting tool that is suitable for use in implanting an electrode device of this invention into a subject. In this illustration, the inserting tool is adapted for operation of a device as shown in FIGS. 11A, 11B, and 11C with moveable flange arms. The electrode device itself is not shown.

FIG. 13A depicts a side view. Three control elements extend from the top of the device and are controlled by the surgeon. Specifically, two flange control rods 46 are used to control and adjust the position of two moveable flanges that are part of the electrode device. The positioning rod 44 reversibly connects the inserting tool to the electrode device. An extradural gasket compression cylinder 42 is shown in the UP position around the inner housing 41. Four cross-sectional images are shown depicting the internal structure of the device. In the lower two cross-sectional views a groove 45 is shown that accommodates placement of the electrical lead on the device.

FIG. 13B is a frontal view of the inserting tool by itself. This provides a view of the groove 45 that accommodates the wire lead. FIG. 13C is a frontal view with the extradural gasket compression cylinder 42 in the DOWN position. To install devices that do not have rotatable flanges, the flange control rods are not needed. The external surface of the inserting tool may conform to an oval or elliptical shape, rather than a circle, and are typically complementary to the outer surface of the extradural assembly.

Figure 14:
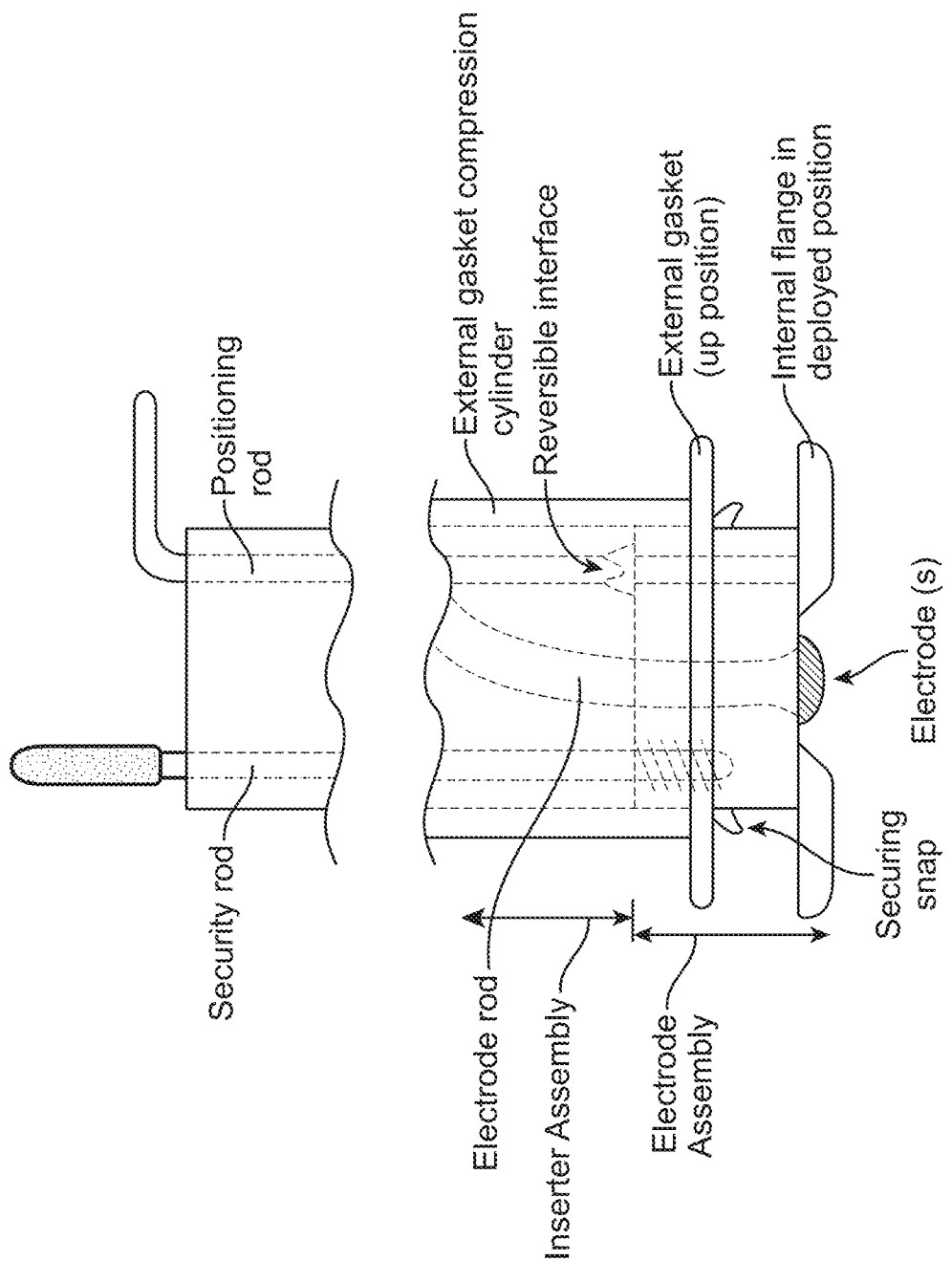
FIG. 14 shows a device according to FIG. 11A bound to the inserting tool by way of the positioning rod 44.

FIG. 14 shows the electrode device coupled with the inserting tool. In this depiction, the electrode device aligns with the housing 41 of the inserting tool, meaning that the surface of the transdural portion 31 of the device has a cross-sectional shape or diameter that is substantially the same as the housing 41. The device is kept in place at the bottom of the housing by way of the positioning rod 44 inserted into the socket 33 of the transdural portion. In this depiction, the inserting tool has a groove 45 to accommodate the lead 32 that ultimately connects the electrode 14 to the outside signal source. There are two flange control rods 46 that control the two mobile flanges 15 of the device. Each flange control rod 46 connects with a reversible interface 36 at the top of flange rotator 35 housed in the transdural portion 31 of the device, which is used to rotate the respective flange 15 to adjust the angle or intradural orientation. The interface 36 is depicted here as a slot-headed dome. In the alternative, the interface can be cross-shaped or hexagonal, matching a corresponding pattern in the flange control rod 46 of the inserting tool.

The inserting tool has a positioning rod 44 that passes from the top of the inerter that projects away from the device, down through the inserting tool to the opposite surface where the inserting tool abuts the electrode device. The positioning rod 44 reversibly interconnects with the socket 33, shown here with a screw interface, thereby securing the electrode device to the bottom of the inserting tool. After the electrode assembly is implanted in position in the subject (after the extradural gasket 22 has been locked in the down position), the positioning rod 44 is detached from the electrode device by rotation, thereby releasing the inserting tool from the electrode device, and allowing it to be removed from the operative field.

Figure 15A:
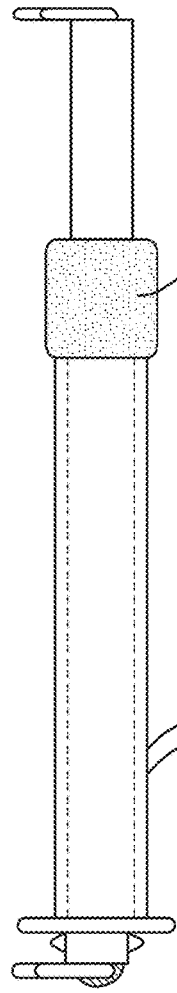
FIGS. 15A to 15C show operation of the inserting tool to transform the device from an open position to a clamped position.
Figure 15B:
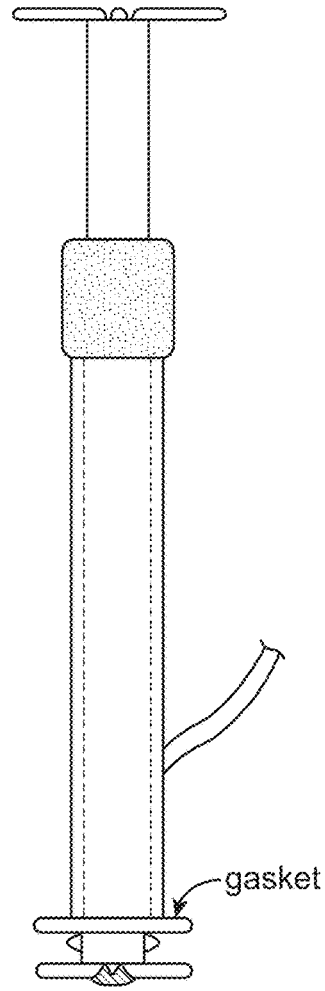
Figure 15C:
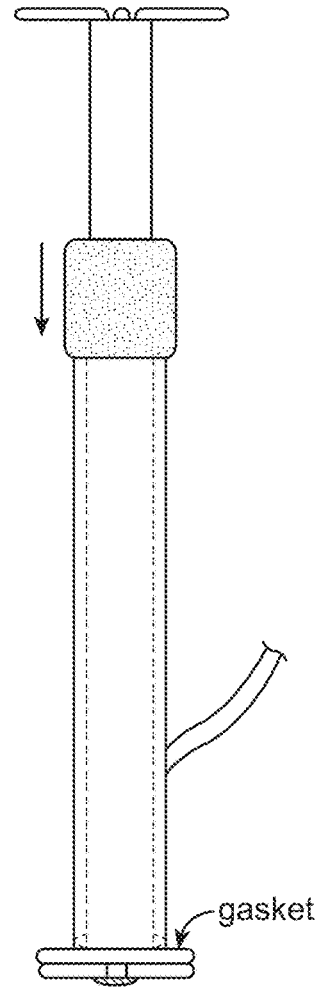

FIGS. 15A, 15B, and 15C depict operation of the inserting tool in combination with the electrode device. Once the combination shown in FIG. 15A is inserted through an incision in the dura, the surgeon controls the rotational position of the flanges 15 using the flange control rods 46 of the inserting tool, thereby deploying the flanges 15 to different orientations as shown in FIG. 15B, and anchoring the intradural assembly underneath the dura. The surgeon then slides the compression sleeve 42 down the housing 41 of the inserting tool, thereby sliding the gasket 22 down the transdural portion 31 of the electrode device to a position where it is secured by the snaps 34. As a result, the edges of the dural incision are firmly compressed between the gasket 22 and the flanges 15, preventing a CSF leak. The inserting tool is then disengaged, leaving the electrode device stably AMD safely secured to the dura.

Arrangement of Electrodes on the Intradural Assembly

To achieve some of the efficiency benefits of this invention, at least one anode and at least one cathode are positioned on or around the intradural assembly or the transdural portion, to complete the entire electrical circuit within the intradural space. Efficiency can also be gained over presently available SCS systems by using a combined electrode array or epidural and intradural electrodes, due to the beneficial location of the intradural electrodes.

Depending on the target tissue and the clinical condition to be addressed, the electrode device can be designed with more distance between the electrodes. For example, multiple electrode contacts can be positioned in a linear configuration parallel to the long axis of the spinal cord. Alternatively or in addition, multiple electrodes can be positioned along the inner surface of the dura, making it possible to deliver stimuli with electrode montages having spatial orientations that are perpendicular or at an angle of at least 45 or 60 degrees, compared with the long axis of the spinal cord. With positive and negative electrode contacts positioned in the left and right lateral positions within the thecal sac, the targeted neural tissue (the dorsal rootlets, the dorsal root entry zone, and the dorsal columns) are optimally located in the space between the contacts on either side.

Referring to FIGS. 16A to 17C, the flange arms of the intradural assembly are constructed to be longer, therefore providing more distant spacing of the electrodes. Flange arms intended to wrap against the dura at least partly around the spinal cord are generally made of a semi-rigid compliant material that can conform to the inner surface of the dura without risk of rupture, tear or abrasion. The entire flange can be made of the same material, or the part of the flange near the flange rotator can be made of a more rigid material, joined to a more compliant material further along its length. Each flange arm can be arrayed with a plurality of electrodes, optionally in a pattern that is linear, nonlinear or fractal in configuration, and with surfaces that might be nano- or micro-patterned to increase their effective area relative to the nominal geometric area. During the insertion procedure, the electrode arrays on each flange arm bend and conform to the inner arc of the dura as required. After implantation, the compliance of the flange arms accommodates changes in the thecal sac (the dural lining) that accompany normal movements of the subject.

FIG. 16A is a superior oblique view of an electrode device with an array of electrodes 14 along one of the flange arms 15. FIG. 16B is a bottom-up oblique view of the electrode device. There is one electrode 14a located on the bottom of the transdural portion 31; a second electrode 14b on the inner portion of the flange arm 15a near the transdural portion 31, and a third electrode 14c on the distal or outermost end 15b of the flange arm.

FIG. 17A shows insertion of the electrode device through a small durotomy incision. The distal portion of the flange arm 15b with the outermost electrode is inserted into the opening first, followed by the proximal portion 15a near the transdural portion. As depicted here, the implanted electrodes 14a, 14b and 14c form a one-dimensional intradural array.

FIG. 17B depicts another version where all three flanges are extended and bear electrode arrays. In the insertion position, the three flanges are oriented parallel and lie on top of each other. They are introduced into the subdural space as a bundle. After the intradural assembly is properly positioned within the dural opening and secured to the dura, two of the flanges are rotated to the deployed position. The electrodes are thereby caused to slide back along the inner surface of the dura into the positions shown.

FIG. 17C is a cross-sectional schematic depicting the location of contacts on the electrode arrays that have been rotated into lateral positions along the undersurface of the dura. With this configuration it is possible to select a wide range of stimulation geometry montages: for example, where the dorsal hemisection of the spinal cord containing all of the targeted structures is positioned in the space directly between two active contacts on either side of the spinal cord.

Other Configurations of the Intradural Assembly

The electrode devices of this invention can also be constructed without rotatable flanges on the intradural assembly. Alternatively or in addition to the flanges, there is an intradural gasket of fixed shape that has an intradural clamping surface oriented upwards in the direction of the transdural portion. The options below can be combined with any features referred to elsewhere in the disclosure with respect to other components of the device. By substantially matching the outer perimeter of the intradural gasket to the extradural gasket, the spatial gap around the full circumference of the dural opening is minimized. When the extradural compression gasket is moved into the clamped position a substantially uninterrupted watertight seal is created around the full circumference of the implanted device.

FIGS. 18A to 20D illustrate an asymmetric linear array (ALA). The intradural and extradural assemblies are elongated in shape in the manner of an oblong or ellipse, being off-center with respect to the transdural portion of the device, having a long arm and a short arm. This configuration is beneficial because it spans the incision made in the dura during implantation, thereby providing a superior seal.

FIGS. 18A and 18B are drawings of the intradural assembly and transdural portion of an ALA device. The long arm of the intradural assembly can be of any suitable length and house any suitable number of electrodes in a linear, two-dimensional, or fractal array. In a typical implantation procedure, the long arm 11a is inserted through the dural opening in the manner by which a right angle dural separator is used to access the subdural space. The short arm 11b of the intradural assembly extends a sufficient distance from the transdural portion 31 to provide an adequate clamping area to clamp the device towards the overlying external gasket.

FIG. 18C depicts an inserting tool adapted for implanting an ALA device. The positioning rod 44 is used to reversibly attach the inserting tool to the device. The compression cylinder 42 is shown in the UP position in relation to the inner housing 41. To operate the inserting tool, the surgeon compresses the extradural gasket 22 onto the electrode device assembly by moving the compression cylinder 42 downward, advancing the extradural gasket 22 past the securing snaps 34. The electrode lead 32 is positioned within a space created by aligned grooves 45 in the housing 41 of the inserting tool and the compression cylinder 42. This inserting tool has no flange control rods. As depicted here, the surface of the housing 41 (as viewed in cross-section) is oval in shape rather than circular, and the compression cylinder 42 has substantially the same asymmetric cross-section as the ALA device itself. In the clamped position, the external compression cylinder fits snuggly over the entire surface of the intradural ALA device—thereby securing the clamping surface 23 of the extradural assembly adjacent to the clamping surface 13 of the intradural assembly.

FIGS. 19A to 19D provide a top-down, or surgeon-eye view of an exemplary ALA device insertion procedure. A single linear incision is created in the dura. The length of the incision is sufficient to accommodate placement of the intradural assembly, but no longer (FIG. 19A). The long arm 11a of the intradural assembly is inserted into the subdural space using the right angle dural separator dissecting technique (FIG. 19B). Next, the intradural gasket is lifted, and dura is stretched in order to slip the short end 11b of the intradural gasket into the subdural space, similar to a button being inserted through an eyelet or the head of a rivet through its mating component (FIG. 19C). The surgeon positions the intradural assembly such that the cut edge of the dura tightly abuts the transdural portion 31 next to the short arm 11b. This results in the dural gap being positioned over the long arm 11a of the intradural assembly. There is a greater surface area available for compression of dural edges over the long arm 11a. In the final steps of the procedure, the surgeon slides the extradural gasket 22 down the transdural portion 31 where it is secured in place by the snaps 34. She then disconnects the inserting tool from the electrode device, leaving the implanted electrode secured to the dura in a watertight or leak-free manner (FIG. 9D).

Figure 20A:
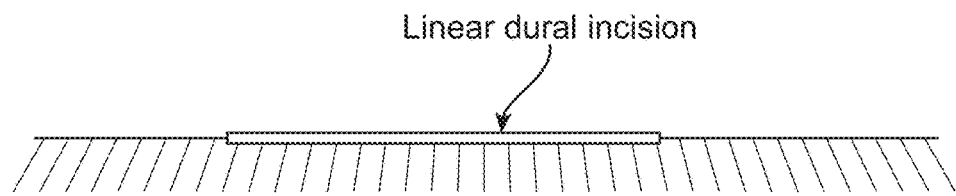
Figure 20B:
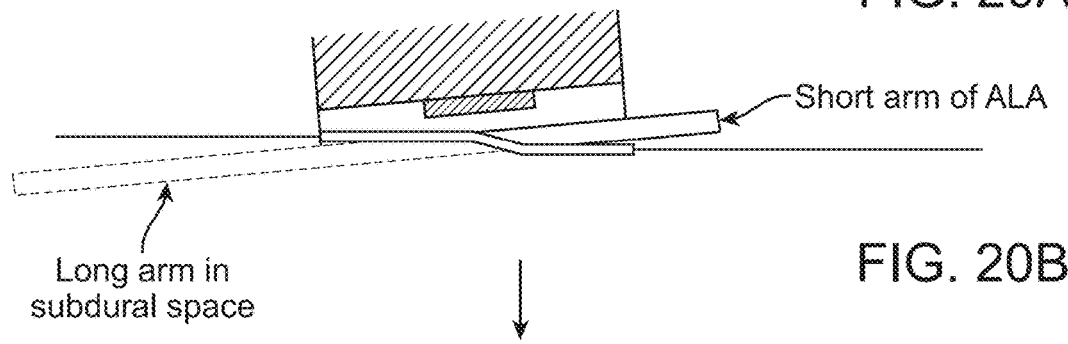
Figure 20C:
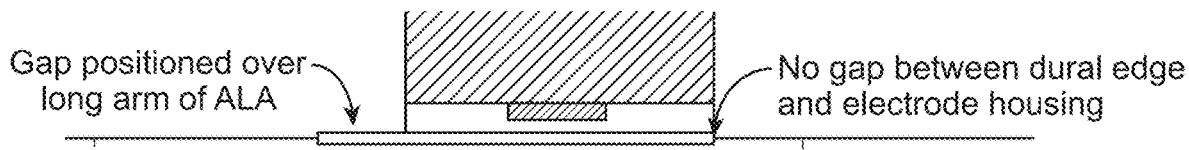
Figure 20D:
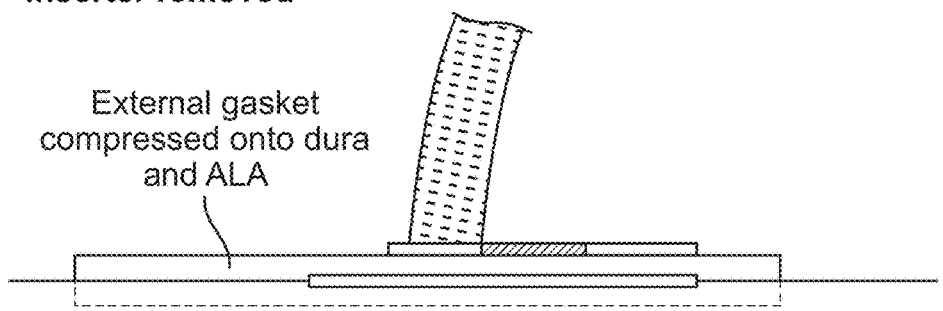

FIGS. 20A to 20D show steps of the ALA device implantation procedure from a side-view perspective. The linear dural incision (FIG. 20A) is substantially shorter than the length of the ALA device. The long arm 11a of the intradural assembly is inserted first (FIG. 20B) followed by the short arm 11b. As shown in FIG. 20C, the device is positioned in the incision such that the gap extending beyond the transdural portion 31 is located over the long arm 11a of the intradural assembly. The extradural gasket 22 is then lowered using the compression cylinder 42 until it is secured in position against the dura because of the snaps 34. Depending on circumstances, after the surgeon has exposed the spinal dura using a minimally invasive surgical technique, it is possible to perform the electrode implantation portion of the procedure in a few minutes or less.

FIGS. 21A to 24 illustrate a device designated W2, which includes another possible shape for the intradural assembly: specifically, a spiral, or an open circle or oval. This shape assists the surgeon to the intradural assembly through a very narrow incision in the dura.

Figure 21A:
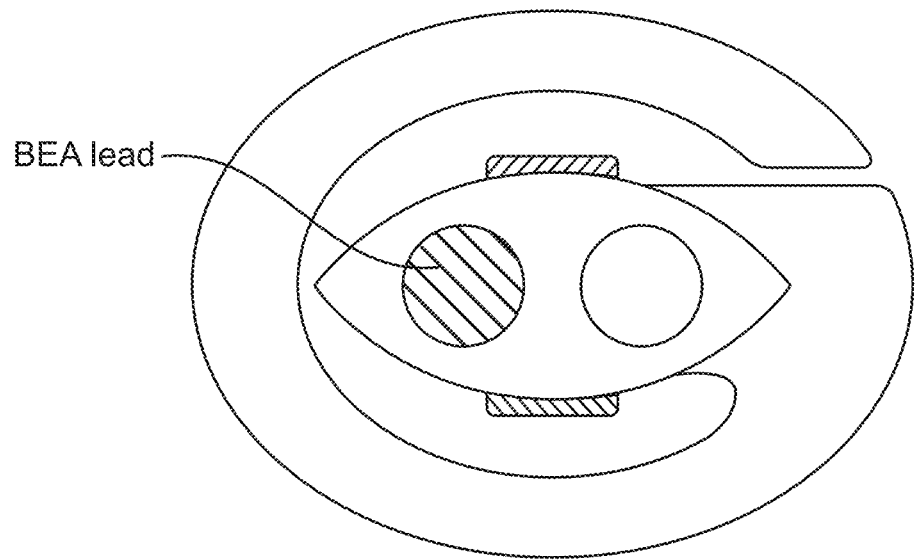
Figure 21B:
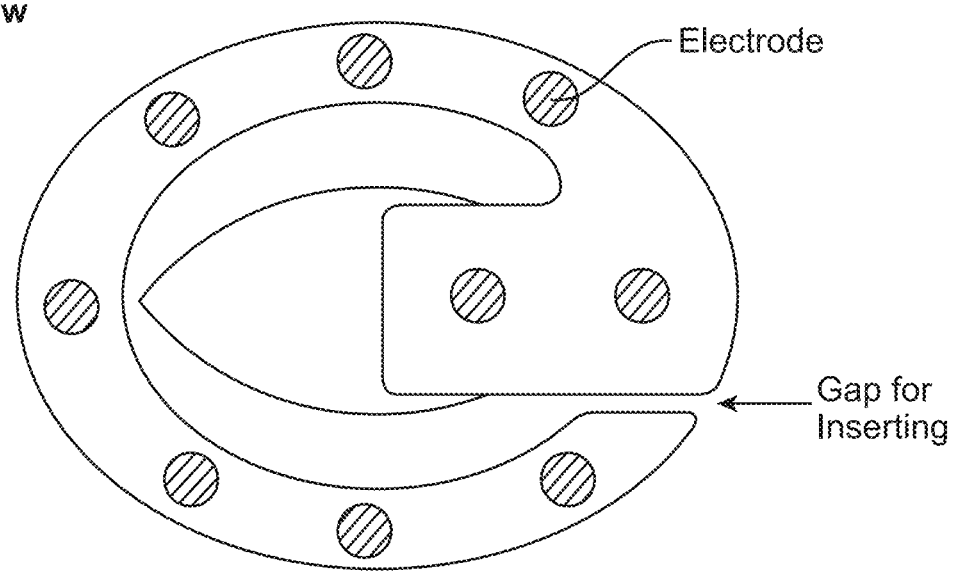

FIGS. 21A and 21B show top and bottom views of the W2 device without the extradural assembly. Multiple electrodes 14 are arrayed around the internal assembly 11, wired through the transdural portion 31 to the lead bundle 32. FIGS. 22A and 22B show side and oblique views of the W2 device without the extradural assembly. In FIG. 22A, a thin linear attachment 36 connects the intradural assembly 11 to the transdural portion 31. The attachment 36 fits snuggly within a small linear dural opening. As before, the transdural portion can be reversibly connected to an inserting tool to assist the surgeon in implanting the device into the subject. The insertion tool has a shape that corresponds or conforms to the altered shape of the intradural assembly.

FIGS. 23A and 23B show the configuration of a W2 device after insertion. The dura is compressed between the intradural assembly 11 and the extradural gasket 21. A near continuous circumferential intradural compressive surface area is created by the intradural assembly. The intradural assembly is typically rigid, so that edges of the intradural assembly on either side of the dural incision remain well aligned during insertion. This ensures that the dura spanning the gap is held in a sufficiently stable position to achieve a watertight or leak-free closure after the extradural gasket 22 has been moved down into the clamped position.

FIG. 24 depicts a possible W2 insertion procedure. A small linear incision is made in the dura, just long enough to accommodate passage of the thin linear attachment feature 36 connecting the circular electrode array to the electrode housing. The leading or free end of the intradural assembly is advanced into the subdural space under direct visualization using the right angle dural separator dissection technique. The surgeon continuously advances and rotates the W2 until it is in the final fully inserted position and seated properly. The extradural gasket is then lowered onto the dura, achieving a watertight or leak-free seal, whereupon the device is disconnected from the inserting tool.

FIGS. 27A-27F depict a device is designed to function as a port. The device includes one or more openings that are fluidically connected to the CSF and the extradural space, thus allowing for the transfer of liquid from the extradural space to the CSF. The opening(s) can be positioned in substantially the same variety of positions and configurations as those depicted elsewhere in this disclosure. For example, an array of openings can be included, or alternatively a single opening can be included. One or more valves can be included within the fluid conduit. The valve(s) can be positioned anywhere within the fluid conduit system, for example, at the location of the one or more openings or adjacent a reservoir. In some devices the valve(s) are uni-directional to prevent the movement of the CSF out of the intradural space.

The devices can be used to deliver a variety of substances, for example, active pharmaceutical ingredients such as antibiotics, analgesics, cancer therapeutics, biologics and combinations thereof. The delivery can be either passive or active. For example, passive delivery can be accomplished using various selectively permeable membranes, or active delivery can be accomplished using pressure differentials, for example, extradural syringes, pressurized reservoirs or reservoirs associated with active pumps.

Laminoplasty or Stabilizing Plate

This disclosure also provides a laminae fixation system that ensures mechanical stability of the electrode devices described herein, relative to the vertebrae and dura. With this fixation system, the electrode array is stabilized to prevent it from moving from the implanted position. The laminae fixation system maintains the electrode array in a fixed position relative to the adjacent spinal lamina when the implant is exposed to displacing forces that are generated during normal physiological movements of the body (e.g. flexion, extension and rotation of the spinal column).

Any suitable transdural electrode devices of this invention can be stabilized in vivo using a plate that keeps the device in a fixed position in relation to at least one lamina of a vertebra of the backbone surrounding or near the implant site.

FIGS. 37A to 41 show a working example of a laminoplasty or stabilizing plate and how it can be used to stabilize the electrode device in position after implantation into a subject.

Referring to FIG. 37A, the extradural assembly, comprised of polyether ether ketone (PEEK) and silicone, is oval shaped with two smooth retention arms that are used to reversibly attach the extradural element to the application tool and hold the extradural assembly in the desired orientation as the hexagonal nut is advanced along the threaded portion of the central threaded element. The extradural assembly is configured to overlap and align with the intradural assembly and the portion of the extradural assembly that abuts the dura is also overmolded in compressible silicone.

FIG. 37B shows an intradural assembly with the transdural component affixed thereto. The transdural component is a cylindrically shaped rigid central element, composed of PEEK, that serves at least two functions. The first is to encase electrode wires as they travel from the electrode contacts to the lead. The second is to serve as a mechanical purchase point for a hexagonal compression nut that is advanced along a section of the central threaded element. A portion of the left and right sides of the threaded portion of the central element are flattened (i.e. no threads) to maintain the desired alignment of the extradural assembly as it is lowered towards the intradural assembly.

In this example, the threaded components are 3 mm in outer diameter, with a pitch of 1.5 mm of travel per turn. During implantation, the surgeon closes the gap between the intradural and extradural assemblies by turning a hexagonal bottom nut that is advanced along a central threaded element affixed to the intradural assembly. As the bottom nut advances the extradural and intradural assemblies are gently drawn together until a water-tight seal is achieved.

FIG. 37C shows a prototype laminoplasty plate manufactured from grade 2 titanium. The plate shape and dimensions mimic existing laminoplasty plates used in standard spinal cord surgery, with the exception of a larger central hole to fit the transdural component of the electrode device.

FIG. 38 shows manufacturing criteria for a set of laminoplasty plates. For convenience of the surgeon, three sizes of the plate may be provided in each kit in combination with other components of the electrode device, so that the right size may be selected during implantation. From center-to-center of the screw holes, the dimensions of each plate are shown in TABLE 1.

TABLE 1

Laminoplasty Plate Dimensions

| Size | Length DIM A | Width DIM B |
|---|---|---|
| Small | 0.703 | 0.235 |
| Medium | 0.771 | 0.274 |
| Large | 0.840 | 0.313 |

The laminoplasty plate in this example may be used with standard, off-the-shelf bone screws for attaching to a vertebra following standard laminectomy surgical guidelines. Five each of two sizes of screws may be suppled in a kit with the electrode device and the laminoplasty plate, including small (1.5×4 mm) and large (1.8×4 mm).

FIG. 39 shows the electrode device fully assembled with the laminoplasty plate in place. In this example, after the surgeon has pressed the extradural assembly onto the intradural assembly using a first nut to create a water-tight seal in the dura, the laminoplasty plate is lowered over the same transdural section, and a second nut of the same diameter is screwed down the same transdural component to fix the laminoplasty plate in position against the first nut below.

Following implantation, the transdural component and exiting lead are held in a fixed position relative to the lamina, with the titanium laminoplasty plate spanning the laminectomy defect created during the operation. This approach prevents the forces that would normally be exerted on the lead body and implant during flexion and extension of the back from inducing any compressive displacement of the electrode array towards the spinal cord.

For patent purposes, the laminoplasty or stabilizing plate and its use may be characterized generally as a means for securing the device to the spinal cord. The stabilizing or laminoplasty plate is configured to be affixed to the transdural or extradural assembly of the device, and also to a vertebra of the spinal cord (typically the left and right lateral laminae) cord, thereby securing the device at a fixed position in relation to the spinal cord. As exemplified in the drawings, the transdural portion of the device extends beyond the extradural portion, exposing an external thread that is configured to receive a locking nut that screws down the transdural portion so as to secure the securing plate to the device: either against the extradural portion, or against an underlying nut used to close the extradural portion and the intradural portion together. Suitable surgical methods incorporating the laminoplasty or stabilizing plate are provided below.

For purposes of patent priority, the laminoplasty plate constitutes a separate invention that is configured for use in conjunction with a transdural electrode device as heretofore described and exemplified. This component is referred to herein as a "laminoplasty" or "stabilizing" plate for convenience, but the term does not limit the configuration or use of the component beyond what is explicitly stated or otherwise required.

Procedure for Implantation

The surgical schema for implantation, testing, commissioning and use of the invention may be illustrated as follows. A magnetic resonance (MR) scan is obtained of the thoracic spine of a patient identified as being a candidate for intradural spinal cord stimulation. The MR scan is reviewed by the clinician to determine the implantation site for the device. Under standard clinical protocols, minimally invasive surgical techniques are used to create the durotomy, implant and then secure the device such that the electrode array is positioned in a leak free manner on the inside wall of the spinal dura mater. Electrode leads are connected to an implantable impulse pulse generator (IPG) and the surgical site is then closed in the standard fashion. The IPG is subsequently programmed using standard wireless technologies.

The following description shows how an electrode device according to this invention may be implanted in a subject. This is provided by way of illustration for implanting a device according to FIGS. 11A to 11C. The procedure may be adapted mutatis mutandis for implanting other working models of the invention.

Figure 25:
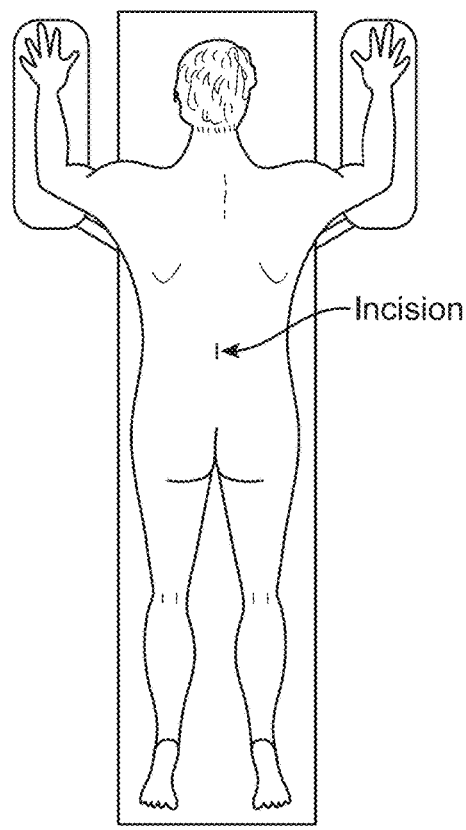

The implantation procedure is typically performed under general anesthesia. As shown in FIG. 25, the patient is positioned prone and an approximately 2-3 cm incision is made in the skin over the spinal vertebral level to be implanted. These illustrations depict the device being implanted at the T8-T9 level.

Figures 26A, 26B:
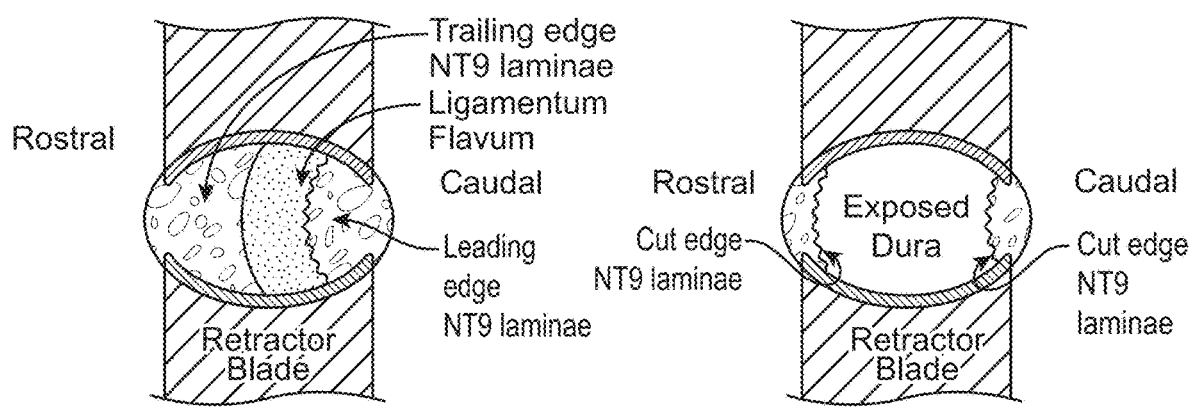

FIGS. 26A and 26B shows how the surgeon gains access to the T8-T9 laminae using standard exposure techniques. The access achieved with standard minimally invasive surgery (MIS) is typically adequate. After the retractor system is in place flush with the laminae, the surgeon uses standard MIS techniques to remove a portion of the caudal aspect of the T8 lamina, the rostral portion of the T9 lamina, and the ligamentum flavum that spans the gap between the two laminae. This results in the exposure of the underlying spinal dura.

Figure 26C:
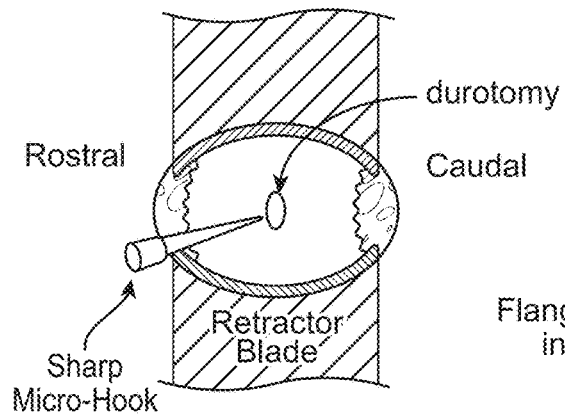
Figure 26D:
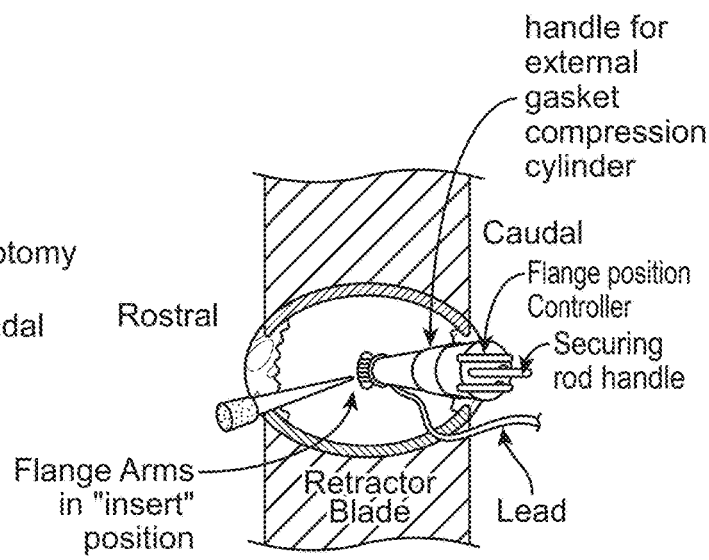

FIGS. 26C to 26F continue the procedure. In FIG. 26C, the surgeon lifts up the dura using a sharp micro-dissector and creates a small durotomy opening using the custom sharp instrument that ensures that size of the dural opening is correct. In FIG. 26D, the surgeon slips the flange control rods 46 of the insertion tool 41 into the dural opening. The flange control rods are in the insert orientation, meaning parallel and flush with each other, with the blades all facing in the same direction, corresponding to the insert or retracted configuration of the device itself. The surgeon manipulates the inserting tool using the same technique as is used with a right angle dural separator to achieve safe access to the intradural space.

Figure 26E:
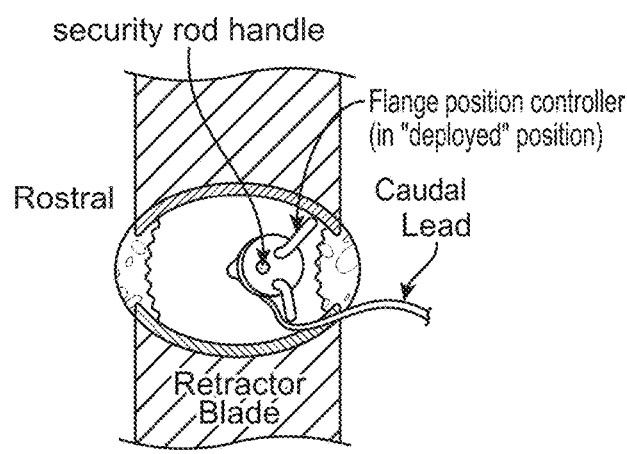
Figure 26F:
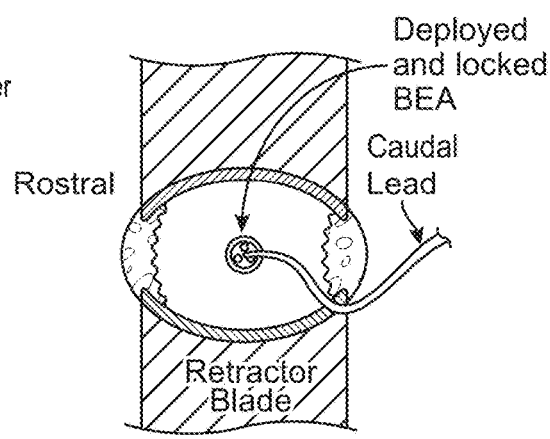
Figure 27A:
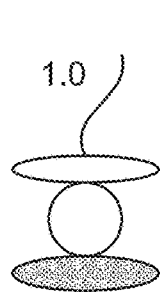
Figure 27B:
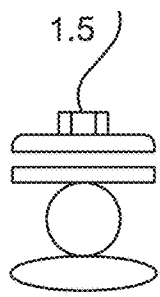
Figure 27C:
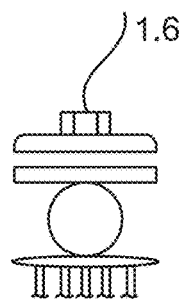
Figure 27D:
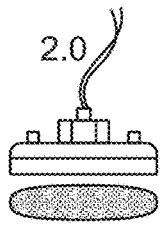
Figure 27E:
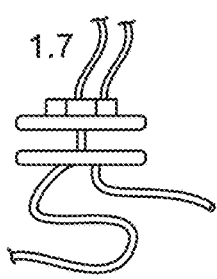
Figure 27F:
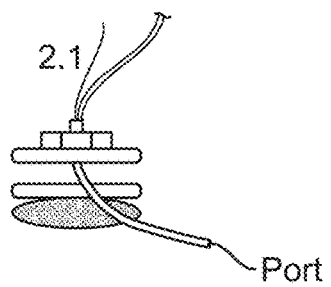

In FIG. 26E, the surgeon orients the inserting tool perpendicular to the spinal canal and rotates the two flange position controllers to move the flange arms into the deployed position. This action causes the cut dural edge to be positioned tightly around the entire circumference of the device. The surgeon then slides the handle 43 of the extradural gasket compression cylinder 42 down along the inserting tool until the gasket snaps into place, securing the device to the dura and substantially sealing the intradural space. After the device is secured to the dura, the surgeon rotates the positioning rod 44 to unscrew and disengage the electrode device from the inserting tool. The inserting tool is then withdrawn and removed from the field, as shown in FIG. 26F.

A robotic system could be used to perform some or all of these surgical steps, controlled remotely by a medical professional.

Securing the Electrode Array in Position Using a Laminoplasty Plate

Referring to FIG. 40, a suitable implantation procedure incorporating a stabilizing plate conforms largely to the common surgical approach to implanting standard paddle leads. Typically, the device is inserted through an incision in the dura and clamped in place, the laminoplasty plate is secured to the rest of the device, the lead is secured to the overlying fascia, and then the laminoplasty plate is secured to residual left and right lateral laminae.

A prototypical procedure is as follows:

A midline skin incision is created over the spinal level where the device will be implanted. The underlying fascia is incised and the paraspinal musculature reflected laterally to expose the spinous process and laminae at the planned implantation level. A laminotomy procedure is performed, and ligamentum flavum is removed to expose the dura.

An appropriately-sized titanium laminoplasty plate is positioned over the laminotomy defect and adjusted to ensure that the central portion of the plate is centered on the midline and parallel to the long axis of the dorsal thecal sac. The lead will pass through the center of the plate. The plate is then set aside and temporary dural tack-up stitches are placed to the left and right of the planned midline durotomy.

A ~8 mm midline incision is created, oriented along the long axis of the spinal canal. The applier is then used to place the intradural array through the dural defect and then secure the implant in position. The tool is designed to be used through a narrow surgical corridor of exposure and consists of two concentric rotating cylinders that are controlled independently by the surgeon using the fingers of both hands. The external cylinder reversibly interfaces with and controls the position of the extradural plate. An internal cylinder reversibly attaches to a hexagonal inner nut, and this nut is advanced along the central threaded element of the lead by rotating the internal cylinder.

The implant is mounted to the applicator with the intradural and extradural plates separated by a distance of ~5 mm. The surgeon then inserts the intradural plate through the dural defect under direct visualization. This maneuver will be similar to the standard surgical technique of inserting a right-angled dural separator under the dura when performing intradural spinal operations. The internal cylinder is rotated to advance the inner fastening nut, which closes the distance between the intra- and extradural plates, securely clamping the dural edges between the plates. After the implant is secured in position, the external cylinder is rotated to disengage the insertion tool from the implant. The insertion tool is then removed by lifting the tool away from the implant and allowing the flexible lead to slide through the central lumen of the tool.

The implant is then secured in a final stable position using the laminoplasty plate. This is accomplished by passing the lead through the central aperture of the laminoplasty plate and securing the plate to the residual left and right lateral laminae using standard laminoplasty bone screws. A second outer nut is then advanced onto the most superficially positioned portion of the treaded section of the lead until both the inner and outer nuts are flush with the laminoplasty plate. This causes the LP and lead to be held in a fixed position relative to each other as the lead nuts above and below the LP lead are brought into close proximity to each other.

After the electrode array is implanted, the lead is secured to the overlying fascia, the proximal end of the lead bundle is inserted into the Algovita™ implantable pulse generator (IPG), and the remainder of the procedure is completed in a fashion identical to that used during a paddle lead SCS operation.

FIG. 41 depicts the exemplary electrode device in the context of the tissues into which it is implanted. The laminae fixation system maintains the electrode array in a fixed position relative to the adjacent spinal lamina at the site of electrode array implantation. This fixed position stabilizes the implant against displacing forces that are generated during normal physiological movements of the body, such as flexion, extension and rotation of the spinal column.

Prototypes of the electrode device and instruments have been used to extensively test the mechanics of the implant and the insertion procedure. Five neurosurgeons have participated in the testing, and all quickly mastered the insertion technique. Using accurately scaled benchtop human spinal models and human cadavers, the procedure time required to size the laminoplasty plate, incise the dura, insert the electrode device and then secure the implant with the laminoplasty plate was less than 10 minutes, regardless of which surgeon was performing the procedure.

Digitally Controlled Signal Source

Following implantation, the device is connected to a power or signal source that is configured and programmed to deliver electrical stimulation to the spinal cord of the subject by way of the device. Any suitable signal source can be used that provides the desired intensity, frequency and duration of stimulation when electrically connected to the electrodes. The stimulation is typically controlled by suitably programmed digital circuitry, located typically in the signal source assembly.

A "signal source" referred to in this disclosure is both a source of electrical power and a digital means for regulating the waveforms of the electrical power fed through to the electrodes of the device via the leads so as to deliver spinal cord stimulation (SCS) at a desired frequency or pattern. The digital control means can be (for example) a microprocessor, microcontroller, digital signal processor, or other electronic signal synthesis and control device that is suitable for this purpose.

Optionally, the device can be configured to receive energy from a power source wirelessly. The device may include a receiver disposed along the backing of an electrode assembly. Energy can be received, for example, from a signal generator and transmitter implanted at an extradural location.

By way of illustration, the signal source can be an implantable and externally programmable pulse generator, with integrated externally chargeable battery. The subject can be given a hand held control unit capable of programming the pulse generator and recharging the battery, all by wireless telemetry link. The signal source is generally located away from the spinal cord, such as in the misculature of the lower back. The transdural implant can in principle be connected to the signal source wirelessly or using an electrical lead bundle. By way of illustration, the pulse generator can be configured and programed to deliver any one or more of the following: tonic mode stimulation (standard low frequency <1 kHz), high frequency stimulation (>1 kHz), burst mode stimulation (chirped pulse sequences or combinations of frequencies), pulse trains, noise signals, discontinuous waveforms such as square and triangle waves, and smooth waveforms such as sine waves, any one or more of these at amplitudes ranging from 10 mV or less to 10 V or more.

A signal source suitable for providing electrical signals to a subject by way of a device configured to be implanted in the dura according to this invention may be marketed with the device and implanted into a subject either separately or together.

Use of the Implanted Device for Stimulating the Spinal Cord and Treating Pain Once the device is in place, it can be used for delivering an electrical stimulus to the target region of the spinal cord. The electrical stimulus typically comprises a pattern of electrical pulses that has been predetermined or is empirically determined to provide the patient with the desired benefit. The stimulus may be applied to inhibit sensation of pain, or to inhibit symptoms or sensory input that is undesirable or disruptive to the patient, including those due to spasticity resulting from spinal cord injury or morbidities, such as Parkinson's disease, multiple sclerosis, congestive heart failure, or visceral pain. The stimulus may be provided to the spinal cord by the device on a constitutive basis, in an automatic response to feedback data, by remote control by the managing clinician, or it may be subject to the patient's conscious control.

Any effective form of electrical stimulation can be done for any worthwhile clinical purpose, without limitation. In particular, the spinal cord is stimulated so as to inhibit pain transmission by applying directly to the spinal cord an electrical stimulus that renders sensory neurons refractory to transmission of synchronous action potentials initiated within the spinal cord. This inhibits pain from locally induced sensory input, and side effects such as paresthesia that may be induced in the course of local treatment. The electrical stimulus is thought to promote stochastic depolarization of sensory neurons within the spinal cord, thus inducing a state of neural quiescence. As one example, stimulation might be used to ameliorate visceral pain by targeted, reversible neuromodulation the post-synaptic dorsal column pathway within the spinal cord.

Different stimulation algorithms can be used depending on the patient's needs. They might include tonic (standard low frequency) stimulation, high frequency stimulation, burst mode stimulation, stochastic waveform stimulation, and approaches that use special patterns or frequency combinations. Feedback can be used to monitor the excitation of the targeted neural structures, track the vital signs of the patient, and incorporate measurements or observations of the patient's posture and motor activity. Status of the equipment and its effect on the patient can optionally be monitored by the physician or other hospital personnel or caregivers via telemedicine techniques, direct connection of the stimulator to the internet or telephone network (either wired or wireless), or by any other means suitable for either one-way or two-way conveyance of stimulation parameters and settings and the patient's responses and condition.

Sensing of neural activity resulting from stimulation can be employed to optimize the response to therapy, for example, via the measurement of evoked compound action potentials (U.S. Pat. No. 9,386,934; M. Russo et al., Neuromodulation, 21:38-47, 2018). The data obtained in that manner are recorded in the epidural space and hence are far-field in nature. However, by intradural placement of the electrode array per the means and method of the present invention, sensing of the evoked compound action potentials becomes nearer-field in nature. This has a number of potential advantages, including less uncertainty in the isolation and identification of the target neural elements, less risk of movement of the sensing electrodes relative to the target neural elements, and improved signal-to-noise ratio.

The therapeutic dose of current density into the targeted neural structures can be titrated, ramped or otherwise made adjustable for the purpose of optimizing therapeutic benefit to the patient. Current densities at any level within those approved by the U.S. Food and Drug Administration (FDA) for safe and efficacious delivery of SCS therapy can be used.

The device is configured so that the treating clinician can at her option apply spinal cord stimulation using a voltage that alternates at high frequency. Regardless of the way the potential may vary over time, the frequency may be calculated by determining the number of positive-to-negative alterations per unit time. Effective frequency ranges depend on the anatomical placement of the electrode array, the features of the array, the nature, health, and electrophysiological characteristics of the tissue where the array is placed, and the objectives of treatment. The general object is to induce refractoriness of the spinal cord to transmit deleterious signals or synchronous depolarization events initiated locally. This can be adjusted empirically by determining neural activity and recording the symptoms experienced by the patient.

Depending on the objective of the treatment and the manner in which the technology is deployed, effective pulse repetition rates or frequencies may be at or above 100 Hz (pulses per second), 200 Hz, 500 Hz, 2,000 Hz, or 5,000 Hz, a frequency of about 1,000 Hz, 4,000 Hz, or 10,000 Hz, or a frequency range of about 500 to 50,000 Hz, 1,000 to 9,000 Hz, 3,000 to 8,000 Hz, 2,000 to 20,000 Hz, or 5,000 to 15,000 Hz.

The electrical stimulus may be adjusted in frequency or other waveform parameters, and manner of application so as to minimize side effects such as paresthesia, and to minimize impact on transmission of essential neurological faction, including motor neuron activity, and nerves involved in proprioception, kinesthesia, and either cognitively controlled or autonomous bodily functions. Optionally, the clinician or the user may be provided with an input means to select the pattern, adjust the frequency, and adjust the intensity in accordance with the perceived symptoms and standards of practice.

The electrical potential may vary at a regular frequency in a sinusoidal or square waveform. Alternatively, the waveform may be a more complex charge-balanced pattern, with pulses appearing at varying intervals and intensities according to a calculated, repetitive, or random pattern. Such patterns comprise a pulse train generating substantially continuous activation of nerves within the spinal cord, and may incorporate irregular pulse intervals, irregular pulse amplitudes, a variety of wave forms (for example, monophasic, biphasic, rectangular, sinusoidal, as well as asymmetric or irregular wave forms), or any combination thereof. The potential may also create what is essentially a broadband noise, varying at stochastic or essentially random intervals and intensity under the influence of a suitable computational algorithm or automated control program in the digital circuitry of the signal source.

The electrodes through which the high-frequency stimulus is conveyed are typically arrayed on a pliable background, constructed of a material and in a shape that allows it to be conformed directly to the morphology of the spinal cord. Optionally, the technology may be configured to apply different stimuli through different electrodes of the device, and to actively control the polarities of the individual electrodes within the array Treating pain according to this disclosure can include administering an electrical stimulus to the spinal cord, monitoring transmission of synchronous action potential through the spinal cord and/or pain experienced by the subject, and then adjusting the electrical stimulus so as to further inhibit or otherwise regulate transmission through the spinal cord of synchronous action potentials. The object may be anything that is clinically worthwhile, such as reducing sensation of pain (especially back pain) by the subject, such as may occur in the course of spinal cord injury, disease or strain of the spinal cord, Parkinson's disease, osteoarthritis, or congestive heart failure.

Use of the Implanted Device for Treating Spasticity

From 68% and 78% of patients with spinal cord injury suffer from spasticity—about 200,000 persons in the U.S. alone. Spasticity can also arise from an upper-motor neuron syndrome such as multiple sclerosis and stroke: the leading cause of disability in the United States, with an estimated 5.4 million affected patients. About 50% of patients who have experienced a stroke suffer from long-term disability and require the assistance of caregivers for daily living. About one-third of the 30 to 500 per 100,000 population with a history of stroke suffer lower limb spasticity, many of whom need medical intervention Conditions where spasticity features prominently include cerebral palsy, multiple sclerosis (MS), ischemic or hemorrhagic stroke, trauma to the brain, and spinal cord injury (SCI). Patients with long-standing spasticity are limited by pain and contractures that interfere with activities of daily living and hamper rehabilitative efforts. Although pharmacological and surgical treatments are available to reduce symptom burden, these therapies are neither curative nor restorative, and offer only partial or no selectivity. Although there have been preliminary attempts to treat spasticity with epidural spinal cord stimulation, the results have been equivocal given the limitations of the technology.

This invention includes direct SCS as an alternative approach to standard epidural spinal cord neuromodulation. It is superior to technologies currently being used commercially, because it directly activates the neural circuits that regulate spinal motor neurons. Much greater targeting selectivity of neural structures can be achieved by placing the electrode array intradurally. This is possible even at much lower stimulation amplitudes. An SCS device of this invention can co-opt and electrically integrate with targeted zones of the spinal cord to modulate a limited number of selected motor neurons—say those around the L3 segment. Stimulation interference paradigms may also play a role. Once the therapeutic effects are established in each patient, the treating clinician may toggle the stimulation controls selectively to first treat spasticity, and then to scale up with more sophisticated programming.

Treating spasticity according to the invention can include administering an electrical stimulus to the spinal cord, monitoring transmission of synchronous action potential through the spinal cord and/or symptoms of spasticity being experienced by the subject, and then adjusting the electrical stimulus so as to further inhibit or otherwise regulate transmission through the spinal cord of synchronous action potentials and/or signals of excessive velocity-dependent muscle contraction that result in the symptoms of spasticity. In a closed-loop configuration of the type suggested here, the therapeutic response will be optimized by virtue of the intradural location of the stimulator's electrode array, and also by the possibility of employing a combined epidural/intradural sensing method for measuring the evoked compound action potentials associated with the response to stimulation.

Dosing of Stimulation

The technology of this disclosure can be used to cause a disruption in the synchronous firing of axons, or a portion of axons within a nerve bundle. The disruption can be controlled by increasing or decreasing the frequency and/or power of the stimulation. A high frequency stimulation can be used to induce pseudospontaneous firing (random axon firing commonly associated with a state of non-sensory stimulation) thus causing the patient to not perceive pain. In some methods described herein the frequency can be set such that stimulation is provided at a frequency that does not allow sufficient time for some, or all, of the axons in a nerve bundle to reestablish their membrane potentials.

The frequency and power used to provide a therapeutic benefit will vary from patient to patient and that adjustments to the devices disclosed herein can be made using feedback from the patient or sensors included to identify and subsequently generate and control the optimum stimulation. By way of illustration, a patient can be initially started on one therapeutic stimulation dose or regimen, and over time as the patient adapts to the dosage, a new dose or regimen is prescribed and applied.

Rationale for Using High Frequency Stimulation

The following discussion is provided as an educational perspective for the reader, and to help advance the art. It should not be interpreted as imposing any limits on the practice of the invention, except where explicitly stated or otherwise required. The reader may implement and advance the devices and methods of this invention without understanding or proving any of the phenomena propounded here.

High frequency stimulation of the spinal cord may benefit the patent by inducing a state of pseudospontaneous axon firing. Bundles of sensory axons are thought to fire randomly when not transmitting sensory stimulus. When a sensory stimulus is presented, a substantial proportion of the axons within a bundle or pathway discharges in a synchronous fashion—firing axons potentials at about the same time. This results in the sensory input being transmitted along the axons in the bundle, so that the subject may experience the sensation. Stated differently, the absence of sensation is coded by random timing of axon firing within a bundle, whereas a sensory perception is coded by synchronous firing of a population of axons.

It is a hypothesis of this disclosure that patients with leg and back pain have bundles of axons spontaneously firing in a synchronous manner (or some other non-random fashion), instead of the normal random pattern of firing. Electrical pulses entrain axonal firing. A single pulse delivered to a bundle of axons will cause them all to fire synchronously. If the time interval between each electrical shock in a pulse train is longer than the refractory period of the axons in the bundle, each subsequent shock will also synchronously activate all of the axons, and the patient will experience a sensation. A low frequency alternating current applied to the back (50 Hz) may be effective in reducing the sensation of pain, but the stimulation may generate neurological side effects such as unwanted paresthesias (tingling or numbness).

A high frequency electrical stimulus (say, about 5,000 Hz) has interval spacing shorter than the refractory period of axons. An individual axon cannot fire again in response to a second shock until its membrane potential has recovered from the effects of the first shock, and this takes time. Different axons have different refractory periods. By delivering electrical pulses at high frequency, the relative timing of firing by individual axons within the bundle of axons becomes nearly random, with different axons become excitable again at different times.

Applying high frequency pulses to the spinal cord can be used to restore a state of active quiescence in the sensory nerves passing through the cord. This can inhibit transmission of undesired signals through the spinal cord, such as a sensation of pain in the spinal cord or extremities, or excessive muscle contraction signals that result in spasticity.

Definitions

An "electrode device" of this invention may be variously and interchangeably referred to as an electrode assembly or a button electrode assembly. Particular examples may be referred to by the mark I-Patch™, I-Patch 2.0™, or IP2™. These terms refer to the medical device that is configured for implantation in the dura of a subject, either in the open position or the clamped position, with or without an inserting tool. Flanges or other deployable features if they are present may be in the insert position or in the deployed position. Unless otherwise stated or implied, the signal source and the inserting tool are referred to and characterized separately, when used either separately or in combination.

The "intradural assembly", the "extradural assembly", and the "transdural portion" of the device, when present, refer to components of the device that have the structure and perform the action with which they are defined. They do not need to be in any particular physical space, either before or after implantation. After implantation, the intradural assembly is not required to be positioned entirely under the dura, the transdural portion is not required to go entirely across the dura, and the extradural assembly is not required to be positioned entirely outside the dura, unless explicitly stated or otherwise required. Similarly, a "gasket" is required only to do the function indicated, and may be made of any suitable material.

The terms "positioning tool" or device and "inserting tool" or device are used interchangeably to refer to an apparatus or part of an apparatus that is used by the surgeon while the combined electrode assembly is being implanted into the patient, and is then withdrawn from the surgical field for reuse or disposal, leaving the electrode assembly in place. In accordance with what is claimed, the positioning tool is not necessarily included with an electrode assembly of the invention. For industrial applicability, the positioning tool may be supplied in combination with the electrode assembly, or it may be supplied separately and combined with the electrode assembly together in the operating theater. An electrode assembly of the invention may be implanted using a positioning tool of the invention, or with any other equipment that the surgeon deems suitable.

"Quiescence" as the term is used in this disclosure in reference to a bundle of axons refers to a condition of stochastic depolarization or firing of axons within the bundle. It is a natural condition in which the neurological system may be actively signaling that there is no sensory input to be transmitted by the bundle as a whole. It may be induced by pseudospontaneous neural stimulation by applying effective high-frequency electrical pulse patterns in an appropriate manner as described here.

When different components of a device or tool of this invention are described in shape (such as cylindrical, round, or oval) or in a position relative to another component (such as parallel, or perpendicular), or in comparison (such as being the same shape or complementary), such terms are approximate, unless explicitly indicated otherwise. The actual shape or position may deviate from the exact shape or position referred to within the functional tolerance of the configuration without departing from what is described or claimed. When different components of a device or tool of this invention are referred to positionally, such as a vertical or longitudinal axis, this is done to help orient the reader: it does not require any particular position or orientation of the device when sold or in vivo.

EXAMPLES

Example 1: Testing of Various Gaskets for Use with Intradural Stimulator

Figure 10:
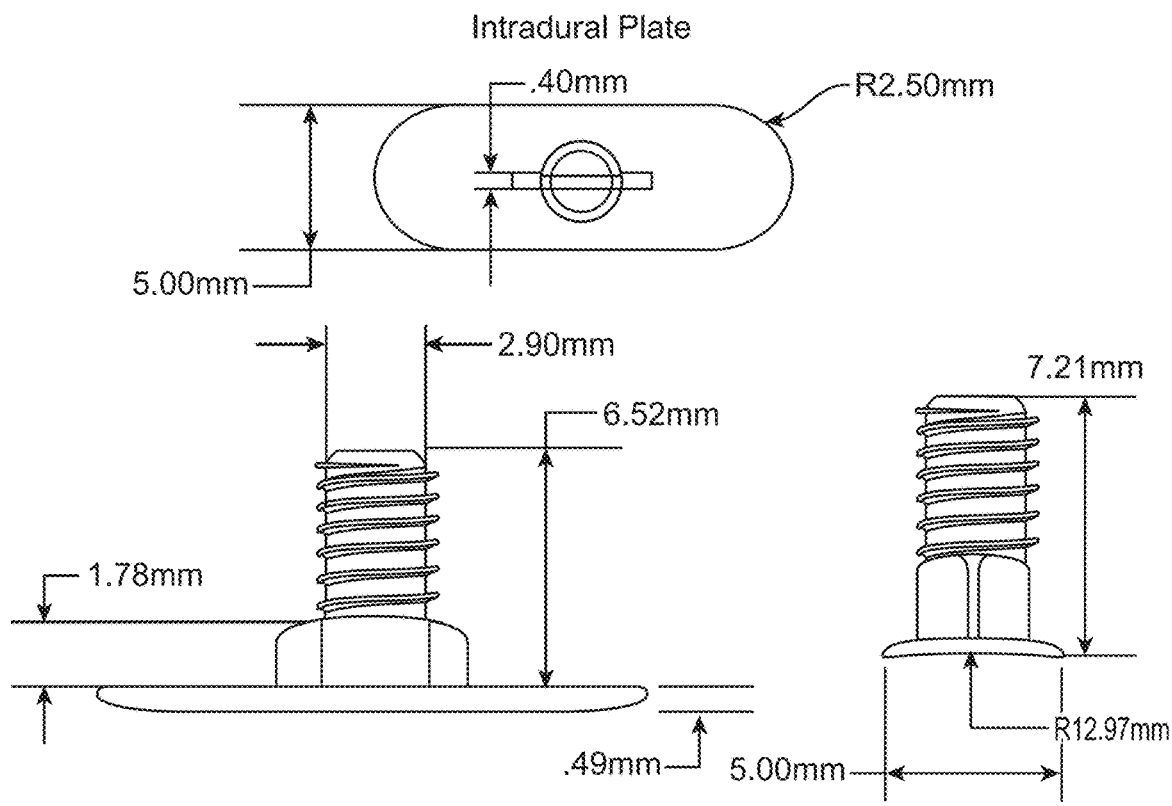

To test the workability of the gaskets as seal mechanisms against leakage of CSF, the compression plates and housing of the prototype intradural stimulator of the type shown in FIGS. 1 through 4 were implanted into a mock durotomy slot that had been cut into a Plexiglas® tube which simulated the thecal sac. A thin, smooth strip of polyethylene was used as the surrogate dura mater to insure that any leakage pathways would be associated only with the gaskets and not with porosity of the dural surrogate. The gaskets between the compression plates were made of Durepair®, which is a dura substitute often used to close and seal durotomies. The gasket thickness was nominally 0.5 mm, and of oval shape with length and width matching the dimensions of those of the intradural plate as shown in FIG. 10.

A syringe was connected to one end of the Plexiglas® tube and the other end was blocked shut. The tube was filled with water, with the hydrostatic pressure controlled manually by the force acting on the plunger of the syringe. A pressure meter was used to monitor the hydrostatic pressure within the tube, which could be increased to super-physiological levels. A durotomy slit was cut in the polyethylene strip and the stimulator assembly was implanted, with the Durepair® gaskets on either side of the strip. The compression nut was then gently tightened to draw the intradural plate and extradural plate towards each other and produce closure of the durotomy, and the syringe was thereafter used to raise the hydrostatic pressure. The seal produced by the gaskets remained leak free at the maximum applied pressure of approximately 250 mm Hg, which was several times the peak intrathecal pressure observed in patients during a change of posture. This demonstrated the workability of the gaskets as seals against potential post-implantation CSF leaks.

An additional point of interest has to do with the dynamics of the prototype's sealing mechanism. The surface area of each gasket, A, is approximately $25 \times 10^{-6}$ m$^2$, and from standard engineering models we estimate that the closure tension, F, exerted on the gasket by the compression nut is approximately 1.1 N. Hence, the pressure, P, acting on the gaskets within this assembly will be $P = F/A = 1.1$ N$/(25 \times 10^{-6}$ m$^2) = 4.4 \times 10^4$ Pa$\approx 330$ mm Hg. That pressure is about 33% larger than the peak pressure that had been applied to the gaskets in our test, and it is roughly 15 times larger than normal intrathecal pressures, hence providing additional insight into the leak-free performance of the seals as observed in our experiments.

Example 2: Modeling of T Shaped Electrode and Selective Fiber Stimulation

The modeling described herein indicates that the intradural stimulation device can be used effectively to modulate targeted neural elements selectively within the spinal cord, while at the same time sparing non-targeted structures. Moreover, modeling, such as described in this Example 2, can be used to determine additional configurations of the intradural stimulation electrode array that can be used to selectively stimulate neural structures, such as for example, large fibers, small fibers, medium fibers and combinations thereof. At the most elementary level this means controlling or steering the electrical fields generated by the currents delivered from the electrode contacts; this usually involves both spatial and temporal control attributes. The spatial distribution of the field strength and gradient determines which neural elements are affected. Current flow through the axons passing into these fields may be susceptible to exogenously triggered depolarization. The temporal pattern of the fields also will influence the axonal action potentials. From this summated response to the field strength and temporal application emerges the 'selectivity' and the desired modulation of neural activity.

COMSOL Multiphysics® (a general-purpose simulation software for modeling designs, devices, and processes available from COMSOL, Inc., Burlington MA) was used to solve for electrical fields and currents over axial and transverse segments of the spinal cord deep to the dural membrane. Data and graphics were exported for illustration and use by MATLAB®-based programs that reconstruct complex fields and simulate the effect of the fields on axons of various sizes within the dorsal column.

FIG. 28 is a schematic diagram of the intradural stimulation system with auxiliary epidural lead(s). FIGS. 29A and 29B are renderings of an exemplary version of the implantation tool and intradural stimulator. After the dura is opened, the surgeon uses the tool to insert the electrode array within the thecal sac. The inner shaft of the tool gently tightens a closure nut onto the surface of the extradural compression plate. This clamps the dura between the gasket materials on either side of the compression plates and secures the electrode array in place. The outer shaft of the implantation tool is then rotated to release it from the opposing tongue-and-groove joints on the extradural plate, and removed. The lead bundle is connected to one channel of the pulse generator, and as suggested schematically in FIG. 28, an auxiliary epidural cylindrical lead implanted at the same time is connected to the other channel, thus completing the procedure.

The scale and contour of the intradural electrode array is matched to that of the adult spinal cord. For example, there can be a concave side and a convex side and the electrodes that contact the CSF can be mounted on the convex side while the concave side directly, or indirectly through another layer, abuts the inner dura. The features of the human spinal cord captured in geometry for computational purposes are shown in FIG. 30. For our simulations these included (1) a gray matter core, (2) white matter surrounding the gray matter, (3) a CSF layer bounded by the spinal cord and the dura, and (4) the dura itself, which is the outer layer of the model. Also per FIG. 30, an electrical conductivity is assigned to each volume and the dural interface with an external ground. All the conductivities are scalars apart from that of the white matter, which has different longitudinal and radial conductances. Electrical continuity is assumed between each volume. It is further assumed that electrical activity outside the dura is small with respect to internal activity. The cross section of the cord was held constant over the 80 mm of cord simulated. The substrate holding the twelve sites is positioned just beneath the dura and projects 0.3 mm below the dura.

Internal Physics and Boundary Conditions

The continuity condition for zero charge creation ($\nabla \sigma \nabla V = 0$) holds everywhere in the model interior, all surfaces at the ends of the cord have zero potential (V=0), the outer elliptical surface representing the dura is conductive with a zero reference $$\text{Voltage}(n \cdot J = \frac{\sigma}{d_s}(V - V_{ref})$$

and the sites are current sources such that: $\int_{\partial \Omega} J \cdot n ds = I_0$. The actual distribution of the current over each site is determined by the surrounding electrical environment. V is the dependent variable representing the internal scalar potential Voltage, $\sigma$ is the conductivity scalar or tensor, $d_s$ is the dura thickness and J is the current vector ($J=-\sigma \nabla V$).

The geometry and boundary conditions are used to solve the electrical fields. This is done by discretizing the volume of the model with tetrahedral meshing and then employing the finite element method, both of which are implemented within COMSOL®.

Field Evaluation

Several post-processing methods are available within COMSOL to produce important data products from the field solutions. Among these are visualizations of the fields and currents superimposed on the geometry, calculation of quantiles such as maximums, minimums, averages, integrals etc. over points, lines, surfaces or volumes, and export of any of the products.

Basis Function Method for Field Reconstruction

When performing many serial computations on fields under different drive conditions, it is convenient to use a basis method to reconstruct each new field dictated by new boundary conditions. This is accomplished by solving the model for each site excited alone with a unity current (1 mA) while the other sites are set to zero. A complex field generated by several sites with different currents can be approximated accurately by superposition of the basis fields scaled by the current from that site. This method was used when computations such as neural simulation were performed using the MATLAB platform outside COMSOL. This method is justified by the fact that the model is linear.

Neural Models

There are several variations of models for propagation of neural spikes in myelinated axons and how electrical field potentials can initiate them. The minimum construction is string of nodes consisting of a capacitive membrane populated by simulators of different voltage-controlled channel species for Sodium and Potassium and held at an equilibrium potential by diffusion potentials. The nodes are then capable of an action potential upon sufficient depolarization of the membrane. When the nodes are connected by conductive and perfectly insulated axonal interiors, it is then possible to propagate action potentials from one node to another through depolarization of adjacent nodes by action potential-driven currents.

The triggering mechanism is the following. Electrical stimulation causes initiation of the first action potential by positive second potential differences external to nodes. This will drive the currents causing depolarization of a single node or group of nodes within the influence of a sufficiently strong second difference. Thus, both field strength and field shape are important for initiating action potentials. For example, a constant field potential or a constant potential gradient cannot initiate an action potential in an axon. FIG. 31A is a view from under the pia surface. The pia and a cross section plane are colorized with a representation of the potential field. In addition, lines parallel to the axis of the cord are inserted to mark locations of waveform samples shown in FIG. 31B. These spatial waveforms clearly show a positive second spatial derivative or difference.

From this minimally complex axon model, several features can be added which increase the fidelity of the simulation. These include better models of the myelinated axon by adding piece-wise cable properties to the conductive segments and more refined populations of channels to the nodes, among others. For instance, the McIntyre-Richardson-Grill (MRG) model separates the membrane/myelin lumped circuit into membrane leakage and capacitance in series with a myelin leakage and capacitance (McIntyre C C, et al., J Neurophysiol 2002; 87(2):995-1006). In addition, a conductive space is added between the membrane and the myelin and this network is often distributed into several networks along the internode. This model adds two differential equations per internode network, which may be repeated as many as ten times.

Illustrations

FIG. 32. shows isopotentials in the white matter where fibers of different fiber size classes are excited. As current is increased from the top graphic to the bottom and the proportion of current required from the tip sites increases, the contour lines get more curved and the axon excitation extends to greater depth.

FIG. 33 shows almost identical stimulation profiles are seen to progress across the cord in the images from top to bottom on the right. At the top, a 1.4, 0, −3, 0, 1.4, 0 current pattern is expressed. The pattern of stimulation progresses linearly until a [0, 1.4, 0, −3, 0, 1.4] current program is achieved at the bottom. The power (P) is shown for each case.

FIGS. 34A to 34C show that during stimulation pulses, electrode sites over the intended target deliver a cathodic depolarizing pulse sending some nodes of neurons into action potentials followed by propagation of the action potential in both directions. In the recovery stage, an anodic pulse of longer duration and reduced magnitude performs the required charge balance. To achieve the focusing effect to avoid stimulation of off-target tissue, anodic first pulses are delivered peripheral to the central electrode sites. A well-designed pulse, (b), prevents spread of the target area and does not induce an off-target action potential. If the recovery (cathodic) part of the anodic first pulses has too large a magnitude, (c), an unintended discharge and propagation is possible.

FIGS. 35A to 35C show a circular electrode site having identical area to the sites used in the device described with similar interface impedance was driven with a 200 μs cathodic pulse followed by a 50 μs pause and a 400 μs charge balance phase. (a) The drive and the interface voltages show a step at the beginning of the pulse followed by ramping down until the end of the cathodic pulse. The average interface voltage increases because the current distribution later in the pulse is less efficient. The difference between the drive voltage and the interface voltage is accounted for by the charge accumulated on the surface of the site and the difference in current distribution as the phase progresses. (b) The current distribution across the site is shown from just before the start of the cathodic pulse to just before its end. At the beginning of the pulse, the current at the edge of the site spikes to a level well above that of the site center. As time passes, the current distribution becomes more uniform. (c) Interface voltage is shown for the same times as in (b). This negative potential increases in magnitude as explained above but also is lower at the edges due to the accumulated charge.

FIG. 36 shows current distributions are shown for sites and the pia surface of the white matter at the instant the cathodic stimulation phase is started. The current on the site edges are very large with respect to the average current but this quickly disappears as the charging of the site progresses. The current passing in and out of the white matter is much less than the current at the sites because of the shunting effect of the CSF. While the total current at the cathodic sites is 4 mA, the current passing into the white matter is only 0.13 mA or 3.25%.

Results: Tissue Targeting and Selectivity

The flow of current from any single site on the implant will spread preferentially in the CSF because it has the highest conductivity of any media in the model, for example, ~20 times the lateral component of the white matter conductivity tensor. The equipotential lines seen in the gray and white matter of the spinal cord tend to be straight lines therefore cutting across not only the white matter but also the gray matter leading to unintended stimulation of cells in the gray matter. The T electrode or T referred to herein refers to an electrode having an array, wherein the array contains electrodes that can be used in a T shape as shown in FIG. 29B. The solution is to excite central sites of the implant with a cathodic potential while exciting lateral sites on the tips of the T with an anodic potential. This limits the cathodic potentials from spreading laterally, thus missing the dorsal horns of the gray matter. FIG. 32 illustrates this for four different current levels in the central two sites of the T. With greater central cathodic current, a greater proportion of anodic current from the tip sites is required causing the power consumption to increase approximately quadratically.

As with achieving greater stimulation depth, currents from sites on the T can be manipulated to move the effective stimulation zone horizontally across the cord. FIG. 33 illustrates how sweeping of current sources across the T can position the center of stimulation with high spatial resolution. Four steps are shown but more instances can be placed within the progression thus creating an increased resolution of position. The linear step method utilized to achieve progression of the stimulation center across the cord can be diversified considerably to gain greater depth and perhaps a more skewed pattern by departing from the symmetry of the montage as practiced in the example.

When shaping the stimulation field, we can constrain the cathodic pulse to a target area but the electrochemistry of the electrode sites requires that there be a recovery phase of the stimulus waveform that charge-balances the net stimulation to zero. This means that the tissue volume not included in the target will receive a cathodic current during the recovery phase that may excite neurons in an unintended volume. The method that is usually used makes the recovery current much smaller than the stimulation phase over a longer time. The requirement for this factor in the stimulus design may limit the depth and selectivity strategy in some cases. FIGS. 34A to C illustrate this challenge.

Electrically bypassing the dura is a large power saving amounting to 75% due to the large impedance with respect to the subdural structures. This feature can result in longer battery life. In addition, the subdural device projects slightly into the CSF space bringing the electrode sites closer to the excitable elements of the white mater and thus less current spread within the CSF. This better proximity improves the ability to steer or focus the electrical potential within the white matter. Independent of the reduced impedance barrier and improved proximity curving of the iso-potentials needed to obtain selectivity and improved depth. FIG. 32 shows improved depth by passing more current through the central sites and the tip sites of the T cross. For the improvement of depth obtained from no tip involvement to maximal tip involvement there is an 1800% increase in power placing a stress in the site electrochemistry and the tissue near just under the pia mater. To determine the limits, a safety analysis is required: the tissue's tolerance to current density and total charge per pulse-phase, and prevention of electrode failure.

Site corrosion can lead to failure of a device and poisoning of the target tissue. The electrode sites used in the IP 2.0 are small by the standards of dorsal column stimulation devices. This is justified by the proximity of the sites to the target tissue and the absence of the impedance and distance barrier presented by the dura. The area of the sites is 1.72 mm$^2$ and the accepted safe charge delivery per phase for platinum is 50 μC/cm$^2$ yielding 0.86 μC as the charge limit per phase for the T-array site. The value of 50 μC/cm$^2$ refers to the threshold for the onset of neurological tissue damage. Thus, for a 200 μs pulse, the largest current allowed is 4.3 mA. It is also assumed that the capacitance of the site surface is 0.45 F/m$^2$ although it may be assumed that materials with higher effective capacitance could also be used for this application.

An example pulse sequence consisting of a 200 μs cathodic phase of 2 mA followed by a 400 μs anodic phase at 1 mA uses about half the capacity of the site. The voltage required to execute this charge balanced pulse sequence is shown in FIG. 35A for a circular site of the same site area used in the full cord model. The average interface voltage and the drive voltage are equal as the sequence starts but diverge as the site becomes charged. In the anionic phase, the graphs converge again ending when charge balance is achieved. The details of how the electrode current and charge profiles evolve as a function of time and radius are show in FIGS. 35B and 35C. As the sequence begins, the drive voltage jumps to overcome the spreading resistance then ramps downward due to (1) the increased average charge across the site and (2) to lower efficiency of charge transfer resulting from greater charge at the periphery.

This rapid accumulation of charge at the site edge results from increased current flow there as is shown in the FIG. 35B. If the sites and pulse protocols are not designed to control edge currents, site corrosion can occur. During the first few microseconds of a pulse, the imbalance between center and edge current can be somewhat extreme, but as time progresses, the current density across the site becomes more even. At the end of the cathodic phase, the potential difference due to extra charge at the edge is about 100 mV. The magnitude of the edge current at the beginning of the pulse can be reduced by several ways. (1) Keeping the curvature of the site perimeter to a minimum is important. Circular sites are the most efficient when used alone. (2) Shaping the pulse's leading edge to have a longer rise-time allows charge to build up more slowly, thus reducing the maximum current density at the edge. (3) Preventing adjacent sites from having extreme polarity differences will prevent large currents from flowing directly from site to site. Evenness of this current is promoted by parallel edges of adjacent sites. This is another cost of target selectivity. (4) Adding a resistive layer over the site forces the current flow and thus be more evenly distributed, but at the cost of additional power because of the resistive voltage drop and a less efficient current flow into the media.

FIG. 36 shows an example of the current distributions for the sites and the pial surface of the white matter at the instant the cathodic stimulation phase is started. The pial surface current density distribution changes minimally over the charge injection pulse because of the gap between the site and target, but the current distribution on the sites changes considerably as described above.

None of the examples used in this Example 2 exceed the 50 μC/cm$^2$ limit. Similarly, there are limits of current density which can be tolerated by neural tissue. The maximum current density seen in our maximum depth of excitation figure is 1.33 mA/cm$^2$, which for the 200 μs pulse is 0.266 μC/cm$^2$, well below an accepted boundary of 30 μC/cm$^2$.

Prior U.S. Pat. Nos. 9,364,660, 9,486,621, 9,254,379, 9,572,976, 9,403,008 and 9,950,165 are hereby incorporated herein by reference in their entirety for all purposes, including but not limited to the description and elaboration of SCS device components that may be included or excluded from any of the embodiments of the SCS devices and their use described and claimed herein.

Each and every publication and patent document cited in this disclosure is hereby incorporated herein by reference in its entirety for all purposes to the same extent as if each such publication or document was specifically and individually indicated to be incorporated herein by reference.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed.

The invention claimed is:

1. A device for spinal cord stimulation, configured for securing to the dura surrounding the spinal cord of a subject, the device including the following components:
   a plurality of electrodes;
   wire leads configured to electronically connect the electrodes to a signal source outside the dura; and
   a means for securing the device to the dura such that the electrodes are in direct contact with the cerebrospinal fluid (CSF) within the subdural space but not in direct contact with the spinal cord itself.

2. The device of claim 1, configured for traversing and securing to the dura surrounding the spinal cord of a subject, wherein the device includes the following components: a transdural portion;
   an intradural assembly; an extradural assembly; a plurality of electrodes on the transdural portion and/or the intradural assembly; and wire leads connecting through the transdural portion to the electrodes; said device in fully assembled form being transformable from an open position to a clamped position; wherein the open position configures the device for insertion through an incision in the dura, placing the intradural portion inside the dura; wherein the clamped position secures the device to the dura with the electrodes in direct contact with the cerebrospinal fluid by clamping the dura between the intradural assembly and the extradural assembly.

3. The device of claim 2, wherein the intradural assembly is affixed to the transdural portion, and the extradural assembly is configured to pass over the outside surface of the transdural portion towards the intradural assembly.

4. The device of claim 3, wherein the outside surface of the transdural portion around the longitudinal axis is cylindrical.

5. The device of claim 3, wherein the transdural portion has an external thread that is configured to receive a separate locking nut that screws down the transdural portion, thereby securing the extradural assembly to the intradural assembly.

6. The device of claim 3, comprising a snap fastener configured to fasten the extradural assembly to the transdural portion, thereby securing the device in the clamped position.

7. The device of claim 2, wherein the intradural assembly is operable from a retracted or insert position to a deployed position in which a clamping portion of the intradural assembly extends radially beyond the outside surface of the transdural portion.

8. The device of a claim 2, where the intradural assembly and the extradural assembly are oval, ellipsoidal, rectangular, or oblong in shape so as to occlude the incision between them and form a water-tight closure when the device is in the clamped position,
wherein the extradural assembly and the intradural assembly each have a perimeter such that the perimeter of the extradural assembly aligns with the perimeter of the intradural assembly.

9. The device of claim 1, which is constructed and arranged to keep the electrodes 0.05 to 8 mm away from the surface of the spinal cord when implanted into the subject.

10. The device of claim 2, further comprising a means for securing the device to a spinal vertebra.

11. The device of claim 2, further comprising a stabilizing or laminoplasty plate, configured to be affixed to the transdural or extradural assembly of the device, and also to a vertebra of the spinal cord, thereby securing the device at a fixed position in relation to the spinal cord.

12. The device of claim 2, wherein the transdural portion of the device extends beyond the extradural portion, exposing an external thread that is configured to receive a locking nut that screws down the transdural portion so as to secure the device to the stabilizing plate.

13. The device of claim 2, further comprising a socket or coupling that is configured for reversibly securing the device to a positioning tool such that the device can be manipulated to place the intradural assembly inside the dura, whereupon the positioning tool can be removed from the socket or coupling.

14. The spinal cord stimulating device according to claim 2; in combination with a positioning tool that is reversibly connected to the device such that the device can be manipulated to place the intradural assembly inside the dura, whereupon the positioning tool can be removed from the device;
wherein the positioning tool is configured so as to change the device from an open position for surgically conforming the device to span the dura of a subject's spinal cord to a clamped position wherein the device is secured to the dura.

15. The spinal cord stimulating device according to claim 14, wherein the positioning tool is configured to screw a locking nut down the transdural assembly, thereby clamping the extradural assembly to the intradural assembly so as to secure the device to the dura.

16. A combination for spinal cord stimulation in a subject, comprising:
a spinal cord stimulating device according to claim 2;
a signal source configured and programmed to deliver electrical stimulation to the spinal cord of a subject by way of the device, wherein the electrical stimulation varies or fluctuates at a frequency of at least 200 or 500 Hz; and
a wire lead configured to electronically connect the device to the signal source upon implantation of the device and the signal source into the subject.

17. A method of treating pain or spasticity in a subject, comprising delivering to the spinal cord of the subject an electrical stimulation by way of a device according to claim 2 that has been secured to the dura of the spinal cord in the subject, thereby relieving the pain without stimulating dorsal nerve rootlets.

18. A device for spinal cord stimulation, configured for traversing and securing to the dura surrounding the spinal cord of a subject, the device comprising:
a transdural portion that includes an outside surface and a longitudinal axis;
an intradural assembly that conforms to an internal surface of the dura, wherein the intradural assembly is either affixed or is slidably or rotatably connected to the transdural portion and has a clamping portion that extends or is extendible to a position that is radially beyond the outside surface of the transdural portion;
an extradural assembly that conforms to an external surface of the dura, wherein the extradural assembly is either affixed or is slidably or rotatably connected to the transdural portion and has a clamping portion that extends or is extendible to a position that is radially beyond the outside surface of the transdural portion; and
one or more electrodes included in the transdural portion and/or the intradural assembly;
wherein the intradural and/or extradural assembly includes an aperture that is complementary to and encompasses the outside surface of the transdural portion, thereby configuring the respective assembly to slide over or around the outside surface of the transdural portion such that the spacing between the intradural and extradural assemblies can be narrowed from an open position to a clamped position;
wherein the intradural assembly is configured to pass through a short incision in the dura surrounding the spinal cord when in the device is in the open position, leaving the extradural assembly outside the dura, whereafter sliding or rotating the extradural assembly and/or the intradural assembly over or around the outside surface of the transdural portion to narrow the distance in between and securing the intradural and extradural assemblies in the clamped position has the effect of clamping the dura between the clamping portions of the intradural and extradural assemblies.

19. A method of preparing a subject for spinal cord stimulation, comprising:
(a) gaining surgical access to the dura surrounding the spinal cord of the subject;
(b) making a short incision in the dura;
(c) obtaining a spinal cord stimulation device according to claim 2 that includes a transdural portion, one or more electrodes, an intradural assembly, and an extradural assembly;
(d) positioning the device such that the intradural assembly is inside the dura, the transdural portion passes from inside the dura to outside the dura; and the extradural assembly is outside the dura;
(e) narrowing the distance between the intradural assembly and the extradural assembly to a clamped position; and
(f) securing the intradural and/or the extradural assembly in place so as to sustain the clamped position, thereby securing the device to the dura and preferably sealing the dura to prevent leakage of cerebrospinal fluid into the epidural compartment or egress of epidural effluents into the intradural compartment.

20. The method of claim 19, wherein the narrowing comprises screwing a locknut down a transdural portion of the device, and electrically connecting the device to a signal source that is configured and programmed to deliver electrical stimulation to the spinal cord of the subject by way of the electrodes of the device.

* * * * *